US012790588B2

(12) United States Patent
Goldberg et al.

(10) Patent No.: US 12,790,588 B2
(45) Date of Patent: Nov. 10, 2026

(54) SKIN TISSUE

(71) Applicant: THE UNIVERSITY OF DURHAM, Durham (GB)

(72) Inventors: Martin Goldberg, Durham (GB); Iakowos Karakesisoglou, Durham (GB); James Carthew, Victoria (AU)

(73) Assignee: THE UNIVERSITY OF DURHAM, Durham (GB)

( * ) Notice: Subject to any disclaimer, the term of this patent is extended or adjusted under 35 U.S.C. 154(b) by 201 days.

(21) Appl. No.: 18/452,726

(22) Filed: Aug. 21, 2023

(65) Prior Publication Data

US 2024/0067925 A1 Feb. 29, 2024

Related U.S. Application Data

(62) Division of application No. 16/481,771, filed as application No. PCT/GB2018/050120 on Jan. 17, 2018, now Pat. No. 11,773,371.

(30) Foreign Application Priority Data

Jan. 30, 2017 (GB) ...................................... 1701438

(51) Int. Cl.
*C12N 5/071* (2010.01)
*G01N 33/50* (2006.01)

(52) U.S. Cl.
CPC ....... *C12N 5/0629* (2013.01); *G01N 33/5082* (2013.01); *C12N 2503/06* (2013.01); *C12N 2513/00* (2013.01)

(58) Field of Classification Search
None
See application file for complete search history.

(56) References Cited

U.S. PATENT DOCUMENTS

2009/0258006 A1* 10/2009 Weiss ..................... C07K 16/18 424/130.1
2014/0161917 A1* 6/2014 Lyga ...................... A61Q 19/08 435/6.13

FOREIGN PATENT DOCUMENTS

WO 00/24371 A1 5/2000

OTHER PUBLICATIONS

Wang, Wenjia et al. Structural insights into SUN-KASH complexes across the nuclear envelope. Cell Research (2012) 22:1440-1452. (Year: 2012).*

U.S. Appl. No. 16/481,771, “Advisory Action”, Jan. 26, 2023, 3 pages.

U.S. Appl. No. 16/481,771, “Final Office Action”, Nov. 16, 2022, 11 pages.

U.S. Appl. No. 16/481,771, “Non-Final Office Action”, May 20, 2022, 14 pages.

U.S. Appl. No. 16/481,771, “Notice of Allowance”, May 26, 2023, 12 pages.

Xu et al., “[Percutaneous penetration of ketoprofen and ketoprofen isopropyl ester through a tissue engineering skin reconstructed with HaCaT cells].—PubMed—NCBI”, Sep. 1, 2005 (Sep. 1, 2005), XP055456013, Retrieved from the Internet: URL:https://www.ncbi.nlm.nih.gov/pubmed/16342676 [retrieve on Mar. 2, 2018] abstract.

Lu et al., “Nesprin interchain associations control nuclear size”, CMLS Cellular and Molecular Life Sciences, Birkhauser-Verlag, BA, vol. 69, No. 20, Jun. 1, 2012 (Jun. 1, 2012), pp. 3493-3509.

Hieda, Miki “Implications for Diverse Functions of the LINC Complexes Based on the Structure”, Cells, vol. 6, No. 4, Jan. 26, 2017 (Jan. 26, 2017), p. 3.

International Search Report and Written Opinion issued Mar. 22, 2018, International Application No. PCT/GB2018/050120, 16 pages.

Rashmi, R.N. et al. The nuclear envelope protein Nesprin-2 has roles in cell proliferation and differentiation during wound healing. Nucleus 3:2. pp. 172-186. (Year: 2012) .

Lonza. Amaxa Cell Line Nucleofector Kit V. (Year: 2009).

* cited by examiner

*Primary Examiner* — Nghi V Nguyen
(74) *Attorney, Agent, or Firm* — Kilpatrick Townsend & Stockton LLP

(57) ABSTRACT

A method of creating skin tissue is described, particularly, an in vitro or ex vivo method for creating skin tissue. The invention extends to the use of agents that disrupt the LINC complex in a skin cell to create the skin tissue, and to using the created tissue in an assay to identify or screen anti-ageing compounds. The invention further extends to model skin tissues per se, uses thereof and to kits for creating such model skin tissues.

20 Claims, 19 Drawing Sheets

Specification includes a Sequence Listing.

SKIN TISSUE

CROSS-REFERENCE TO RELATED APPLICATIONS

This application is a divisional application of U.S. application Ser. No. 16/481,771, filed Jul. 29, 2019, which is the National Stage of International Application No. PCT/GB2018/050120, filed Jan. 17, 2018, which claims priority to United Kingdom Application No. 1701438.2, filed Jan. 30, 2017, the contents of all of which are incorporated by reference in their entirety.

REFERENCE TO A "SEQUENCE LISTING," A TABLE, OR A COMPUTER PROGRAM LISTING APPENDIX SUBMITTED ON A COMPACT DISK

This application contains a Sequence Listing submitted electronically and is hereby incorporated by reference in its entirety. The Sequence Listing .xml filed is entitled 095095-000701US-1402048_ST26_Sequence_Listing.xml is 43,630 bytes in size and was created on Nov. 8, 2023.

TECHNICAL FIELD

The present invention relates to a method of creating skin tissue, and particularly, although not exclusively, to an in vitro or ex vivo method for creating skin tissue. The invention extends to the use of agents that disrupt the LINC complex in a skin cell to create the skin tissue, and to using the created tissue in an assay to identify or screen anti-ageing compounds. The invention further extends to model skin tissues per se, uses thereof and to kits for creating such model skin tissues.

BACKGROUND

The foundation of tissue engineering is the generation of biomechanically, biochemically, structurally and topologically defined synthetic 3D biomaterials that mimic the native extracellular microenvironment of cells. Progress has been made in the development of organotypic equivalents. However, generating proper biomimetic scaffolds presents significant technical challenges. Tissue engineering is time consuming, involves high costs and there are major issues regarding biofunctionality, compatibility and variability, which severely impair their biomedical usage. A major limitation is that native microenvironments are highly variable and complex and their biochemical, biomechanical and structural compositions are difficult to replicate in the laboratory. Epidermal keratinocytes, for example, rest on a stiff (MPa) collagen IV/VII and laminin-rich 2D extracellular matrix (ECM) termed the basement membrane (BM), while dermal fibroblasts reside on considerably softer (0.1-10 kPa) collagen III/I and fibrillin/elastin-based 3D matrixes. ECM properties, including composition, porosity, stiffness, structure and importantly the immediate cellular surrounding, control cell properties, e.g. identity, proliferation, longevity, signalling, behaviour and architecture. Therefore, designing universal scaffolds that determine the correct properties of different cell/tissue types is not feasible because, for instance, epidermal keratinocytes will naturally exist in a very different physical environment to a dermal fibroblast.

There is therefore a need for an improved means of inducing in vitro or ex vivo cells, such as keratinocytes, in such a way so as to accurately model the structural, biomechanical and biochemical properties of corresponding cells that are found in the in vivo skin tissue.

BRIEF SUMMARY OF THE DISCLOSURE

The inventors have found that although in vivo cellular microenvironments vary in different tissues, the mechanisms by which cells sense and react to their environment are the same. Extracellular cues from the ECM and other factors are sensed by plasma membrane receptors that translate these signals into intracellular biochemical messengers and biomechanical forces that modulate chromatin organization and gene expression. The LINC (Linker of the Nucleoskeleton and Cytoskeleton) complex is a central switch of this molecular and structural circuit. Instead of engineering an appropriate extracellular environment for keratinocytes in vitro, that will ignite proper LINC complex signalling, the inventors modulated directly the LINC complex in keratinocytes using a dominant negative protein-based approach. In other words, instead of using signals from outside the cell to determine cellular properties, the inventors operated the "LINC switch" directly. By doing so, they were surprisingly able to affect cellular signalling (e.g. TGF-beta, wnt etc.), cell-cell adhesion, cell-ECM interactions, cellular biomechanics, cell architecture and importantly cellular organization.

DETAILED DESCRIPTION

Thus, according to a first aspect of the invention, there is provided a method of preparing skin tissue, the method comprising:

(i) contacting a skin cell with an agent that disrupts the LINC complex of the cell;

(ii) culturing the cell on a substrate comprising culture media to induce proliferation of the cell into a plurality of cells; and (iii) removing a portion of culture media from the substrate such that the plurality of cells are disposed in an interface between culture media remaining on the substrate and air, to thereby induce differentiation of the cells into skin tissue.

Advantageously, the method according to the first aspect can be used to create skin in vitro or ex vivo without the use of a biomimetic scaffold, i.e. a scaffold that mimics the extracellular microenvironment of cells found in normal skin tissue. Thus, the above-mentioned problems associated with the use of such a scaffold are avoided. Furthermore, the method of the invention can be used to create tissue comprising cells that exhibit biochemical, biomechanical and structural properties similar or even identical to that of corresponding cells in tissue, in vivo. Moreover, the inventors have found that disrupting the LINC complex in cells, such as keratinocytes, makes the cells significantly softer compared to their wild type counterparts. In addition, disrupting the LINC complex in cells causes the cells to organize themselves into compact colonies when grown in 2D. Importantly, when cells that have a disrupted LINC complex are grown in 3D, they form multi-layered and properly organized epidermal structures much faster than normal epithelial cells.

As shown in the method of the first aspect above, culturing cells, in which the LINC complex has been disrupted, under suitable conditions causes them to proliferate and differentiate into skin cells without the use of a biomimetic scaffold. In one embodiment, the method is an in vitro and/or ex vivo method.

The LINC complex is an intracellular network of multiple proteins found in eukaryotic cells. It spans the nuclear membrane and connects genetic material (and other nuclear components) to plasma membrane receptors via cytoskeletal structures (see FIGS. 1 and 2). Consequently, the LINC complex influences multiple cellular processes, including nuclear positioning, force transduction and cell signalling pathways. The core proteins of the LINC complex are Nesprins, SUN proteins and lamins (see FIGS. 1 and 2).

Nesprins (Nuclear envelope spectrin repeat proteins) are a family of spectrin proteins primarily situated in the outer nuclear membrane of cells. They function as adaptors that connect the nucleus of a cell to the cytoskeleton, microtubule associated motor proteins (e.g. dynein and kinesin-1) and the centrosome. The Nesprin family comprises four subtypes of nesprin (i.e. Nesprin-1, Nesprin-2, Nesprin-3 and Nesprin-4), each of which has multiple isoforms. The largest isoforms of Nesprin-1 and Nesprin-2 are over 800 kDa in weight, and referred to as giant Nesprin proteins. Giant Nesprin-1 and giant Nesprin-2 comprise an N-terminal F-actin binding domain (ABD), a long spectrin repeat containing region and a C-terminal transmembrane domain followed by a short region that projects into the nuclear envelope and connects to the SUN domain of SUN proteins (i.e. the KASH domain). All giant nesprins isoforms contain an ABD. Most, but not all isoforms of Nesprin contain a KASH domain.

Four genes, which are referred to as SYNE1, SYNE2, SYNE3 and SYNE4, encode Nesprin subtypes Nesprin-1, Nesprin-2, Nesprin-3 and Nesprin-4, respectively. Each subtype of Nesprin has multiple isoforms due to alternative transcriptional initiation, termination and splicing of the gene by which they are encoded.

The first gene, SYNE1, encodes the Nesprin-1 subtype. The nucleotide sequence that encodes one embodiment of SYNE1 can be found under genomic identifier ENSG00000131018.

The KASH domain of the Nesprin-1 subtype is encoded by a single exon, which also encodes a stop codon at the 3' end of the SYNE1 gene. In one embodiment, the nucleotide sequence of the exon that encodes the KASH domain of the Nesprin-1 subtype is referred to herein as SEQ ID No. 1 (previously referred to as SEQ ID No. 2 in patent application GB1701438.2), as follows:

[SEQ ID No. 1]
GTCCACAAAAGGTGGCTCCGATTCCTCCCTTTCTGAGCCAGGGCCAGGTC
GGTCCGGCCGCGGCTTCCTGTTCAGAGTCCTCCGAGCAGCTCTTCCCCTT
CAGCTTCTCCTGCTCCTCCTCATCGGGCTTGCCTGCCTTGTACCAATGTC
AGAGGAAGACTACAGCTGTGCCCTCTCCAACAACTTTGCCCGGTCATTCC
ACCCCATGCTCAGATACACGAATGGCCCTCCTCCACTCTGA

In one embodiment, the amino acid sequence that encodes the KASH domain of the Nesprin-1 subtype is referred to herein as SEQ ID No. 2 (previously referred to as SEQ ID No. 3 in patent application GB1701438.2), as follows:

[SEQ ID No. 2]
AALPLQLLLLLLIGLACLVPMSEEDYSCALSNNFARSFHPMLRYTNGPP
PL

The second gene, SYNE2, encodes the Nesprin-2 subtype. The nucleotide sequence that encodes one embodiment of SYNE2 can be found under genomic identifier ENSG00000054654.

The KASH domain of the Nesprin-2 subtype is encoded by a single exon, which also encodes a stop codon at the 3' end of the SYNE2 gene. In one embodiment, the nucleotide sequence of the exon that encodes the KASH domain of the Nesprin-2 subtype is referred to herein as SEQ ID No. 3 (previously referred to as SEQ ID No. 5 in patent application GB1701438.2), as follows:

[SEQ ID No. 3]
GGTCCCCGGCAGCACACGGCCACAGCGCTCCTTCCTCTCAAGGGTGGTCC
GGGCAGCCCTACCCCTGCAGCTGCTCCTCCTGCTGCTGCTGCTCCTGGCC
TGCCTGCTGCCCTCCTCCGAAGAAGACTACAGCTGCACTCAGGCCAACAA
CTTTGCCCGGTCCTTTTACCCCATGCTGAGGTACACCAATGGGCCACCCC
CCACATAG

In one embodiment, the amino acid sequence that encodes the KASH domain of the Nesprin-2 subtype is referred to herein as SEQ ID No. 4 (previously referred to as SEQ ID No. 6 in patent application GB1701438.2), as follows:

[SEQ ID No. 4]
AALPLQLLLLLLLLLACLLPSSEEDYSCTQANNFARSFYPMLRYTNGPP
PT

The third gene, SYNE3 encodes the Nesprin-3 subtype. The nucleotide sequence that encodes one embodiment of SYNE3 can be found under genomic identifier ENSG00000176438.

ENSG00000176438 encodes five different mRNA transcripts (i.e. SYNE3-001, -002, -003, -004 and -005). Only transcripts SYNE3-001, -003, -004, and -005 encode a Nesprin protein. Transcript SYNE3-005 encodes a Nesprin-3 protein, which is equivalent to the murine Nesprin-3a isoform. Nesprins encoded by SYNE3-004-003, -004 and -005 comprise a KASH domain.

The KASH domain of the Nesprin-3 subtype is encoded by a single exon, which also encodes a stop codon at the 3' end of the SYNE3 gene. In one embodiment, the nucleotide sequence of the exon that encodes the KASH domain of the Nesprin-3 subtype is referred to herein as SEQ ID No. 5 (previously referred to as SEQ ID No. 8 in patent application GB1701438.2), as follows:

[SEQ ID No. 5]
ACTCGGCGGTGGCGAGGACTGGGCTCCCTCTTCCGGAGGGCGTGCTGTGT
GGCGCTCCCACTGCAGCTGCTTCTGCTGCTGTTCCTCCTCCTGCTGTTCC
TGCTCCCAATCAGGGAAGAGGACCGCAGCTGCACCCTGGCCAACAACTTC
GCCCGCTCCTTCACGCTCATGCTGCGCTACAATGGCCCACCACCCACCTA
A

In one embodiment, the amino acid sequence that encodes the KASH domain of Nesprin-3 is referred to herein as SEQ ID No. 6 (previously referred to as SEQ ID No. 9 in patent application GB1701438.2), as follows:

[SEQ ID No. 6]
VALPLQLLLLLFLLLLFLLPIREEDRSCTLANNFARSFTLMLRYNGPPPT

The fourth gene, SYNE 4 encodes Nesprin-4. The nucleotide sequence that encodes one embodiment of Nesprin-4 can be found under genomic identifier ENSG0000181392.

SYNE4 encodes seven different mRNA transcripts (i.e. SYNE4-001, -002, -003, -004, -005, -006, and -007). Only transcripts SYNE4-001, -003, -004, -005 and -006 encode proteins. Transcript SYNE4-001 encodes Nesprin-4 protein. Transcripts SYNE4-001 and -004 encode isoforms comprising a KASH domain.

The KASH domain of the Nesprin-4 subtype is encoded by a single exon, which also encodes a stop codon at the 3' end of the SYNE4 gene. In one embodiment, the nucleotide sequence of the exon that encodes the KASH domain of the Nesprin-4 subtype is referred to herein as SEQ ID No. 7 (previously referred to as SEQ ID No. 11 in patent application GB1701438.2), as follows:

[SEQ ID No. 7]
GGCCCCCGATCCTGCATCCAGGCAGCCTCTGACCTTCCTCCTTATCCTCT

TCCTCCTCTTCCTCCTCCTGGTGGGTGCCATGTTTCTCCTGCCCGCGTCA

GGAGGCCCCTGCTGCTCTCATGCCCGAATACCCAGGACACCCTACCTGGT

GCTCAGCTATGTCAATGGTCTTCCCCCAGTCTGA

In one embodiment, the amino acid sequence that encodes the KASH domain of Nesprin-4 is referred to herein as SEQ ID No. 8 (previously referred to as SEQ ID No. 12 in patent application GB1701438.2), as follows:

[SEQ ID No. 8]
FLLILFLLFLLLVGAMFLLPASGGPCCSHARIPRTPYLVLSYVNGLPPV

Thus, in one embodiment of the invention, the LINC complex that is disrupted in step (i) of the method of the invention may comprise a Nesprin protein. The Nesprin protein may be selected from Nesprin-1, Nesprin-2, Nesprin-3 and Nesprin-4. Preferably, the Nesprin protein is Nesprin-1, Nesprin-2 or Nesprin-4. Most preferably, the Nesprin protein comprises a KASH domain.

The LINC complex that is disrupted in step (i) of the method may comprise a protein encoded by SYNE1, SYNE2, SYNE3 and/or SYNE4, or a variant or fragment thereof. Preferably, the Nesprin protein is encoded by SYNE1, SYNE2 and/or SYNE4.

The LINC complex that is disrupted in step (i) of the method may comprise a Nesprin protein encoded by a nucleotide sequence substantially as set out in any one or more of the nucleotide sequences found under genomic identifiers ENSG00000131018, ENSG00000054654, ENSG00000176438 and/or ENSG00000181392, or a variant or fragment thereof. Preferably, the Nesprin protein is encoded by a nucleotide sequence substantially as the nucleotide sequences found under genomic identifiers ENSG00000131018, ENSG00000054654, ENSG00000176438 and/or ENSG00000181392, or a variant or fragment thereof.

The LINC complex that is disrupted in step (i) of the method may comprise a KASH domain. The KASH domain may be encoded by a nucleotide sequence substantially as set out in SEQ ID No. 1, 3, 5 and/or 7, or a variant or fragment thereof. Most preferably, the Nesprin protein comprises a KASH domain encoded by a nucleotide sequence substantially as set out in SEQ ID No. 1, 3, 5 and/or 7, or a variant or fragment thereof. The KASH domain may comprise an amino acid sequence substantially as set out in SEQ ID No. 2, 4, 6 and/or 8, or a variant or fragment thereof. Most preferably, the KASH domain comprises an amino acid sequence substantially as set out in SEQ ID No. 2, 4, 6 and/or 8, or a variant or fragment thereof.

SUN (Sade and UNC-84 homology) proteins are a family of proteins primarily located in the perinuclear space (i.e. between the outer and inner nuclear membrane) and nucleoplasm of cells (see FIG. 2). Consequently, the KASH domains and C-terminal domains of SUNs "bridge" the inner and outer nuclear membranes. However, SUN proteins also link the inner nuclear membranes (INM) to the underlying nuclear lamina and chromatin (see FIG. 2).

SUN proteins comprise an N-terminal domain, a transmembrane domain, a coiled-coil domain, and a conserved C-terminal domain (the SUN domain), which binds to the KASH domain of Nesprins, see, for example, FIGS. 2 and 3. The C-terminal domain and the coiled-coil domain are located in the perinuclear space, whereas the N-terminal domain is located in the nucleoplasm.

Five subtypes of SUN proteins are found in vertebrates, SUN1, SUN2, SUN3, SUN4 (sperm associated antigen 4, SPAG4) and SUN5 (SPAG4 like, SPAGL, Astrin). In mice, there are at least seven different isoforms of the SUN1 subtype, all of which contain identical C-terminal SUN domain sequences but vary in their nucleoplasmic N-terminal sequences. Like the full-length SUN2 protein, the majority of SUN1 isoforms are widely expressed.

The nucleotide sequence of one embodiment of SUN1 can be found under genomic identifier ENSG00000164828. There are 35 splice variants of SUN1, which are referred to herein as SUN1-001, SUN1-002 . . . to SUN1-035, respectively.

The nucleotide sequence that encodes one embodiment of the SUN1 SUN-domain is referred to herein as SEQ ID No. 9 (previously referred to as SEQ ID No. 14 in patent application GB1701438.2), as follows:

[SEQ ID No. 9]
GTGGCAGCATCTTGAGTACTCGCTGTTCTGAAACTTACGAAACCAAAACG

GCGCTGATGAGTCTGTTTGGGATCCCGCTGTGGTACTTCTCGCAGTCCCC

GCGCGTGGTCATCCAGCCTGACATTTACCCCGGTAACTGCTGGGCATTTA

AAGGCTCCCAGGGGTACCTGGTGGTGAGGCTCTCCATGATGATCCACCCA

GCCGCCTTCACTCTGGAGCACATCCCTAAGACGCTGTCGCCAACAGGCAA

CATCAGCAGCGCCCCCAAGGACTTCGCCGTCTATGGATTAGAAAATGAGT

ATCAGGAAGAAGGGCAGCTTCTGGGACAGTTCACGTATGATCAGGATGGG

GAGTCGCTCCAGATGTTCCAGGCCCTGAAAAGACCCGACGACACAGCTTT

CCAAATAGTGGAACTTCGGATTTTTTCTAACTGGGGCCATCCTGAGTATA

CCTGTCTGTATCGGTTCAGAGTTCATGGCGAACCTGTCAAGTGA

The amino acid sequence that encodes one embodiment of the SUN1 SUN-domain is referred to herein as SEQ ID No. 10, as follows:

[SEQ ID No. 10]
GSILSTRCSETYETKTALMSLFGIPLWYFSQSPRVVIQPDIYPGNCWAFK

GSQGYLVVRLSMMIHPAAFTLEHIPKTLSPTGNISSAPKDFAVYGLENEY

-continued

QEEGQLLGQFTYDQDGESLQMFQALKRPDDTAFQIVELRIFSNWGHPEYT

CLYRFRVHGEPVK

The nucleotide sequence that encodes one embodiment of SUN2 can be found under genomic identifier ENSG00000100242. There are 18 splice variants of SUN2, which are referred to herein as SUN2-001, SUN2-002 . . . to SUN2-018, respectively.

The nucleotide sequence that encodes one embodiment of the SUN2 SUN-domain is referred to herein as SEQ ID No. 11 (previously referred to as SEQ ID No. 17 in patent application GB1701438.2), as follows:

[SEQ ID No. 11]

GGGCCAGCGTCATCAGCACCCGATGTTCTGAGACCTACGAGACCAAGACG

GCCCTCCTCAGCCTCTTCGGCATCCCCCTGTGGTACCACTCCCAGTCACC

CCGAGTCATCCTCCAGCCAGATGTGCACCCAGGCAACTGCTGGGCCTTCC

AGGGGCCACAAGGCTTCGCCGTGGTCCGCCTCTCTGCCCGCATCCGCCCC

ACAGCCGTTACCTTAGAGCATGTGCCCAAGGCCTTGTCACCCAACAGCAC

TATCTCCAGTGCCCCCAAGGACTTCGCCATCTTTGGGTTTGACGAAGACC

TGCAGCAGGAGGGGACACTCCTTGGCAAGTTCACTTACGATCAGGACGGC

GAGCCTATTCAGACGTTTCACTTTCAGGCCCCTACGATGGCCACGTACCA

GGTGGTGGAGCTGCGGATCCTGACTAACTGGGGCCACCCCGAGTACACCT

GCATCTACCGCTTCAGAGTGCATGGGGAGCCCGCCCACTAG

The amino acid sequence that encodes one embodiment of the SUN2 SUN-domain is referred to herein as SEQ ID No. 12 (previously referred to as SEQ ID No. 18 in patent application GB1701438.2), as follows:

[SEQ ID No. 12]

ASVISTRCSETYETKTALLSLFGIPLWYHSQSPRVILQPDVHPGNCWAFQ

GPQGFAVVRLSARIRPTAVTLEHVPKALSPNSTISSAPKDFAIFGFDEDL

QQEGTLLGKFTYDQDGEPIQTFHFQAPTMATYQVVELRILTNWGHPEYTC

IYRFRVHGEPAH

The nucleotide sequence that encodes one embodiment of SUN3 can be found under genomic identifier ENSG00000164744 There are 10 splice variants of SUN3, which are referred to herein as SUN3-001, SUN3-002 . . . to SUN1-010, respectively.

The nucleotide sequence that encodes one embodiment of the SUN3 SUN-domain is referred to herein as SEQ ID No. 13 (previously referred to as SEQ ID No. 20 in patent application GB1701438.2), as follows:

[SEQ ID No. 13]

GAGCCTCCATCATTGAAGCTGGGACCTCAGAAAGTTATAAAAATAATAAA

GCAAAATTGTACTGGCATGGGATAGGTTTCCTAAATCATGAAATGCCTCC

AGATATTATTCTTCAGCCGGATGTCTACCCTGGAAAGTGCTGGGCTTTTC

CAGGTTCCCAGGGTCATACCCTAATCAAGCTTGCTACAAAGATCATACCA

ACTGCTGTTACCATGGAGCACATCTCAGAGAAGGTGTCTCCGTCAGGAAA

-continued

CATCTCCAGTGCACCCAAGGAATTTTCTGTCTATGGCATCACAAAAAAAT

GTGAAGGAGAAGAAATTTTCCTAGGTCAGTTTATATATAACAAAACAGGA

ACCACCGTTCAAACATTTGAACTCCAGCATGCAGTTTCTGAATATTTATT

ATGTGTGAAACTTAATATCTTTAGCAACTGGGGACACCCGAAGTATACTT

GTTTATATCGATTCAGGGTCCATGGCACACCAGGCAAGCACATCTAG

The amino acid sequence that encodes one embodiment of the SUN3 SUN-domain is referred to herein as SEQ ID No. 14 (previously referred to as SEQ ID No. 21 in patent application GB1701438.2), as follows:

[SEQ ID No. 14]

ASIIEAGTSESYKNNKAKLYWHGIGFLNHEMPPDIILQPDVYPGKCWAFP

GSQGHTLIKLATKIIPTAVTMEHISEKVSPSGNISSAPKEFSVYGITKKC

EGEEIFLGQFIYNKTGTTVQTFELQHAVSEYLLCVKLNIFSNWGHPKYTC

LYRFRVHGTPGKHI

The nucleotide sequence of one embodiment of SUN4 (SPAG4) can be found under genomic identifier ENSG00000061656. There are 7 splice variants of SUN1, which are referred to herein as SUN4-001, SUN4-002 . . . to SUN4-007, respectively.

The nucleotide sequence that encodes one embodiment of the SUN4 SUN-domain is referred to herein as SEQ ID No. 15 (previously referred to as SEQ ID No. 23 in patent application GB1701438.2), as follows:

[SEQ ID No. 15]

GAGCCTCCATCGACCTGCAGAAGACATCCCACGATTACGCAGACAGGAAC

ACTGCCTACTTCTGGAATCGCTTCAGCTTCTGGAACTACGCACGGCCGCC

CACGGTTATCCTGGAGCCCCACGTGTTCCCTGGGAATTGCTGGGCTTTTG

AAGGCGACCAAGGCCAGGTGGTGATCCAACTGCCGGGCCGAGTGCAGCTG

AGCGACATCACTCTGCAGCATCCACCGCCCAGCGTGGAGCACACCGGAGG

AGCCAACAGCGCCCCCCGCGATTTCGCGGTCTTTGGCCTCCAGGTTTATG

ATGAAACTGAAGTTTCCTTGGGGAAATTCACCTTCGATGTTGAGAAATCG

GAGATTCAGACTTTCCACCTGCAGAATGACCCCCCAGCTGCCTTTCCCAA

GGTGAAGATCCAGATTCTAAGCAACTGGGGCCACCCCCGTTTCACGTGCT

TGTATCGAGTCCGTGCCCACGGTGTGCGAACCTCAGAGGGGGCAGAGGGC

AGTGCACAGGGGCCCCATTAA

The amino acid sequence that encodes one embodiment of the SUN4 SUN-domain is referred to herein as SEQ ID No. 16 (previously referred to as SEQ ID No. 24 in patent application GB1701438.2), as follows:

[SEQ ID No. 16]

ASIDLQKTSHDYADRNTAYFWNRFSFWNYARPPTVILEPHVFPGNCWAFE

GDQGQVVIQLPGRVQLSDITLQHPPPSVEHTGGANSAPRDFAVFGLQVYD

ETEVSLGKFTFDVEKSEIQTFHLQNDPPAAFPKVKIQILSNWGHPRFTCL

YRVRAHGVRTSEGAEGSAQGPH

The nucleotide sequence that encodes one embodiment of SUN5 can be found under genomic identifier ENSG00000167098. There are 4 splice variants of SUN5, which are referred to herein as SUN5-001, SUN5-002, SUN5-004 and SUN5-004, respectively.

The nucleotide sequence that encodes one embodiment of the SUN5 SUN-domain is referred to herein as SEQ ID No. 17 (previously referred to as SEQ ID No. 26 in patent application GB1701438.2), as follows:

[SEQ ID No. 17]
GGGCCAGCATTGACTTTGAGCACACGTCAGTCACCTATAACCATGAGAAG

GCCCACTCCTACTGGAACTGGATCCAGCTGTGGAACTACGCACAGCCCCC

AGACGTGATCCTTGAGCCCAACGTGACACCTGGCAATTGCTGGGCCTTTG

AGGGTGACCGCGGCCAGGTGACCATCCAATTGGCTCAGAAGGTTTACCTG

TCCAACCTCACGCTGCAGCACATCCCCAAGACCATCTCATTGTCAGGCAG

CCTGGACACCGCCCCCAAGGACTTCGTCATCTATGGCATGGAGGGCTCCC

CCAAGGAGGAGGTGTTCCTGGGGGCATTTCAGTTTCAGCCAGAAAACATC

ATCCAGATGTTCCCACTCCAGAACCAGCCGGCCCGGGCTTTCAGTGCGGT

CAAGGTGAAGATCTCAAGCAACTGGGGGAACCCAGGCTTCACTTGCCTGT

ACCGCGTGCGAGTGCATGGCTCTGTGGCCCCGCCCAGAGAGCAGCCTCAC

CAGAACCCCTACCCTAAGAGAGATTAA

The amino acid sequence that encodes one embodiment of the SUN5 SUN-domain is referred to herein as SEQ ID No. 18 (previously referred to as SEQ ID No. 27 in patent application GB1701438.2) as follows:

[SEQ ID No. 18]
ASIDFEHTSVTYNHEKAHSYWNWIQLWNYAQPPDVILEPNVTPGNCWAFE

GDRGQVTIQLAQKVYLSNLTLQHIPKTISLSGSLDTAPKDFVIYGMEGSP

KEEVFLGAFQFQPENIIQMFPLQNQPARAFSAVKVKISSNWGNPGFTCLY

RVRVHGSVAPPREQPHQNPYPKRD

Thus, in one embodiment of the invention, the LINC complex that is disrupted in step (i) of the method of the invention may comprise a SUN protein. The SUN protein may be selected from SUN1, SUN2, SUN3, SUN4 and SUN5. Preferably, the SUN protein is SUN1 or SUN2. Most preferably, the SUN protein comprises a SUN domain. The SUN protein may be encoded by a nucleotide sequence substantially as set out in the nucleotide sequences found under genomic identifiers ENSG00000164828, ENSG0000010242, ENSG00000164744, ENSG00000061656 or ENSG00000167098, or a variant or fragment thereof. Preferably, the SUN protein is encoded by a nucleotide sequence substantially as set out in the nucleotide sequences found under genomic identifiers ENSG00000164828 or ENSG00000100242, or a variant or fragment thereof. The LINC complex which is disrupted in step (i) of the method of the invention may comprise a SUN domain. The SUN domain may be encoded by a nucleotide sequence substantially as set out in SEQ ID No. 9, 11, 13, 15 and/or 17, or a variant or fragment thereof. Most preferably, the SUN protein comprises a SUN domain encoded by a nucleotide sequence substantially as set out in SEQ ID No. 9 or SEQ ID No. 11, or a variant or fragment thereof. The SUN domain comprises an amino acid nucleotide sequence substantially as set out in SEQ ID No.10, 12, 14, 16 and/or 18, or a variant or fragment thereof. Most preferably, the SUN domain comprises an amino acid sequence substantially as set out in SEQ ID No. 10 or SEQ ID No. 12, or a variant or fragment thereof.

Lamins are a family of proteins primarily located in the nuclear lamina (i.e. on the inner face of the inner nuclear membrane). They attach to SUN proteins and act as an anchor. It is believed that this attachment enables force exerted by the components of the cytoskeleton to be transmitted directly to the nucleus. Lamins comprise A-type Lamins and B-type Lamins.

A-type Lamins are encoded by a single gene, LMNA, which undergoes alternative splicing to generate Lamins A and C. The nucleotide sequence of LMNA can be found under genomic identifier ENSG00000160789

The nucleotide sequence that encodes of one embodiment of Lamin A (ENST00000368300) is referred to herein as SEQ ID No. 19 (previously referred to as SEQ ID No. 29 in patent application GB1701438.2), as follows:

[SEQ ID No. 19]
ATGGAGACCCCGTCCCAGCGGCGCGCCACCCGCAGCGGGGCGCAGGCCAG

CTCCACTCCGCTGTCGCCCACCCGCATCACCCGGCTGCAGGAGAAGGAGG

ACCTGCAGGAGCTCAATGATCGCTTGGCGGTCTACATCGACCGTGTGCGC

TCGCTGGAAACGGAGAACGCAGGGCTGCGCCTTCGCATCACCGAGTCTGA

AGAGGTGGTCAGCCGCGAGGTGTCCGGCATCAAGGCCGCCTACGAGGCCG

AGCTCGGGGATGCCCGCAAGACCCTTGACTCAGTAGCCAAGGAGCGCGCC

CGCCTGCAGCTGGAGCTGAGCAAAGTGCGTGAGGAGTTTAAGGAGCTGAA

AGCGCGCAATACCAAGAAGGAGGGTGACCTGATAGCTGCTCAGGCTCGGC

TGAAGGACCTGGAGGCTCTGCTGAACTCCAAGGAGGCCGCACTGAGCACT

GCTCTCAGTGAGAAGCGCACGCTGGAGGGCGAGCTGCATGATCTGCGGGG

CCAGGTGGCCAAGCTTGAGGCAGCCCTAGGTGAGGCCAAGAAGCAACTTC

AGGATGAGATGCTGCGGCGGGTGGATGCTGAGAACAGGCTGCAGACCATG

AAGGAGGAACTGGACTTCCAGAAGAACATCTACAGTGAGGAGCTGCGTGA

GACCAAGCGCCGTCATGAGACCCGACTGGTGGAGATTGACAATGGGAAGC

AGCGTGAGTTTGAGAGCCGGCTGGCGGATGCGCTGCAGGAACTGCGGGCC

CAGCATGAGGACCAGGTGGAGCAGTATAAGAAGGAGCTGGAGAAGACTTA

TTCTGCCAAGCTGGACAATGCCAGGCAGTCTGCTGAGAGGAACAGCAACC

TGGTGGGGGCTGCCCACGAGGAGCTGCAGCAGTCGCGCATCCGCATCGAC

AGCCTCTCTGCCCAGCTCAGCCAGCTCCAGAAGCAGCTGGCAGCCAAGGA

GGCGAAGCTTCGAGACCTGGAGGACTCACTGGCCCGTGAGCGGGACACCA

GCCGGCGGCTGCTGGCGGAAAAGGAGCGGGAGATGGCCGAGATGCGGGCA

AGGATGCAGCAGCAGCTGGACGAGTACCAGGAGCTTCTGGACATCAAGCT

GGCCCTGGACATGGAGATCCACGCCTACCGCAAGCTCTTGGAGGGCGAGG

AGGAGAGGCTACGCCTGTCCCCCAGCCCTACCTCGCAGCGCAGCCGTGGC

CGTGCTTCCTCTCACTCATCCCAGACACAGGGTGGGGGCAGCGTCACCAA

AAAGCGCAAACTGGAGTCCACTGAGAGCCGCAGCAGCTTCTCACAGCACG

CACGCACTAGCGGGCGCGTGGCCGTGGAGGAGGTGGATGAGGAGGGCAAG

TTTGTCCGGCTGCGCAACAAGTCCAATGAGGACCAGTCCATGGGCAATTG

-continued

GCAGATCAAGCGCCAGAATGGAGATGATCCCTTGCTGACTTACCGGTTCC

CACCAAAGTTCACCCTGAAGGCTGGGCAGGTGGTGACGATCTGGGCTGCA

GGAGCTGGGGCCACCCACAGCCCCCCTACCGACCTGGTGTGGAAGGCACA

GAACACCTGGGGCTGCGGGAACAGCCTGCGTACGGCTCTCATCAACTCCA

CTGGGGAAGAAGTGGCCATGCGCAAGCTGGTGCGCTCAGTGACTGTGGTT

GAGGACGACGAGGATGAGGATGGAGATGACCTGCTCCATCACCACCACGG

CTCCCACTGCAGCAGCTCGGGGGACCCCGCTGAGTACAACCTGCGCTCGC

GCACCGTGCTGTGCGGGACCTGCGGGCAGCCTGCCGACAAGGCATCTGCC

AGCGGCTCAGGAGCCCAGGTGGGCGGACCCATCTCCTCTGGCTCTTCTGC

CTCCAGTGTCACGGTCACTCGCAGCTACCGCAGTGTGGGGGGCAGTGGGG

GTGGCAGCTTCGGGGACAATCTGGTCACCCGCTCCTACCTCCTGGGCAAC

TCCAGCCCCCGAACCCAGAGCCCCCAGAACTGCAGCATCATGTAA

The amino acid sequence that encodes one embodiment of Lamin A (ENSP00000357283) is referred to herein as SEQ ID No. 20 (previously referred to as SEQ ID No. 30 in patent application GB1701438.2), as follows:

[SEQ ID No. 20]

METPSQRRATRSGAQASSTPLSPTRITRLQEKEDLQELNDRLAVYIDRVR

SLETENAGLRLRITESEEVVSREVSGIKAAYEAELGDARKTLDSVAKERA

RLQLELSKVREEFKELKARNTKKEGDLIAAQARLKDLEALLNSKEAALST

ALSEKRTLEGELHDLRGQVAKLEAALGEAKKQLQDEMLRRVDAENRLQTM

KEELDFQKNIYSEELRETKRRHETRLVEIDNGKQREFESRLADALQELRA

QHEDQVEQYKKELEKTYSAKLDNARQSAERNSNLVGAAHEELQQSRIRID

SLSAQLSQLQKQLAAKEAKLRDLEDSLARERDTSRRLLAEKEREMAEMRA

RMQQQLDEYQELLDIKLALDMEIHAYRKLLEGEEERLRLSPSPTSQRSRG

RASSHSSQTQGGGSVTKKRKLESTESRSSFSQHARTSGRVAVEEVDEEGK

FVRLRNKSNEDQSMGNWQIKRQNGDDPLLTYRFPPKFTLKAGQVVTIWAA

GAGATHSPPTDLVWKAQNTWGCGNSLRTALINSTGEEVAMRKLVRSVTVV

EDDEDEDGDDLLHHHHGSHCSSSGDPAEYNLRSRTVLCGTCGQPADKASA

SGSGAQVGGPISSGSSASSVTVTRSYRSVGGSGGGSFGDNLVTRSYLLGN

SSPRTQSPQNCSIM

The nucleotide sequence that encodes one embodiment of Lamin C (ENST00000368301) is referred to herein as SEQ ID No. 21 (previously referred to as SEQ ID No. 31 in patent application GB1701438.2), as follows:

[SEQ ID No. 21]

ATGGAGACCCCGTCCCAGCGGCGCGCCACCCGCAGCGGGGCGCAGGCCAG

CTCCACTCCGCTGTCGCCCACCCGCATCACCCGGCTGCAGGAGAAGGAGG

ACCTGCAGGAGCTCAATGATCGCTTGGCGGTCTACATCGACCGTGTGCGC

TCGCTGGAAACGGAGAACGCAGGGCTGCGCCTTCGCATCACCGAGTCTGA

AGAGGTGGTCAGCCGCGAGGTGTCCGGCATCAAGGCCGCCTACGAGGCCG

AGCTCGGGGATGCCCGCAAGACCCTTGACTCAGTAGCCAAGGAGCGCGCC

CGCCTGCAGCTGGAGCTGAGCAAAGTGCGTGAGGAGTTTAAGGAGCTGAA

-continued

AGCGCGCAATACCAAGAAGGAGGGTGACCTGATAGCTGCTCAGGCTCGGC

TGAAGGACCTGGAGGCTCTGCTGAACTCCAAGGAGGCCGCACTGAGCACT

GCTCTCAGTGAGAAGCGCACGCTGGAGGGCGAGCTGCATGATCTGCGGGG

CCAGGTGGCCAAGCTTGAGGCAGCCCTAGGTGAGGCCAAGAAGCAACTTC

AGGATGAGATGCTGCGGCGGGTGGATGCTGAGAACAGGCTGCAGACCATG

AAGGAGGAACTGGACTTCCAGAAGAACATCTACAGTGAGGAGCTGCGTGA

GACCAAGCGCCGTCATGAGACCCGACTGGTGGAGATTGACAATGGGAAGC

AGCGTGAGTTTGAGAGCCGGCTGGCGGATGCGCTGCAGGAACTGCGGGCC

CAGCATGAGGACCAGGTGGAGCAGTATAAGAAGGAGCTGGAGAAGACTTA

TTCTGCCAAGCTGGACAATGCCAGGCAGTCTGCTGAGAGGAACAGCAACC

TGGTGGGGGCTGCCCACGAGGAGCTGCAGCAGTCGCGCATCCGCATCGAC

AGCCTCTCTGCCCAGCTCAGCCAGCTCCAGAAGCAGCTGGCAGCCAAGGA

GGCGAAGCTTCGAGACCTGGAGGACTCACTGGCCCGTGAGCGGGACACCA

GCCGGCGGCTGCTGGCGGAAAAGGAGCGGGAGATGGCCGAGATGCGGGCA

AGGATGCAGCAGCAGCTGGACGAGTACCAGGAGCTTCTGGACATCAAGCT

GGCCCTGGACATGGAGATCCACGCCTACCGCAAGCTCTTGGAGGGCGAGG

AGGAGAGGCTACGCCTGTCCCCCAGCCCTACCTCGCAGCGCAGCCGTGGC

CGTGCTTCCTCTCACTCATCCCAGACACAGGGTGGGGGCAGCGTCACCAA

AAAGCGCAAACTGGAGTCCACTGAGAGCCGCAGCAGCTTCTCACAGCACG

CACGCACTAGCGGGCGCGTGGCCGTGGAGGAGGTGGATGAGGAGGGCAAG

TTTGTCCGGCTGCGCAACAAGTCCAATGAGGACCAGTCCATGGGCAATTG

GCAGATCAAGCGCCAGAATGGAGATGATCCCTTGCTGACTTACCGGTTCC

CACCAAAGTTCACCCTGAAGGCTGGGCAGGTGGTGACGATCTGGGCTGCA

GGAGCTGGGGCCACCCACAGCCCCCCTACCGACCTGGTGTGGAAGGCACA

GAACACCTGGGGCTGCGGGAACAGCCTGCGTACGGCTCTCATCAACTCCA

CTGGGGAAGAAGTGGCCATGCGCAAGCTGGTGCGCTCAGTGACTGTGGTT

GAGGACGACGAGGATGAGGATGGAGATGACCTGCTCCATCACCACCACGT

GAGTGGTAGCCGCCGCTGA

The amino acid sequence that encodes one embodiment of Lamin C (ENSP00000357284) is referred to herein as SEQ ID No. 22 (previously referred to as SEQ ID No. 32 in patent application GB1701438.2), as follows:

[SEQ ID No. 22]

METPSQRRATRSGAQASSTPLSPTRITRLQEKEDLQELNDRLAVYIDRVR

SLETENAGLRLRITESEEVVSREVSGIKAAYEAELGDARKTLDSVAKERA

RLQLELSKVREEFKELKARNTKKEGDLIAAQARLKDLEALLNSKEAALST

ALSEKRTLEGELHDLRGQVAKLEAALGEAKKQLQDEMLRRVDAENRLQTM

KEELDFQKNIYSEELRETKRRHETRLVEIDNGKQREFESRLADALQELRA

QHEDQVEQYKKELEKTYSAKLDNARQSAERNSNLVGAAHEELQQSRIRID

SLSAQLSQLQKQLAAKEAKLRDLEDSLARERDTSRRLLAEKEREMAEMRA

RMQQQLDEYQELLDIKLALDMEIHAYRKLLEGEEERLRLSPSPTSQRSRG

-continued

RASSHSSQTQGGGSVTKKRKLESTESRSSFSQHARTSGRVAVEEVDEEGK

FVRLRNKSNEDQSMGNWQIKRQNGDDPLLTYRFPPKFTLKAGQVVTIWAA

GAGATHSPPTDLVWKAQNTWGCGNSLRTALINSTGEEVAMRKLVRSVTVV

EDDEDEDGDDLLHHHHVSGSRR

B-type Lamins are categorised as Lamin B1 or Lamin B2. Lamin B1 is encoded by LMNB1 and Lamin B2 is encoded by LMNB2.

The nucleotide sequence that encodes one embodiment of LMNB1 can be found under genomic identifier ENSG00000113368.

The nucleotide sequence that encodes another embodiment of LMNB1 can be found under genomic identifier ENST00000261366, and is referred to herein as SEQ ID No. 23 (previously referred to as SEQ ID No. 34 in patent application GB1701438.2), as follows:

[SEQ ID No. 23]

ATGGCGACTGCGACCCCCGTGCCGCCGCGGATGGGCAGCCGCGCTGGCGG

CCCCACCACGCCGCTGAGCCCCACGCGCCTGTCGCGGCTCCAGGAGAAGG

AGGAGCTGCGCGAGCTCAATGACCGGCTGGCGGTGTACATCGACAAGGTG

CGCAGCCTGGAGACGGAGAACAGCGCGCTGCAGCTGCAGGTGACGGAGCG

CGAGGAGGTGCGCGGCCGTGAGCTCACCGGCCTCAAGGCGCTCTACGAGA

CCGAGCTGGCCGACGCGCGACGCGCGCTCGACGACACGGCCCGCGAGCGC

GCCAAGCTGCAGATCGAGCTGGGCAAGTGCAAGGCGGAACACGACCAGCT

GCTCCTCAACTATGCTAAGAAGGAATCTGATCTTAATGGCGCCCAGATCA

AGCTTCGAGAATATGAAGCAGCACTGAATTCGAAAGATGCAGCTCTTGCT

ACTGCACTTGGTGACAAAAAAAGTTTAGAGGGAGATTTGGAGGATCTGAA

GGATCAGATTGCCCAGTTGGAAGCCTCCTTAGCTGCAGCCAAAAAACAGT

TAGCAGATGAAACTTTACTTAAAGTAGATTTGGAGAATCGTTGTCAGAGC

CTTACTGAGGACTTGGAGTTTCGCAAAAGCATGTATGAAGAGGAGATTAA

CGAGACCAGAAGGAAGCATGAAACGCGCTTGGTAGAGGTGGATTCTGGGC

GTCAAATTGAGTATGAGTACAAGCTGGCGCAAGCCCTTCATGAGATGAGA

GAGCAACATGATGCCCAAGTGAGGCTGTATAAGGAGGAGCTGGAGCAGAC

TTACCATGCCAAACTTGAGAATGCCAGACTGTCATCAGAGATGAATACTT

CTACTGTCAACAGTGCCAGGGAAGAACTGATGGAAAGCCGCATGAGAATT

GAGAGCCTTTCATCCCAGCTTTCTAATCTACAGAAAGAGTCTAGAGCATG

TTTGGAAAGGATTCAAGAATTAGAGGACTTGCTTGCTAAAGAAAAAGACA

ACTCTCGTCGCATGCTGACAGACAAAGAGAGAGAGATGGCGGAAATAAGG

GATCAAATGCAGCAACAGCTGAATGACTATGAACAGCTTCTTGATGTAAA

GTTAGCCCTGGACATGGAAATCAGTGCTTACAGGAAACTCTTAGAAGGCG

AAGAAGAGAGGTTGAAGCTGTCTCCAAGCCCTTCTTCCCGTGTGACAGTA

TCCCGAGCATCCTCAAGTCGTAGTGTACGTACAACTAGAGGAAAGCGGAA

GAGGGTTGATGTGGAAGAATCAGAGGCGAGTAGTAGTGTTAGCATCTCTC

ATTCCGCCTCAGCCACTGGAAATGTTTGCATCGAAGAAATTGATGTTGAT

GGGAAATTTATCCGCTTGAAGAACACTTCTGAACAGGATCAACCAATGGG

-continued

AGGCTGGGAGATGATCAGAAAAATTGGAGACACATCAGTCAGTTATAAAT

ATACCTCAAGATATGTGCTGAAGGCAGGCCAGACTGTTACAATTTGGGCT

GCAAACGCTGGTGTCACAGCCAGCCCCCCAACTGACCTCATCTGGAAGAA

CCAGAACTCGTGGGGCACTGGCGAAGATGTGAAGGTTATATTGAAAAATT

CTCAGGGAGAGGAGGTTGCTCAAAGAAGTACAGTCTTTAAAACAACCATA

CCTGAAGAAGAGGAGGAGGAGGAAGAAGCAGCTGGAGTGGTTGTTGAGGA

AGAACTTTTCCACCAGCAGGGAACCCCAAGAGCATCCAATAGAAGCTGTG

CAATTATGTAA

The amino acid sequence that encodes one embodiment of Lamin B1 (ENSP00000261366) is referred to herein as SEQ ID No. 24 (previously referred to as SEQ ID No. 35 in patent application G131701438.2), as follows:

[SEQ ID No. 24]

MATATPVPPRMGSRAGGPTTPLSPTRLSRLQEKEELRELNDRLAVYIDKV

RSLETENSALQLQVTEREEVRGRELTGLKALYETELADARRALDDTARER

AKLQIELGKCKAEHDQLLLNYAKKESDLNGAQIKLREYEAALNSKDAALA

TALGDKKSLEGDLEDLKDQIAQLEASLAAAKKQLADETLLKVDLENRCQS

LTEDLEFRKSMYEEEINETRRKHETRLVEVDSGRQIEYEYKLAQALHEMR

EQHDAQVRLYKEELEQTYHAKLENARLSSEMNTSTVNSAREELMESRMRI

ESLSSQLSNLQKESRACLERIQELEDLLAKEKDNSRRMLTDKEREMAEIR

DQMQQQLNDYEQLLDVKLALDMEISAYRKLLEGEEERLKLSPSPSSRVTV

SRASSSRSVRTTRGKRKRVDVEESEASSSVSISHSASATGNVCIEEIDVD

GKFIRLKNTSEQDQPMGGWEMIRKIGDTSVSYKYTSRYVLKAGQTVTIWA

ANAGVTASPPTDLIWKNQNSWGTGEDVKVILKNSQGEEVAQRSTVFKTTI

PEEEEEEEEAAGVVVEEELFHQQGTPRASNRSCAIM

The nucleotide sequence that encodes one embodiment of LMNB2 can be found under genomic identifier ENSG00001176619.

The nucleotide sequence that encodes another embodiment of LMNB2 (ENST00000325327) is referred to herein as SEQ ID No. 25 (previously referred to as SEQ ID No. 37 in patent application GB1701438.2), as follows:

[SEQ ID No. 25]

ATGAGCCCGCCGAGCCCGGGCCGCCGTCGGGAGCAGCGCAGGCCGCGAGC

CGCCGCCACCATGGCCACGCCGCTGCCCGGCCGCGCGGGCGGGCCCGCCA

CGCCGCTGTCGCCCACGCGCCTGTCGCGGCTGCAGGAGAAGGAGGAGCTG

CGCGAGCTCAACGACCGCCTGGCGCACTACATCGACCGCGTCCGCGCGCT

GGAGCTGGAGAACGACCGGCTCCTGCTCAAGATCTCAGAGAAGGAGGAGG

TGACCACGCGCGAGGTGAGTGGCATCAAGGCGCTGTACGAGTCGGAGCTG

GCCGATGCCCGGAGAGTCCTGGATGAGACGGCTCGAGAGCGTGCCCGGCT

GCAGATAGAGATTGGGAAGCTGAGGGCAGAGTTGGACGAGGTCAACAAGA

GCGCCAAGAAGAGGGAGGGCGAGCTTACGGTGGCCCAGGGCCGTGTGAAG

GACCTGGAGTCCCTGTTCCACCGGAGCGAGGTGGAGCTGGCAGCTGCCCT

CAGCGACAAGCGCGGCCTGGAGAGTGACGTGGCTGAGCTGCGGGCCCAGC

-continued

TGGCCAAGGCCGAGGACGGTCATGCAGTGGCCAAAAAGCAGCTGGAGAAG

GAGACGCTGATGCGTGTGGACCTGGAGAACCGCTGCCAGAGCCTGCAGGA

GGAGCTGGACTTCCGGAAGAGTGTGTTCGAGGAGGAGGTGCGGGAGACGC

GGCGGCGGCACGAGCGGCGCCTGGTGGAGGTGGACAGCAGCCGGCAGCAG

GAGTACGACTTCAAGATGGCACAGGCGCTGGAGGAGCTGCGGAGCCAGCA

CGACGAGCAAGTGCGGCTCTACAAGCTGGAGCTGGAGCAGACCTACCAGG

CCAAGCTGGACAGCGCCAAGCTGAGCTCTGACCAGAACGACAAGGCGGCC

AGTGCGGCTCGCGAGGAGCTGAAGGAGGCCCGCATGCGCCTGGAGTCCCT

CAGCTACCAGCTCTCCGGCCTCCAGAAGCAGGCCAGTGCCGCTGAAGATC

GCATTCGGGAGCTGGAGGAGGCCATGGCCGGGGAGCGGGACAAGTTCCGG

AAGATGCTGGACGCCAAGGAGCAGGAGATGACGGAGATGCGGGACGTGAT

GCAGCAGCAGCTGGCCGAGTACCAGGAGCTGCTGGACGTGAAGCTGGCCC

TGGACATGGAGATCAACGCCTACCGGAAGCTCCTGGAGGGCGAGGAGGAG

AGGCTGAAGCTGTCCCCCAGCCCATCCTCGCGCGTCACCGTCTCACGAGC

CACCTCGAGCAGCAGCGGCAGCTTGTCCGCCACCGGGCGCCTGGGCCGCA

GTAAGCGGAAGCGGCTGGAGGTGGAGGAGCCCTTGGGCAGCGGCCCAAGC

GTCCTGGGCACGGGCACGGGTGGCAGCGGTGGCTTCCACCTGGCCCAGCA

GGCCTCGGCCTCGGGTAGCGTCAGCATCGAGGAGATCGACCTGGAGGGCA

AGTTTGTGCAGCTCAAGAACAACTCGGACAAGGATCAGTCTCTGGGGAAC

TGGAGAATCAAGAGGCAGGTCTTGGAGGGGGAGGAGATCGCCTACAAGTT

CACGCCCAAGTACATCCTGCGCGCCGGCCAGATGGTCACGGTGTGGGCAG

CTGGTGCGGGGGTGGCCCACAGCCCCCCCTCGACGCTGGTGTGGAAGGGC

CAGAGCAGCTGGGGCACGGGCGAGAGCTTCCGCACCGTCCTGGTTAACGC

GGATGGCGAGGAAGTGGCCATGAGGACTGTGAAGAAGTCCTCGGTGATGC

GTGAGAATGAGAATGGGGAGGAAGAGGAGGAGGAAGCCGAGTTTGGCGAG

GAGGATCTTTTCCACCAACAGGGGGACCCGAGGACCACCTCAAGAGGCTG

CTACGTGATGTGA

The amino acid sequence that encodes one embodiment of Lamin B2 (ENSP00000327054) is referred to herein as SEQ ID No. 26 (previously referred to as SEQ ID No. 38 in patent application GB1701438.2), as follows:

[SEQ ID No. 26]

MSPPSPGRRREQRRPRAAATMATPLPGRAGGPATPLSPTRLSRLQEKEEL

RELNDRLAHYIDRVRALELENDRLLLKISEKEEVTTREVSGIKALYESEL

ADARRVLDETARERARLQIEIGKLRAELDEVNKSAKKREGELTVAQGRVK

DLESLFHRSEVELAAALSDKRGLESDVAELRAQLAKAEDGHAVAKKQLEK

ETLMRVDLENRCQSLQEELDFRKSVFEEEVRETRRRHERRLVEVDSSRQQ

EYDFKMAQALEELRSQHDEQVRLYKLELEQTYQAKLDSAKLSSDQNDKAA

SAAREELKEARMRLESLSYQLSGLQKQASAAEDRIRELEEAMAGERDKFR

KMLDAKEQEMTEMRDVMQQQLAEYQELLDVKLALDMEINAYRKLLEGEEE

RLKLSPSPSSRVTVSRATSSSSGSLSATGRLGRSKRKRLEVEEPLGSGPS

-continued

VLGTGTGGSGGFHLAQQASASGSVSIEEIDLEGKFVQLKNNSDKDQSLGN

WRIKRQVLEGEEIAYKFTPKYILRAGQMVTVWAAGAGVAHSPPSTLVWKG

QSSWGTGESFRTVLVNADGEEVAMRTVKKSSVMRENENGEEEEEEAEFGE

EDLFHQQGDPRTTSRGCYVM

Thus, in one embodiment of the invention, the LINC complex that is disrupted in step (i) of the method of the invention may comprise a Lamin protein. The Lamin protein may be an A-type Lamin and/or a B-type Lamin. The B-type Lamin may be Lamin B1 or Lamin B2. Preferably, the Lamin protein is a Lamin A, Lamin C and/or Lamin B1. The Lamin protein may be encoded by a nucleotide sequence substantially as set out under genomic identifiers ENSG00000160789, ENSG00000113368, ENSG00000176619 and/or in SEQ ID Nos. 19, 21, 23 and/or 25, or a variant or fragment thereof. Preferably, the Lamin protein is encoded by a nucleotide sequence substantially as set out under genomic identifiers ENSG00000160789, ENSG00000113368, ENSG00000176619 and/or in SEQ ID No.19, 21, 23 and/or 25 or a variant or fragment thereof. The Lamin protein comprises an amino acid sequence substantially as set out in SEQ ID Nos. 20, 22, 24 and/or 26, or a variant or fragment thereof. Preferably, the Lamin protein comprises an amino acid sequence substantially as set out in SEQ ID No. 20, 22, 24 and/or 26, or a variant or fragment thereof. The Lamin protein may be encoded by LMNA, LMNB1 and/or LMNB2, or a variant or fragment thereof. Preferably, the Lamin protein is encoded by LMNA and/or LMNB1, or a variant or fragment thereof.

Thus, step (i) of the method may comprise disrupting the translation or function of one or more of the above LINC proteins, or the transcription or function of one or more of the above nucleotides that encode a LINC complex protein, such as a SUN protein, a Nesprin protein or a Lamin protein.

Although a single protein complex (i.e. the LINC complex) acts as an intracellular cellular "switch" that physically links cellular nuclei to their extracellular environment, the constituents of the LINC complex may vary in different tissue or cell types. For example, in keratinocytes, giant Nesprin-2 is the dominant isoform of nesprin. Giant Nesprin-2 commonly binds to SUN1 and SUN2. Preferably, therefore, the LINC complex that is disrupted in step (i) comprises giant Nesprin-2 and SUN1 and/or SUN2.

The complexity of the LINC complex may also be increased by virtue of the fact that LINC complex proteins may bind to each other with a 3:3 stoichiometry. Preferably, the LINC complex that is disrupted in step (i) comprises a Nesprin and a SUN protein. Preferably the Nesprin protein comprises a KASH domain and the SUN protein comprises a SUN domain. Even more preferably, the Nesprins and SUN proteins are bound to each other with a 3:3 stoichiometry to form a hexameric complex. Most preferably, the Nesprins comprise a KASH domain and the SUN proteins comprise a SUN domain. Therefore, the LINC complex that is disrupted in step (i) may be a hexameric complex of three SUN proteins and three Nesprin proteins. Nesprin paralogues bind promiscuously to SUN-domains, which are essential for Nesprin recruitment to the outer nuclear membrane. SUN1 and SUN2 proteins play partially redundant roles and interact with each other via their luminal coiled-coil segments, forming heteromeric stable complexes. Therefore, it is believed that LINC hexamers may comprise mixed Nesprin and SUN-domain paralogue combinations.

Thus, in one embodiment, the hexameric complex that is disrupted in step (i) of the method may be heteromeric (i.e. comprise two or three different subtypes of a SUN protein and/or two or three different subtypes of Nesprin protein).

In another embodiment, the hexameric LINC complex that is disrupted in step (i) of the method may be a homomeric complex of SUN proteins (i.e. comprise three identical subtypes of SUN) or a homomeric complex of Nesprin proteins (i.e. comprise three identical subtypes of Nesprin). Preferably, the LINC complex is a heteromeric or homomeric complex of Nesprins that each comprise a Nesprin with a KASH domain, and/or SUN proteins that each comprise a SUN domain.

The presence of multiple subtypes and isoforms of proteins that comprise a SUN-domain or a KASH-domain suggests that the LINC complex may be a diverse and multi-functional complex. Given that several core constituents of the LINC complex exhibit cell-type and tissue specificity, distinct LINC complexes can be assumed to form that may perform specific tasks to accommodate the physiology requirements of the respective cell and tissue.

Preferably, however, the LINC complex that is disrupted in step (i) of the method comprises (i) a Nesprin protein, which, via its KASH domain, is bound to the SUN domain of a SUN protein; and/or (2) a SUN protein, which is bound to a lamin protein. Most preferably, the LINC complex comprises a Nesprin protein, which, via its KASH domain, is bound to the SUN domain of a SUN protein.

Accordingly, therefore, the agent that disrupts the LINC complex may be an agent that:

(i) reduces or is configured to reduce the concentration of a LINC complex protein compared to the concentration of the LINC complex protein in the absence of the agent (for example, by inhibiting the transcription of a nucleotide encoding a LINC complex protein and/or inhibiting translation of an RNA molecule encoding a LINC complex protein);

(ii) inhibits or is configured to inhibit the binding of one LINC complex protein to another LINC complex protein; or (iii) promotes or is configured to promote degradation of the LINC complex or one or more of the LINC complex proteins.

In one embodiment, an agent that inhibits the concentration of a LINC complex protein is a Non-steroidal anti-inflammatory drug (NSAID). The NSAID may inhibit the concentration of Nesprin proteins. Preferably, the NSAID inhibits the concentration of Nesprin-2. The NSAID may be an agent that inhibits the enzyme activity of cyclooxygenase 1 or 2 (COX1 or COX2), such as ibuprofen, naproxen, indomethacin and aspirin. Preferably, the NSAID is an agent that inhibits the enzyme activity of COX1, such as sullindac sulphide.

In one embodiment, an agent that inhibits binding of one LINC complex protein to another LINC complex protein may be a pharmacological agent, such as a small molecule, a peptide, an antibody or an intrabody. An agent that disrupts the LINC complex may be an agent that inhibits or is configured to inhibit binding of a Nesprin protein to a SUN protein, preferably by inhibiting binding of a KASH domain to a SUN domain. Preferably the agent disrupts binding of KASH domain to a SUN domain. The agent may therefore be a modified Nesprin protein that does not comprise a KASH domain, or a variant or a fragment thereof. The modified Nesprin may comprise an N-terminal F-actin binding domain (ABD), a long spectrin repeat containing region and a C-terminal transmembrane domain, or a variant or a fragment thereof. The agent may be an antibody or an intrabody that binds to the KASH domain of a Nesprin. Preferably, the modified Nesprin protein is expressed in the cytoplasm.

In one embodiment, the agent may be a modified Nesprin that consists of a KASH domain. Therefore, the modified Nesprin may not comprise an N-terminal F-actin binding domain (ABD), a long spectrin repeat containing region and/or a C-terminal transmembrane domain. Preferably, the modified Nesprin is expressed or present in the nuclear envelope.

In one embodiment, the agent may be a modified SUN protein that comprises a SUN domain or the SUN domain together with other regions located in the perinuclear space, such as the coiled-coil domain. Therefore, the modified SUN protein does not comprise any domains located in the nucleoplasm, such as the N-terminal domain. Thus, the modified SUN protein may comprise a SUN domain, or a SUN domain and coiled-coil domain, or a variant or a fragment thereof. Preferably, the modified SUN protein is expressed or present in the perinuclear envelope/space. Preferably, the agent or modified SUN protein disrupts binding of SUN proteins, which comprise a SUN domain, to the KASH domain of Nesprins. In a preferred embodiment, the modified SUN protein is referred to herein as SEQ ID No. 27 (previously referred to as SEQ ID No. 39 in patent application GB1701438.2), as follows:

[SEQ ID No. 27]

```
VSLWGQGNFFSLLPVLNWTAMQPTQRVDDSKGMHRPGPLPPSPPPKVDHK
ASQWPQESDMGQKVASLSAQCHNHDERLAELTVLLQKLQIRVDQVDDGRE
GLSLWVKNVVGQHLQEMGTIEPPDAKTDFMTFHHDHEVRLSNLEDVLRKL
TEKSEAIQKELEETKLKAGSRDEEQPLLDRVQHLELELNLLKSQLSDWQH
LKTSCEQAGARIQETVQLMFSEDQQGGSLEWLLEKLSSRFVSKDELQVLL
HDLELKLLQNITHHITVTGQAPTSEAIVSAVNQAGISGITEAQAHIIVNN
ALKLYSQDKTGMVDFALESGGGSILSTRCSETYETKTALLSLFGVPLWYF
SQSPRVVIQPDIYPGNCWAFKGSQGYLVVRLSMKIYPTTFTMEHIPKTLS
PTGNISSAPKDFAVYGLETEYQEEGQPLGRFTYDQEGDSLQMFHTLERPD
QAFQIVELRVLSNWGHPEYTCLYRFRVHGEPIQ
```

Thus, the agent may comprise an amino acid sequence substantially as set out in SEQ ID No. 26, or a variant or fragment thereof.

In one embodiment, the agent may be a modified SUN protein that consists of a SUN domain. Thus, the modified SUN protein may comprise a coiled-coil domain, a transmembrane domain and/or an N-terminal domain, or a variant or a fragment thereof. Preferably, the modified SUN protein is expressed or present in the perinuclear envelope and the nucleoplasm. Preferably, the agent or modified SUN protein disrupts binding of SUN proteins, which comprise a SUN domain, to the KASH domain of Nesprins.

In another embodiment, the agent that disrupts the LINC complex may be a gene-silencing molecule. A gene-silencing molecule is any molecule that interferes with the transcription a nucleotide (gene) encoding a protein of the LINC complex. Such molecules include, but are not limited to, RNAi molecules, including siNA, siRNA, miRNA, ribozymes and antisense molecules. Alternatively, the agent may be any molecule that interferes with the translation of an RNA encoding a protein of a LINC complex.

The skin cell used of step (i) of the method according to the invention may be a primary cell derived from skin tissue or a cell from ex vivo tissue. The skin cell of step (i) of the method according to the invention may be a mammalian cell or a human cell. The skin cell of step (i) of the method according to the invention may be an immortalised cell that has been derived from skin tissue. The skin cell of step (i) of the method according to the invention may be derived from a layer of skin. The layer of skin may be the epidermis, the dermis or the hypodermis. Preferably, the skin cell of step (i) of the method according to the invention is derived from the epidermis. The skin cell of step (i) of the method according to the invention may be a fibroblast, a keratinocyte, a melanocyte, a Merkel cell or a Langerhans cell. Most preferably, the cell is a keratinocyte.

The agent may be introduced into the cell by contacting the cell with the agent, intracellular injection, electroporation, transgenic expression or any other known suitable technique.

It will be appreciated that conditions for culturing cells in vitro or ex vivo so that they develop into a tissue will vary depending on the type of cell being cultured. The skilled person therefore would appreciate that if, for example, culturing a keratinocyte such that it develops into epidermal tissue, the keratinocytes may need to be cultured under conditions that promote proliferation and differentiation. In vitro or ex vitro culture conditions that promote proliferation of keratinocytes include 37° C., 5% $CO_2$ and culture media. In vitro or ex vitro culture conditions that promote differentiation of keratinocytes into skin tissue include culturing the keratinocytes on the surface of culture media at 37° C. and 5% $CO_2$.

Step (ii) of the method (i.e. culturing step (ii)), which is used to induce proliferation of the cell, may comprise culturing the cell at 34 to 39° C. or 35 to 38° C. Preferably, the culturing step comprises culturing the cell at about 37° C. The cell may be cultured for at least 6, 12, 18, 24, 36, 48, 96 or 168 hours. Preferably, the cell is cultured for at least 48 hours. The cell may be cultured at 35 to 38° C. for at least 6, 12, 18, 24, 36, 48, 96 or 168 hours. Most preferably, the cell is cultured at 35 to 38° C. for at least 48 hours.

Step (iii) of the method (i.e. culturing step (iii)), which is used to induce differentiation of the cells, may comprise culturing the cells at 34 to 39° C. or 35 to 38° C. Preferably, the culturing step comprises culturing the cells at about 37° C. The cells may be cultured for at least 6, 12, 18, 24, 36, 48, 96 or 168 hours. Preferably, the cells are cultured for at least 48 hours. The cells may be cultured at 35 to 38° C. for at least 6, 12, 18, 24, 36, 48, 96 or 168 hours. Most preferably, the cells are cultured at 35 to 38° C. for at least 48 hours.

Preferably, the culture media and the cell are disposed on the surface of the substrate. The substrate may be an insert or mesh that can be placed in a culture plate. The insert or mesh may be made of plastic. Preferably, the insert is a porous two-dimensional insert or a three-dimensional mesh. The advantage of using a porous insert or a three-dimensional mesh is that it enables the cell/cells to be fed with culture media disposed in the holes of the insert or mesh. Another advantage of the porous substrate or 3D mesh is that it enables the proliferating cells to form layers of cells.

Removing culture media from the cells such that they are disposed in the air-media interface, arrests proliferation and induces expression of proteins found in terminally differentiated cells. For example, keratinocytes stop expressing proteins that are responsible for attachment to the basement membrane (hemidesmosomes), they remodel their cell-to-cell junctions (desmosomes), they remodel their cytoskeleton (in particular, they stop expression keratin-5/-14 and start expressing keratin-1/-10) and they express proteins that will form a highly crosslinked protein-lipid structure (the cornified envelope). This whole process leads to the loss of cell nuclei and the formation of the stratum corneum, which is the uppermost layer of the skin. This layer of skin comprises dead cells that seal off the epidermis from the outside. The inventors have used keratin-10 as a biomarker of differentiated cells. As shown in FIGS. 9A-9B, keratin-10 staining is more pronounced in the cells comprising a LINC mutant than wild type cells. Hence, ex vivo or in vitro disruption of the LINC complex encourages cellular differentiation.

According to a second aspect, there is provided a skin tissue obtained or obtainable by the method according to the first aspect.

According to a third aspect, there is provided a kit for creating a skin tissue, the kit comprising a skin cell and an agent that disrupts the LINC complex.

In a fourth aspect, there is provided use of an agent that disrupts the LINC complex in a skin cell to create a skin tissue.

In a fifth aspect, there is provided a method of testing the effects of a test compound on the properties of a skin tissue, the method comprising contacting a skin tissue according to the second aspect or a skin tissue created by the method according to the first aspect with a test compound and measuring the effects of the test compound on the properties of the skin tissue.

The properties of the skin tissue that are measured in the method according to the fifth aspect may be cell identity, cell proliferation, cell differentiation, cell longevity, cell stratification (layers formed), cell signalling, cell behaviour, cell architecture, barrier function, cell/tissue stiffness, skin corrosion, electrical resistance and/or cornified envelope formation.

The way in which the properties of the skin tissue are measured, will be determined by the properties being measured. The skilled person would appreciate that cell identity, cell proliferation, cell differentiation, cell longevity, cell stratification (layers formed), cell signalling, cell behaviour, cell architecture, barrier function, cell/tissue stiffness, skin corrosion, electrical resistance and/or cornified envelope formation will be measured using techniques known in the art.

The LINC complex plays a key role in premature ageing because (i) mutations in Lamin A are known to cause premature ageing diseases, such as Hutchison-Gilford Progeria Syndrome (HGPS), and (ii) modulating levels of SUN1 and Nesprin ameliorates progeria phenotypes both in vitro and in vivo. Thus, LINC complex biology can be harnessed to develop potent anti-ageing and regenerative medicine technologies.

Hence, in a sixth aspect, there is provided a method of identifying a skin-softening compound, the method comprising:

1. contacting, in the presence of a test compound, a SUN domain with a KASH domain; and
2. detecting binding between the SUN domain and the KASH domain, wherein an alteration in binding as compared to a control is an indicator that the test compound is a candidate skin-softening compound that disrupts a LINC complex comprising SUN domain and a KASH domain.

The alteration may be increased binding or reduced binding. Preferably, the alteration is increased binding between the SUN domain and the KASH domain, or reduced binding between the SUN domain and the KASH domain. The increased binding may be at least a 10%, 15%, 25%, 35%, 45%, 50%, 55%, 60%, 65%, 70%, 75%, 80%, 85%, 90%, 95%, or 100% increase. The reduced binding may be at least a 10%, 15%, 25%, 35%, 45%, 50%, 55%, 60%, 65%, 70%, 75%, 80%, 85%, 90%, 95% or 100% reduction.

The skilled person would appreciate that the binding of a SUN domain to a KASH domain may be detected using a variety of techniques known in the art, which include, but are not limited to, protein complex immunoprecipitation, Bimolecular Fluorescence complementation, Affinity electrophoresis, Immunoelectrophoresis, chemical cross linking, Proximity ligation assay and FRET.

In a seventh aspect, there is provided a method of making cells softer, the method comprising contacting a skin cell with an agent that disrupts the LINC complex.

The cells are made softer by at least 10%, 15%, 25%, 35%, 45%, 50%, 55%, 60%, 65%, 70%, 75%, 80%, 85%, 90%, 95%, 100%, 150%, 200% or 300% compared to the softness of the wild-type cells.

Advantageously, softening cells improves their ability to form cellular layers.

In an eighth aspect, there is provided use of an agent that disrupts the LINC complex in an anti-ageing skin composition.

Preferably, the agent does not disrupt a LINC complex comprising Nesprin-2. Most preferably, the agent disrupts a LINC complex comprising SUN1.

The use may comprise contacting the agent with a pharmaceutical acceptable vehicle.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents (i.e. the agent referred to in the first, third and fifth to seventh and eighth aspects) according to the invention. In tablets, the active compound may be mixed with a vehicle having the necessary compression properties in suitable proportions and compacted in the shape and size desired. The powders and tablets preferably contain up to 99% of the active compound. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The compound according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The compound may be prepared as a sterile solid composition that may be dissolved or suspended at the time of administration using sterile water, saline, or other appropriate sterile injectable medium.

The compound and compositions of the invention may be administered in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compounds used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The cell in the kit of the third aspect or the method of the seventh aspect may be a cell as defined in the method according to the first aspect. The agent in the kit of the third aspect or the method according to the seventh aspect may be an agent as defined according to the method of the first aspect.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the nucleic acids or polypeptides described herein.

Amino acid/polynucleotide/polypeptide sequences with a sequence identity which is greater than 50%, more preferably greater than 65%, 70%, 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90%, 92%, 95%, 97%, 98%, and most preferably at least 99% identity with any of the sequences referred to herein.

The skilled technician will appreciate how to calculate the percentage identity between two amino acid/polynucleotide/ polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on: (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula: Sequence Identity=(N/T)*100.

Alternative methods for identifying similar sequences will be known to those skilled in the art. For example, a substantially similar nucleotide sequence will be encoded by a sequence which hybridizes to any sequences referred to herein or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, to, 20, 50 or 100 amino acids from the polypeptide sequences described herein.

Due to the degeneracy of the genetic code, it is clear that any nucleic acid sequence described herein could be varied or changed without substantially affecting the sequence of the protein encoded thereby, to provide a variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

BRIEF DESCRIPTION OF THE DRAWINGS

For a better understanding of the invention, and to show how embodiments of the same may be carried into effect, reference will now be made, by way of example, to the accompanying Figures, in which:

In FIG. 4A the DN-SUNL subcellular distribution (GFP channel) is highlighted. Note the distinct nuclear rim (red arrowheads) and reticular pattern of DN-SUN1 in the cytosol (blue arrows), which corresponds to the endoplasmic reticulum (ER) membranes. DN-SUNL expression affects nuclear shape (white arrows) and yields blebs at the nuclear surface (white arrowheads). Scale bar=10 μm. FIG. 4B Statistical analysis (Student's t-test; P value<0.05 is indicated by *) demonstrates significant changes in nuclear morphology in DN-SUNL cells. Results are mean±standard deviation;

FIG. 5A Schematic representing the basic nesprin-2 giant domain architecture and the epitopes of three specific nesprin-2 antibodies (i.e. Nes2NT, Nes2K49 and Nes2CT). Lower panels depict an immunofluorescence analysis using nesprin-2 antibodies, which shows that DN-SUNL expression displaces all nesprin-2 isoforms from the nuclear envelope (arrows). These results highlight the dominant negative effects of the DN-SUNL construct on Nesprin-2. In contrast, control cells (asterisks) exhibit strong nesprin-2 nuclear staining. FIG. 5B DN-SUNL expression in fibroblasts shows that also endogenous nesprin-1 is efficiently displaced from the nucleus, while untransfected cells (asterisks) display pronounced nesprin-1 nuclear rim staining. FIG. 5C The expression of DN-SUNL affects specifically proteins of the KASH-domain family (i.e. nesprins) considering that the subcellular localisation of other key components of the nuclear envelope such as SUN1, emerin, LAP2β, and lamin A/C are largely unaffected. All scale bars=10 μm. Nuclei are visualised by DAPI staining (blue);

FIG. 6A Phase contrast and fluorescent staining's of nuclei (DAPI, blue) and the F-actin cytoskeleton (Phalloidin, red) of 70% confluent WT and DN HaCaT. Phalloidin denotes the cortical actin cytoskeleton in keratinocytes and therefore visualizes the cell boundaries. Scale bar=200 μm (phase contrast), and 20 μm (fluorescent panels). In contrast to DN cells, WT cells are flatter and less dense within the colonies; FIG. 6B DN HaCaT colonies contain twice as much cells compared to WT counterparts. Statistical analysis (Student's t-test; P value<0.05 is indicated by *) demonstrates a significant changes in the cell density of WT and DN-SUNL mutant colonies. Results are mean±standard deviation. FIG. 6C DN cells express higher E-cadherin levels compared to WT cells grown on 2D surfaces;

FIG. 7A WT and DN HaCaT cells 24 h post trypsinisation were examined using immunofluorescence. Cells are stained for DAPI (blue), phalloidin (cyan) and vinculin (red). Vinculin is a mechano-sensing protein that is enriched at peripheral cell-substratum contacts (termed focal contacts). Arrows display sites of focal adhesion formation across the cell periphery. Note that in contrast to DN cells, WT cells exhibit prominent enrichment of focal contacts at the cell periphery. Vinculin is diffusely distributed in DN cells. Scale bar=10 μm. FIG. 7B Western blotting indicating that vinculin levels are not perturbed in DN cells. The localization of vinculin changes upon LINC complex disruption but not the levels of the protein. B-actin and tubulin indicates equal protein loading. Anti-GFP immunoblotting demonstrates expression of dominant negative LINC complex interfering proteins in DN cells;

FIG. 8A Single and co-cultured (with dermal fibroblasts) DN HaCaT cells grown in 3D form prominent multi-layered structures when grown at the air-liquid interface that favours differentiation of keratinocytes. The black lines indicate the scaffold surface. H&E stained sections are shown. FIG. 8B Fluorescence examination of single-cultured DN cells verifies that cell stacking (arrows) is indeed occurring above rather than within the scaffold. The scaffold boundaries are visualized using Nile Red, while the existence of DN cells is denoted using GFP. Scale bars=25 μm. FIG. 8C Highlights that LINC disruption substantially favours the formation of epidermal-like (multi-layered cell assembly) tissue structures in vitro. Asterisks denote statistical significance (P value<0.05) using a Student's t-test;

FIG. 9A Fluorescence microscopic examination of single cultured WT and DN cells in 3D highlighting that DN HaCaT cells (GFP expressing) display shape changes similar to that found in skin. Note that WT cells grown on the surface of the scaffold (visualized with Nile Red) exhibit flattened nuclei (yellow arrows) whereas DN cells proximal to the scaffold surface (denoted by the white dotted line) display columnar shapes (asterisks). In skin, epithelial cell/nuclear flattening occurs only in differentiated cells. Therefore, DN cells at the scaffold/air interface mimic basal keratinocyte morphologies. In contrast, DN cells away from the scaffold surface exhibit pronounced cell flattening (white arrows) a feature common to terminally differentiated skin keratinocytes belonging to the spinous and granular layers of skin. FIG. 9B Immunofluorescence analysis of WT and DN cells co-cultured with human dermal fibroblast cells in 3D scaffolds for 8 days at the air-to-liquid interface. Two markers were examined; K14 (Keratin 14) is a marker for basal dividing keratinocytes, while K10 (Keratin 10) is a terminal differentiation marker, which is expressed by suprabasal keratinocytes in skin. Note that DN HaCaT's exhibit increased K10 expression, proper spatial arrangements and morphologies (namely flattening) at areas that are distal to the scaffold surface, which mimics the in vivo situation. Cells in proximity to the scaffold (dotted line) lack K10 staining. In contrast, WT cells exhibit sporadic K10 staining within the scaffold. Scale bars=25 nm;

FIG. 11A Phase contrast images of WT and DN-SUNL cells (top row). The position of the nuclei (white dotted lines) and nucleoli (purple dotted circles) is indicated. The corresponding atomic force microscopy (AFM) Young's modulus (kPa) analysis of the WT and DN-SUNL mutant colonies (middle row) and AFM height scans (μm; lower row) is shown. FIG. 11B Schematic diagram indicating three distinct cellular areas where AFM Young's modulus measurements were taken. FIG. 11C Histogram showing that across the three selected cellular areas that DN-SUNL are significantly softer compared to their WT counterparts (n=15 for each cell type). FIG. 11D Histogram depicting the highest cantilever surface indentation (μm) measured on WT and DN-SUNL cells using a cantilever force of 150 pN, indicates that DN cells are significantly more pliable compared to WT (n=35 for each cell type). Statistical analysis (Student's t test; P value<0.005 is indicated by **);

Figure 1:
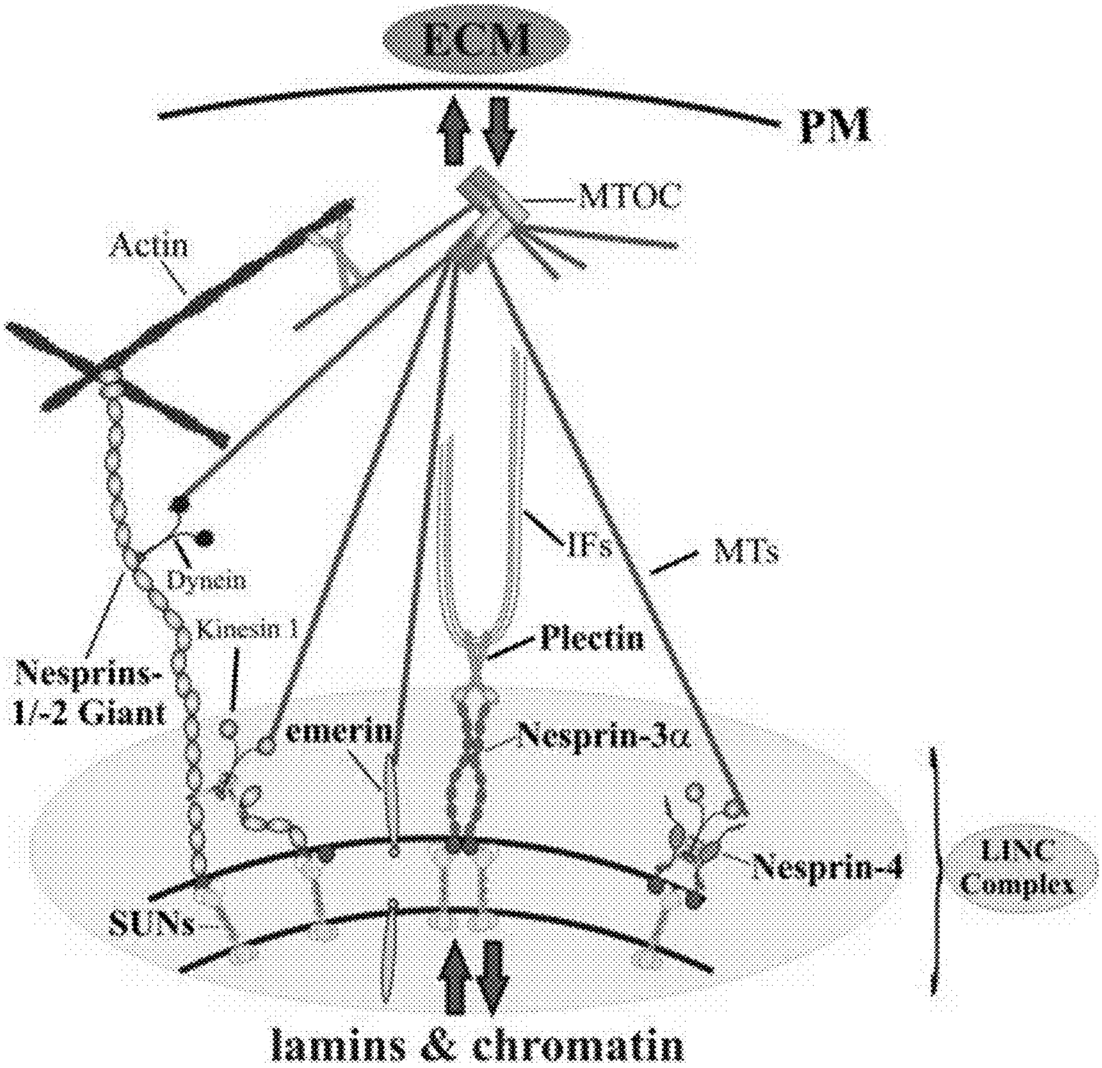
FIG. 1 is a schematic diagram, which shows that LINC complex is a conserved structure formed by Nesprin (i.e. nesprin-1, nesprin-2, nesprin-3 and nesprin-4) and SUN-domain proteins, which span the entire nuclear envelope and functionally link the nuclear interior (e.g. lamina, chromatin, telomeres, transcription factors) to the extracellular matrix (ECM) via associations to multiple cytoskeletal structures (e.g. microtubules [MTs], intermediate filaments [IFs], actin, dyneins, kinesins, Microtubule organising centre [MTOC]), cytolinker proteins (e.g. plectin) and plasma membrane [PM] receptors. High (termed giant) and low molecular weight Nesprin-1 and -2 isoforms are indicated. SUN-domain proteins are depicted as trimers.

Note that the DN-SUNL expressing cell (asterisk) displays a GFP signal at the ER (red arrows) and the NE (blue arrows), but lacks nuclear nesprin-2 staining (white arrows). In contrast SP-GFP expressing control cells or DN-SUNL untransfected cells exhibit strong nesprin-2 staining at the nucleus (yellow arrows). Nuclei are visualised by DAPI staining (blue). Scale bars=10 μm.

EXAMPLES

Cells of specific tissues have correspondingly specific properties, including biomechanical, biochemical and structural properties. Such specific properties are determined by signals received from the physical and biochemical environment surrounding the cell. The inventors have found that crucial intracellular signalling events occurs via a central "switch" (the LINC complex) that physically links, via the cytoskeleton, genetic material of a cell to the extracellular environment. As shown in the following examples, the inventors have interrupted the formation of the LINC complex using a construct that overexpresses a dominant negative SUN1 fusion protein (DN-SUNL). In doing so, the inventors have induced specific cellular properties without having to create a complex and highly specific external environment.

Materials and Methods

Plasmid Construction

All cloned fragments were sequenced in their entirety. pcDNA3.1 (-) (Invitrogen) was used to engineer the DN-SUNL and the specific control (SPGFP) constructs (see Schneider et al., 2011, Cell. Mol. Life Sci. 68:1593-1610). The DN-SUNL comprises torsin-A signal peptide (SP) sequence, sequences encoding GFP (Green Fluorescent Protein), the coiled-coil domain and the SUN-domain of a murine SUN1 protein (the SUN1 transgene protein lacks the N-terminal domain and the transmembrane domain). The full polypeptide sequence (819 amino acids) of one embodiment of the DN-SUNL is provided herein as SEQ ID No. 28 (previously referred to as SEQ ID No. 40 in patent application GB1701438.2), as follows:

```
                                          [SEQ ID No. 28]
MKLGRAVLGLLLLAPSVVQAVASVSKGEELFTGVVPILVELDGDVNGHKF

SVSGEGEGDATYGKLTLKFICTTGKLPVPWPTLVTTLTYGVQCFSRYPDH

MKQHDFFKSAMPEGYVQERTIFFKDDGNYKTRAEVKFEGDTLVNRIELKG

IDFKEDGNILGHKLEYNYNSHNVYIMADKQKNGIKVNFKIRHNIEDGSVQ

LADHYQQNTPIGDGPVLLPDNHYLSTQSALSKDPNEKRDHMVLLEFVTAA

GITLGMDELYKEFVSLWGQGNFFSLLPVLNWTAMQPTQRVDDSKGMHRPG

PLPPSPPPKVDHKASQWPQESDMGQKVASLSAQCHNHDERLAELTVLLQK

LQIRVDQVDDGREGLSLWVKNVVGQHLQEMGTIEPPDAKTDFMTFHHDHE

VRLSNLEDVLRKLTEKSEAIQKELEETKLKAGSRDEEQPLLDRVQHLELE

LNLLKSQLSDWQHLKTSCEQAGARIQETVQLMFSEDQQGGSLEWLLEKLS

SRFVSKDELQVLLHDLELKLLQNITHHITVTGQAPTSEAIVSAVNQAGIS

GITEAQAHIIVNNALKLYSQDKTGMVDFALESGGGSILSTRCSETYETKT

ALLSLFGVPLWYFSQSPRVVIQPDIYPGNCWAFKGSQGYLVVRLSMKIYP

TTFTMEHIPKTLSPTGNISSAPKDFAVYGLETEYQEEGQPLGRFTYDQEG

DSLQMFHTLERPDQAFQIVELRVLSNWGHPEYTCLYRFRVHGEPIQ
```

Thus, in one embodiment, the agent according to any aspect of the invention may comprise an amino acid sequence substantially as set out in SEQ ID No. 28, or a variant or fragment thereof.

The signal peptide has been included to ensure that the DN-SUNL peptide is transported to the endoplasmic reticulum and/or the nuclear envelope. The polypeptide sequence of the torsin-A signal peptide (SP) sequence used in the DN-SUNL is provided herein as SEQ ID No. 29 (previously referred to as SEQ ID No. 41 in patent application GB1701438.2), as follows:

[SEQ ID No. 29]
MKLGRAVLGLLLLAPSVVQAV

The GFP protein has been included to ensure that the DN-SUNL peptide can be visualised under UV light. The polypeptide sequence of the GFP protein used in the DN-SUNL is provided herein as SEQ ID No. 30 (previously referred to as SEQ ID No. 42 in patent application GB1701438.2), as follows:

[SEQ ID No. 30]
SKGEELFTGVVPILVELDGDVNGHKFSVSGEGEGDATYGKLTLKFICTTG
KLPVPWPTLVTTLTYGVQCFSRYPDHMKQHDFFKSAMPEGYVQERTIFFK
DDGNYKTRAEVKFEGDTLVNRIELKGIDFKEDGNILGHKLEYNYNSHNVY
IMADKQKNGIKVNFKIRHNIEDGSVQLADHYQQNTPIGDGPVLLPDNHYL
STQSALSKDPNEKRDHMVLLEFVTAAGITLGMDELYK

The polypeptide sequence of the murine C-terminal SUN1 luminal protein used in the DN-SUNL is provided herein as SEQ ID No. 31 (previously referred to as SEQ ID No. 43 in patent application GB1701438.2), as follows:

[SEQ ID No. 31]
VSLWGQGNFFSLLPVLNWTAMQPTQRVDDSKGMHRPGPLPPSPPPKVDHK
ASQWPQESDMGQKVASLSAQCHNHDERLAELTVLLQKLQIRVDQVDDGRE
GLSLWVKNVVGQHLQEMGTIEPPDAKTDFMTFHHDHEVRLSNLEDVLRKL
TEKSEAIQKELEETKLKAGSRDEEQPLLDRVQHLELELNLLKSQLSDWQH
LKTSCEQAGARIQETVQLMFSEDQQGGSLEWLLEKLSSRFVSKDELQVLL
HDLELKLLQNITHHITVTGQAPTSEAIVSAVNQAGISGITEAQAHIIVNN
ALKLYSQDKTGMVDFALESGGGSILSTRCSETYETKTALLSLFGVPLWYF
SQSPRVVIQPDIYPGNCWAFKGSQGYLVVRLSMKIYPTTFTMEHIPKTLS
PTGNISSAPKDFAVYGLETEYQEEGQPLGRFTYDQEGDSLQMFHTLERPD
QAFQIVELRVLSNWGHPEYTCLYRFRVHGEPIQ 2D and 3D Cell Culture WT and DN-SUNL HaCaT, NIH-3T3 and primary human dermal fibroblast (HDF; LifeTechnologies) cells were cultured at 37° C., 5% CO2 in Dulbecco's Modified Eagles Medium, high glucose supplemented with 10% fetal calf serum, 2 mM penicillin, and 2 mM streptomycin (Sigma). For the cultivation of stable transfected DN-SUNL HaCaT cells, 0.5 mg/ml G418 disulphate (Sigma) was added to the media solution. 2D cell culture was performed on conventional poly-styrene flasks, 10 cm petri-dishes and 12/24 well dishes. For 3D culture, 12-well Alvetex® Strata inserts (Reinnervate) were employed. Materials were pre-treated with oxygen plasma for 5 min at 40 W using an Emitech K1050X Plasma Asher.

To seed the cells to Alvetex® Strata, 100 µl of WT or DN-SUNL HaCaT cell suspension containing 250,000 cells each was applied directly to the centre of each pre-treated scaffold. The scaffolds were then placed in their respective culture dishes and moved into a cell culture incubator for 20 min to allow cell attachment to the scaffold surface. Complete culture media was added. For the co-culture observations, 500,000 HDF cells at a T-75 confluence of 60% were placed onto plasma-treated scaffolds alongside complete culture medium and cultured in 12 well plates for 7 days. The scaffolds were transferred into 6 well plates containing 4 mL complete culture media and were cultured for a further 7 days. Either WT or DN HaCaT cells were then seeded. After the seeding of 250,000 keratinocytes (applies for both single or co-culture experiments) the cells were grown submerged in media for 4 days, before the cells were grown at the air-liquid interface for another 8 days.

Paraffin Embedding and Immunofluorescence Microscopy 3D cell cultures were rinsed once with cell culture grade phosphate-buffered saline (PBS) and carefully unclipped from the insert holder. Upon removal, scaffolds were washed a further two times in PBS for 5 min, submerged within 4% paraformaldehyde (PFA) in PBS, pH 7.4 and left at 4° C. overnight. After fixation, scaffolds were washed another two times in PBS for 5 minutes each. Washing was then followed by 15 min incubations in varying ethanol concentrations of 30%, 50%, 70%, 80%, 90%, 95% and 100% v/v at room temperature. Scaffolds were subsequently removed from their housing inserts, cut in half across their diameter using sterilised surgical scissors and incubated for 15 min in Histoclear (Fisher, 12358637) at 60° C. An equal volume of liquid paraffin wax (Fisher, 12624077) was added, and the scaffolds were incubated for 15 min at 60° C. The Histoclear/liquid paraffin solution was then replaced with fresh paraffin wax, and the scaffolds were incubated for 1 h at 60° C. Vertical embedding was then performed in which the scaffold sections were placed into embedding moulds (Cellpath Ltd, GAD-5302-02A) with the cut side facing down. These were then topped with a labelled embedding cassette (SLS, HIS0029), and filled with fresh paraffin wax. The resulting wax blocks were sectioned using a Leica RM2125RT microtome with MB Dynasharp microtome blades (Fisher, 12056679). For all cell lines, sections were cut to a thickness of 10 µm for conventional haematoxylin and eosin (H&E) staining, with subsequent 7 µm sections for antibody staining. Sections were then floated on a 42° C. water bath, mounted onto Superfrost+ microscope slides (Fisher, 10149870) and left to dry overnight on a 32° C. heated slide dryer. Sections were subsequently deparaffinised in Histoclear and hydrated through a series of 5 min incubations in 100%, 70% ethanol and PBS. Antigen retrieval was performed using microwave heating; samples were heated three times 5 min in citrate buffer, with cooling at RT for 30 sec between each heat treatment. Sections were cooled, treated with permeabilisation/blocking solution (20% normal goat serum [Sigma] in 0.4% Triton X-100 PBS) for 45 min before processing for indirect immunostaining.

2D cell cultures were fixed in 4% paraformaldehyde/PBS for 15 min and permeabilized in 0.5% Triton X-100/PBS for 10 min before the samples were processed for indirect immunostaining. Focal adhesion sites were identified through vinculin staining, scaffolds were counterstained with NILE red (Sigma, nuclei were stained with 4,6-diamino-2-phenylindone (DAPI; Sigma) and F-actin with TRITC-Phalloidin (Sigma). All indirect immunofluorescence samples were analysed by confocal laser-scanning microscopy using a TCS-SPS (Leica).

Antibodies

Primary antibodies used were directed against the C-terminus of nesprin-1 (specII), the N-terminus of Nesprin-2 (Nes2NT) mAb K56-386 [Luke et al., 2008, J. Cell Sci. 121, 1887-1898] and mAb K20-478 [Zhen et al., 2001, J. Cell Sci. 115, 3207-3222], the C-terminus of Nesprin-2 (Nes2CT) pAb Ki [Libotte et al., 2005, Mol. Biol. Cell 16, 3411-3424], β-actin mAb AC-74 (Sigma), GFP mAb K3-184-2 [Schneider et al., 2011, Cell. Mol. Life Sci.

68:1593-1610], Sun1 (Padmakumar et al., 2005, J. Cell Sci. 118, 3419-3430), lamin A/C (Jol2), tubulin mAb WA3 (kind gift from Dr. U. Euteneuer), vinculin mAb V9131 (Sigma), E-Cadherin rtAb U3254(Sigma), keratinio rbAb 76318 (Abcam) and keratin14 mAb 7800 (Abcam). For indirect immunofluorescence studies, Alexa 488, Alexa 568, and Alexa 647 fluorescently conjugated secondary antibodies (Invitrogen) were utilized. Peroxidase-coupled secondary antibodies (Sigma) were adopted in Western blot analysis.

H&E Histochemistry

Paraffin wax was cleared from the superfrost microscopy 3D scaffold-containing slides by washing with Histoclear for 5 min at room temperature. Gradual sample rehydration was conducted through washes in 100% ethanol for 2 min, 95% and 70% ethanol for 1 min, and distilled water for a further 1 min. Nuclei were then stained via a 5 minute incubation in Mayer's haematoxylin (Sigma, H1532) (0.1% v/v haematoxylin, 0.02% v/v sodium iodate, 5% v/v aluminium potassium sulphate, 5% v/v chloral hydrate and 0.1% v/v citric acid in $dH_2O$), followed by a 1 min wash in distilled water and incubation in alkaline alcohol (3% ammonia in 70% ethanol) for 30 sec to stain nuclei. Samples were subsequently dehydrated by 30 sec incubations in 70% and 95% ethanol. Once dehydrated, cytoplasmic staining in 0.5% eosin (Sigma, E4009) in 95% ethanol for min was carried out. The samples then underwent two 10 sec washes in 95% ethanol, followed by two washes in 100% ethanol, the first for 15 sec and second for 30 sec. Slides were then cleared via 2×3 min washes in Histoclear, prior to mounting with DPX mounting media (Fisher, 10050080) and covering with a 50×22 mm coverslip (Fisher, 12383138). Slides were left to dry at 4° C. overnight and then imaged using a Leica DM500 light microscope with attached ICC50 HD camera at 10× and 20× magnifications utilising the LAS EZ software (Leica).

Western Blotting

Protein lysate preparation from 2D cultured dishes is covered in detail in Carthew and Karakesisoglou (2016; Methods Mol Biol. 2016; 1411: 221-32). To extract protein lysates from 3D cultured cells, scaffolds were washed three times in PBS, removed from their housing inserts and cut into small (~1 mm), square pieces with sterilised scissors. Scaffold sections were then incubated in 500 μl RIPA [50 mM Tris/HCl (pH 7.5), 150 mM NaCl, 1% Nonidet-P40, 0.5% sodium desoxycholate] buffer supplemented with 1% protease inhibitor cocktail (Sigma) for 15 min at 4° C., during which sonication every 3 min for 30 sec was performed using an MSE soniprep 150 sonicator. The scaffold/cell suspension was centrifuged at 4° C. for 15 min at 12 000×g to pellet the remaining cell/scaffold debris, with resulting supernatant extracted, combined with 120 μl of 5× concentrated Laemmli sample buffer and boiled at 99° C. for 4 min. Samples were then stored at −20° C. until use.

Selective Permeabilisation and Proteinase Digestions to Elucidate the SP-GFP and DN-SUNL Subcellular Distribution Transiently transfected HaCaT cells that were transiently transfected with the SP-GFP and DN-SUNL transgenes were washed twice with ice-cold PBS buffer once the cell culture plates reached 60-70% confluency. Cells were collected from the plates using a cell scraper, transferred to a centrifuge tube and subjected to a 5 min centrifugation at 1,000 g. The supernatants were carefully removed and the cell pellets were re-suspended in either ice-cold hypotonic buffer [10 mM HEPES (pH 7.5), 1.5 mM KCl, 1.5 mM MgCl2, and 0.5 mM dithiothreitol] or protease inhibitor-containing (Roche) RIPA lysis buffer [50 mM Tris/HCl (pH 7.5), 150 mM NaCl, 1% Nonidet-P40, 0.5% sodium desoxycholate]. The former cell homogenate's were supplemented with either 5 μg/ml digitonin or 1% Triton X-100, incubated on ice for 4 min before the addition of proteinase K (5 μg/ml). After a 30 min incubation on ice the proteinase K-mediated digestion was terminated using 10 μg/ml phenylsulfonyl fluoride (PMSF). The digested samples were subjected to a 20 min centrifugation at 12,000 g and the supernatants were supplemented with Laemmli sample buffer. The RIPA-containing cell homogenates were incubated on ice for 15 min, centrifuged at 12,000 g, and the supernatants were mixed with sample buffer. All cell extracts were passed at least 20 times through a 27-gauge needle, before the lysates were analysed by SDS-PAGE, and Western blotting.

Transmission Electron Microscopy 2D cultured cells were fixed though 30 min incubations in 2% glutaraldehyde diluted in NaHCa buffer, washed two times in NaHCa buffer and incubated for 15 min in a solution of 1% tannic acid and 0.075% saponin at RT. Cells were then rinsed two times in NaHCa buffer, followed by two further washes in 0.1 M cacodylate buffer and transferred to a 1.5 ml centrifuge tube. Cell suspensions were centrifuged at 1000 g for 4 min, with resulting pellet incubated for 1 h in a solution of 0.5% osmium tetroxide in 0.1 M cacodylate buffer. Pellets were further washed twice in 0.1 M cacodylate buffer, dehydrated through three 5 min washes in 50%, 70%, 95% and 100% ethanol solutions, and infiltrated two times with a 1:1 mixture of 100% alcohol and propylene oxide for 10 min. Cells were then incubated in a 1:1 mixture of propylene oxide and epoxy resin (EPON™ 828) at 60° C., twice in 100% epoxy resin at 60° C. for 30 min, and finally in fresh epoxy resin at 60° C. for 24-48 h to allow polymerisation. Ultra-thin sections were cut to 70 nm using a Leica EM UC6, and mounted onto Formvar coated copper grids. Grids were incubated in uranyl acetate for 10 min, rinsed twice in distilled water, and further incubated in lead citrate (0.4% lead citrate w/v, 0.5% sodium citrate in 0.1 N NaOH) for 10 mins. Subsequent image acquisition was performed using a Hitachi TEM-H7600 transmission electron microscope.

Atomic Force Microscopy

Cells were cultured to a confluence of 60% on 35 mm plastic petri dishes (TPP). 30 min before analysis, extensively PBS-washed cultures were placed into sterile filtered, CO2 independent culture media (Fisher). Subsequent examination was conducted using a Nanowizard® 3 Bioscience atomic force microscope (JPK) using a (D)NP silicon nitride probe cantilever, expressing a spring constant of 0.06-0.7 N/m (Bruker, DNP-10) over a 15×15 μm grid. Cells were maintained at a constant temperature of 37° C. throughout image collection. Young's modulus values were generated using the Gwyddion image analysis software.

Statistical Analysis

Statistical analysis was performed using Student's t test; 300 cells were used for every data set unless otherwise stated. Results were shown as mean±SD. P values of <0.05 were considered significant. The mean±SEM cell stacking from the 3D cell culture experiments and all the 2D morphometrics data sets were measured using the processing software ImageJ (v1.49).

Example 1—Components of the LINC Complex

The LINC complex is widely recognised as the major nuclear envelope (NE) component able to provide the mechanical links between the nucleus and cytoskeletal network, comprising an outer nuclear membrane (ONM)

Figure 2:
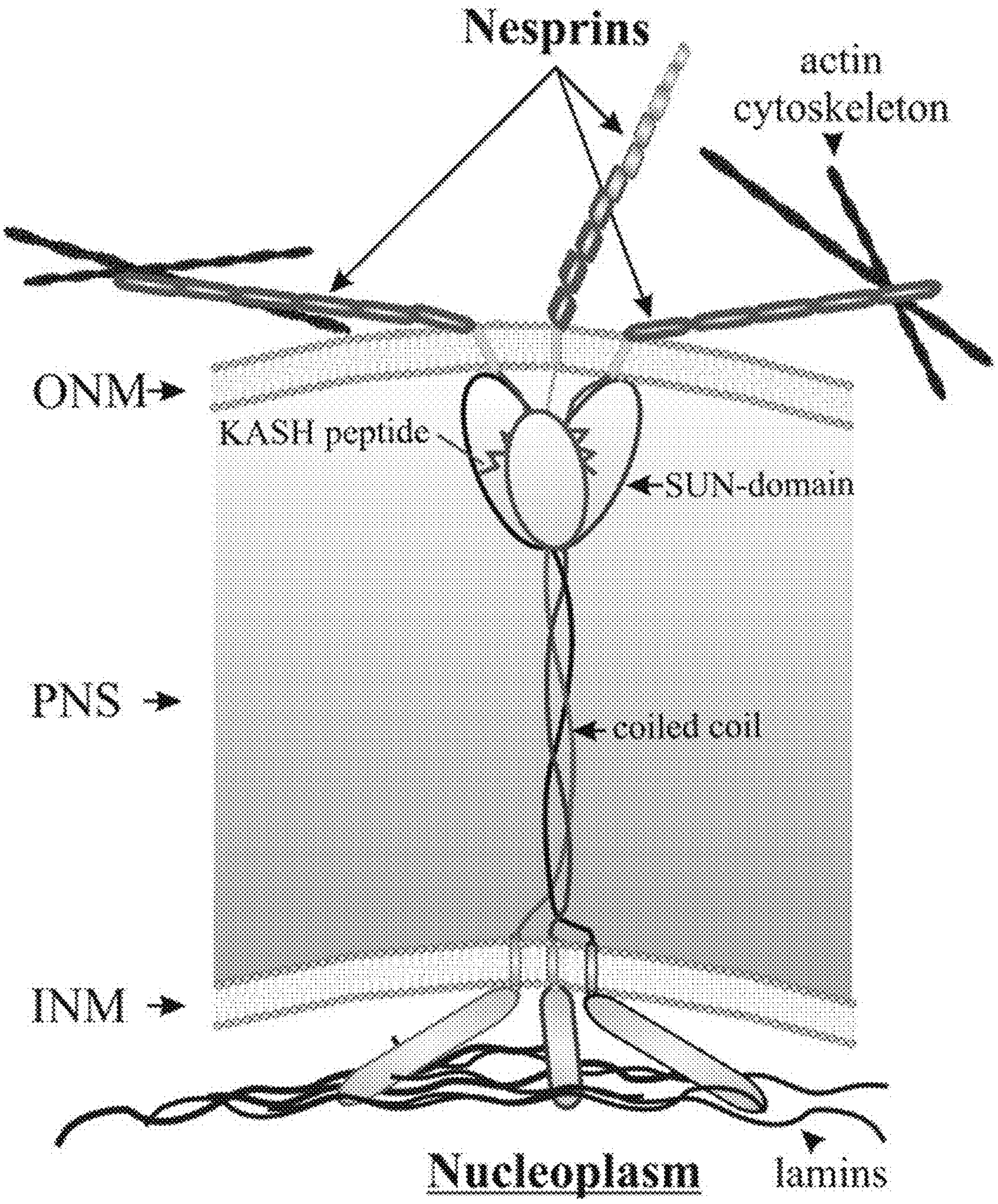
FIG. 2 is a schematic diagram of the LINC complex bridge across the nuclear envelope. The LINC complex bridge comprises SUN and KASH interactions within the perinuclear space alongside associated cytoskeletal and nucleoskeletal networks. ONM: outer nuclear membrane, INM: inner nuclear membrane, PNS: perinuclear space.

KASH domain proteins and inner nuclear membrane (INM) SUN proteins (see FIGS. 1 and 2). The KASH domain projects into the NE lumen, where it interacts with SUN domains. This SUN-KASH interaction helps to anchor KASH proteins to the NE, preventing them from diffusing into the adjoining endoplasmic reticulum (ER). The ONM KASH proteins interact with a range of cytoskeletal components, and thus, physically tether the nucleus to the cytoplasmic compartment, whereas the SUN proteins physically interact with INM proteins networks, such as the nuclear lamina and chromatin components. This complex of proteins therefore establishes a physical bridge between the cytoskeletal and nucleoskeletal networks. The formation of this two-membrane adhesive assembly of proteins is capable of transmitting force across the NE, providing function in maintaining centrosome-nuclear interactions, nuclear architecture, signal transduction, DNA repair and chromosome migration. This therefore suggests that the LINC complex must be a dynamic protein network of highly ordered protein interactions, allowing the transmission of multiple signal transductions from a variety of cytoskeletal components to the nuclear interior.

Example 2—SUN1 Luminal Domain Dominant Negative Construct (DN-SUNL)

Figure 3:
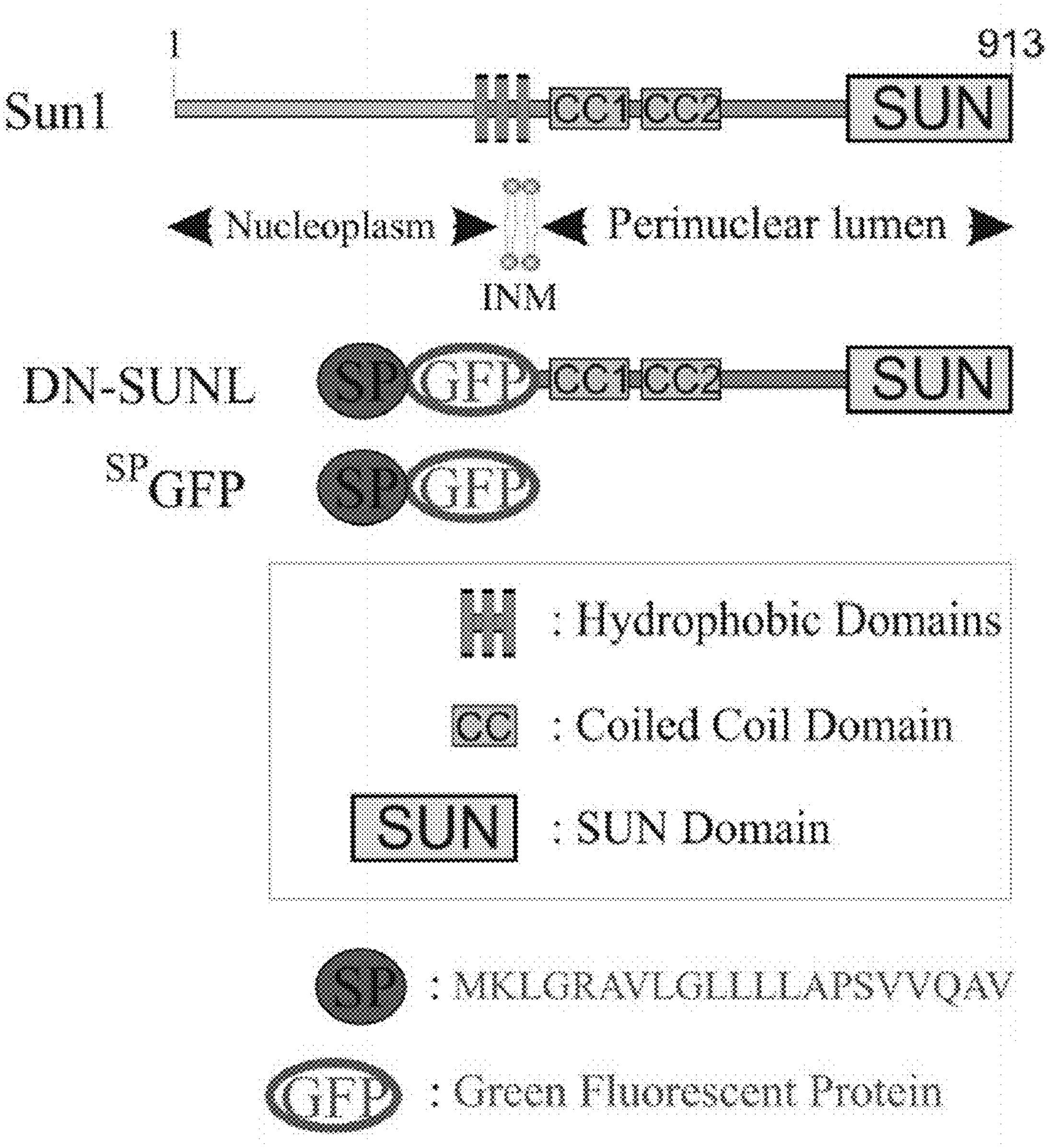
FIG. 3 is a schematic diagram of the DN-SUNL construct, which encodes a dominant negative SUN1 luminal domain in relation to the full-length Sun1 protein. Major Sun1 protein domains and topologies within the nuclear envelope are indicated. The truncated SUN1 protein (lacks the N-terminus, which is found in the nucleoplasm, and the three hydrophobic domains) is fused to the Torsin A signal peptide (SEQ ID NO:29) (SP; the amino acid sequence is given), GFP (green fluorescent protein) and expressed in the endoplasmic reticulum (ER) and nuclear envelope lumen (Schneider et al., 2011, Cell. Mol. Life Sci. 68:1593-1610) where it binds and saturates all KASH-protein binding sites (see FIGS. 10A-10C for more details). Due to these associations all endogenous full-length KASH-proteins are dislodged from the nuclear envelope (hence dominant negative). SP-GFP is the relevant control (Schneider et al., 2011, Cell. Mol. Life Sci. 68:1593-1610) that lacks the SUN1 N-terminal nucleoplasmic and C-terminal luminal sequences but harbours the signal peptide sequences.
Figure 4A:
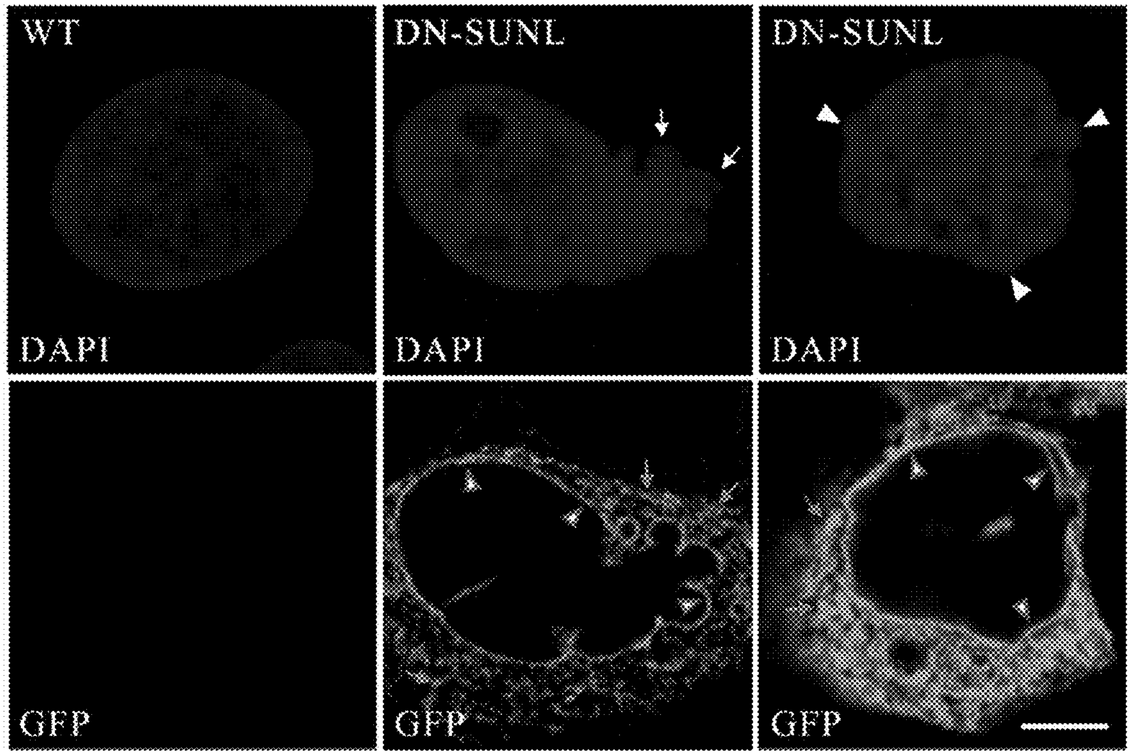
FIGS. 4A-4B are an indirect immunofluorescence analysis of wild type (WT) and DN-DUNL transiently transfected HaCaT cells that were counterstained with DAPI (blue) to stain nuclei.
Figure 4B:
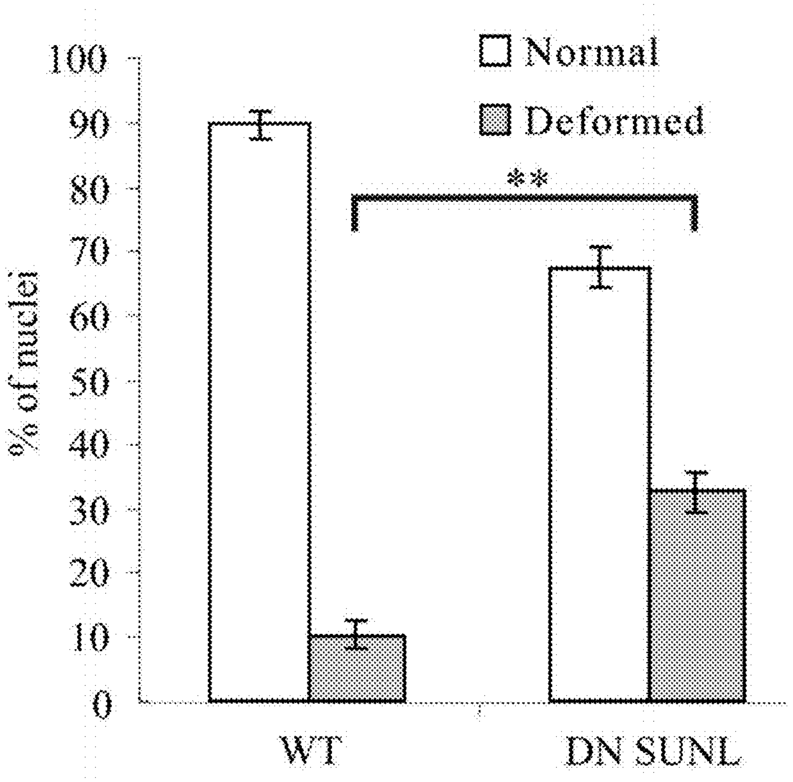
Figure 5A:
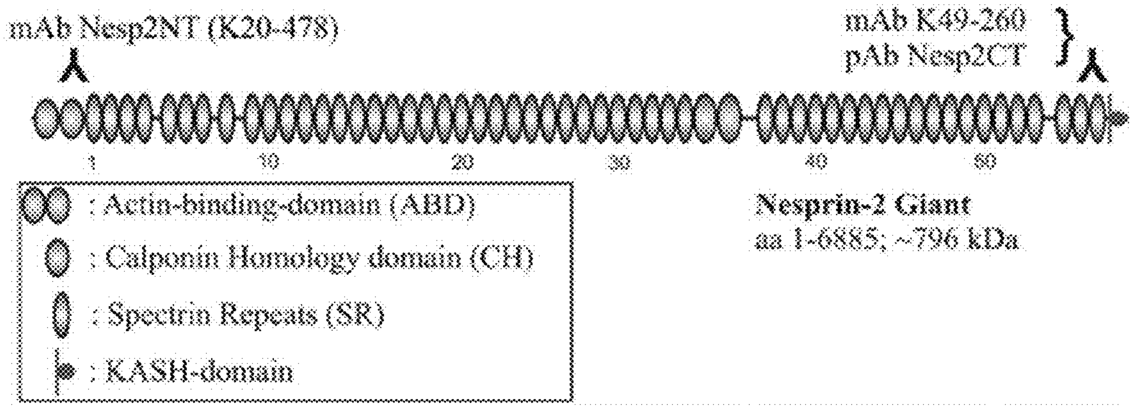
FIGS. 5A-5C are an indirect immunofluorescence analysis of DN-DUNL (transient transfection) expressing HaCaT (FIGS. 5A, 5C) and human dermal fibroblast cells (FIG. 5B).
Figure 5B:
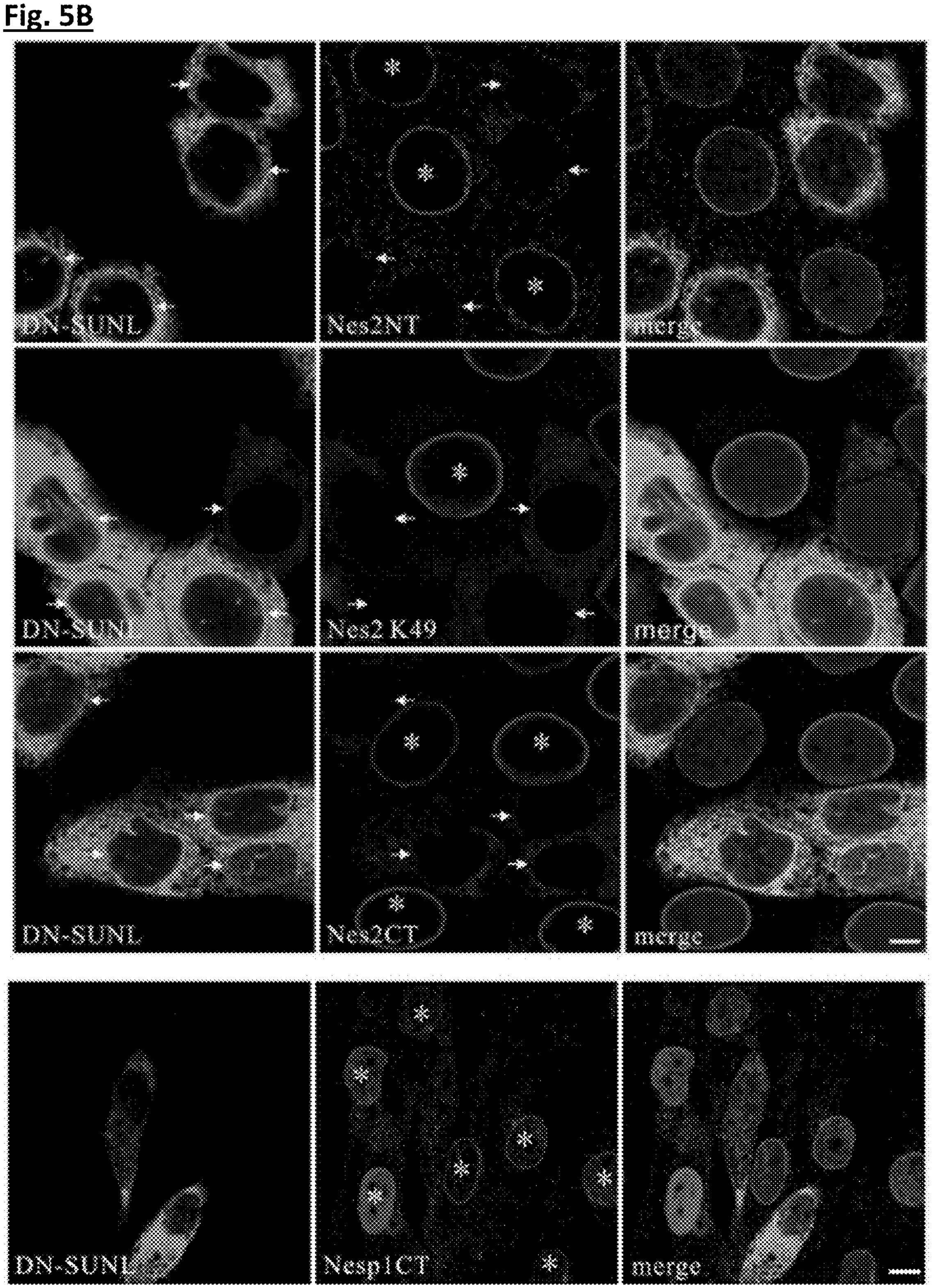
Figure 5C:
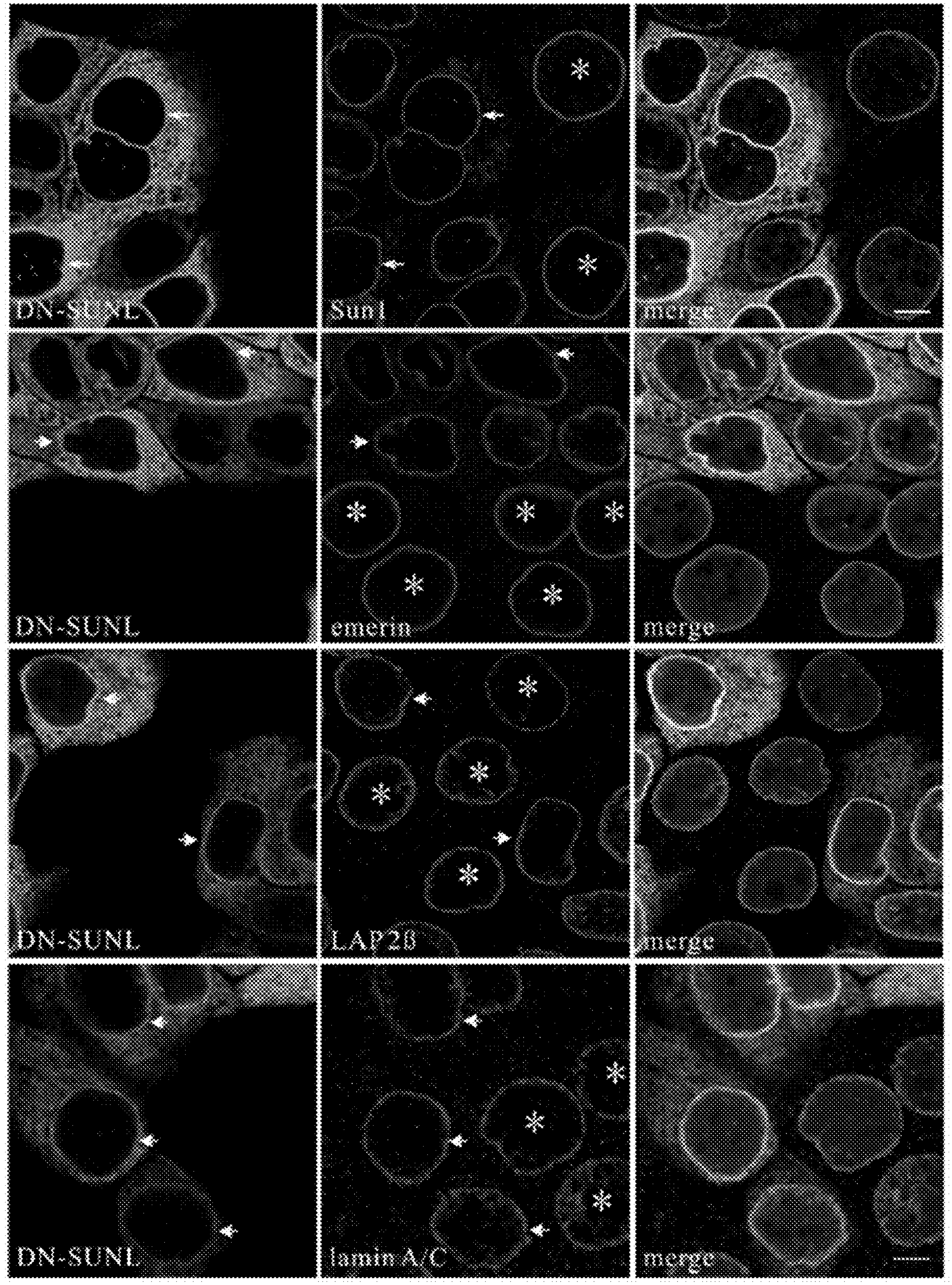

In order to study the role that the LINC complex protein, SUN1, plays in cellular structure and function, the inventors developed a construct (see FIG. 3) that encodes and overexpresses a fusion protein comprising a GFP-tagged luminal domain of SUN1 attached to an ER signal peptide (SP). The signal peptide was incorporated to ensure the fusion protein is overexpressed in the endoplasmic reticulum (ER) and the perinuclear space. To confirm that the fusion protein had translocated into the ER lumen and the perinuclear space, cell homogenates of HaCaT keratinocytes were subjected to proteinase K degradation in the presence of Triton X-100 or digitonin (see FIG. 12). In contrast to Triton X-100, which permeabilizes all biological membranes, low concentrations of digitonin leave the internal ER (endoplasmic reticulum) and NE (nuclear envelope) membranes unperturbed. Digitonin permeabilizes only cholesterol-rich membranes (i.e. plasma membrane). Similar to the ER and perinuclear space resident disulphide isomerase (PDI) protein, the SPGFP and DN-SUNL molecules were susceptible to proteinase K degradation only when cell homogenates were permeabilized with Triton X-100 (see FIG. 12). FIGS. 4A-4B and FIGS. 5A-5C show that the GFP-fusion DN-SUNL protein is expressed in the ER and the nuclear envelope.

Example 3—SUN1 Interacts with Nesprin-1 and Nesprin-2

Figure 7A:
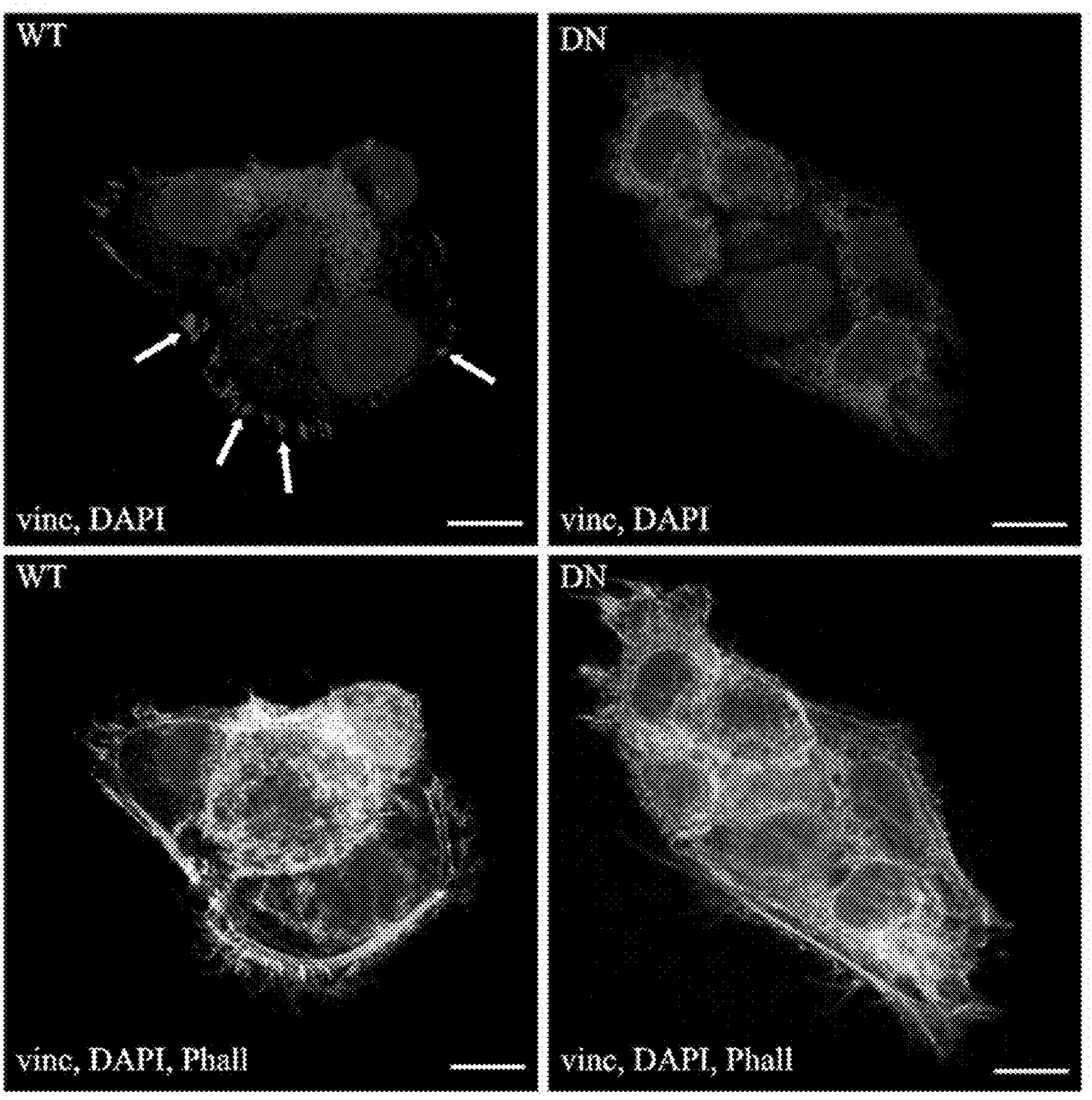
FIGS. 7A-7B are an analysis, which shows LINC complex disruption affects cell-to-substrate adhesion on 2D substrates.
Figure 7B:
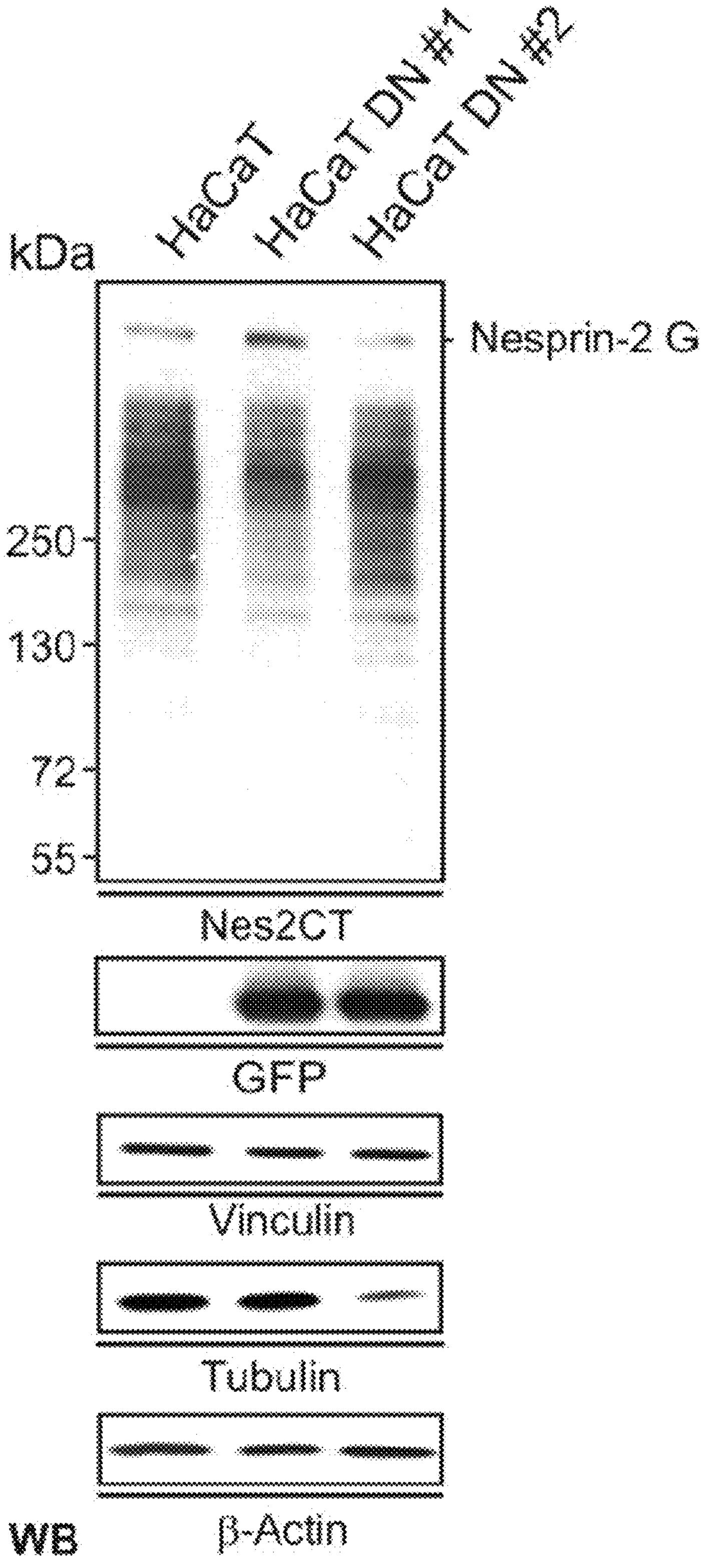
Figure 12:
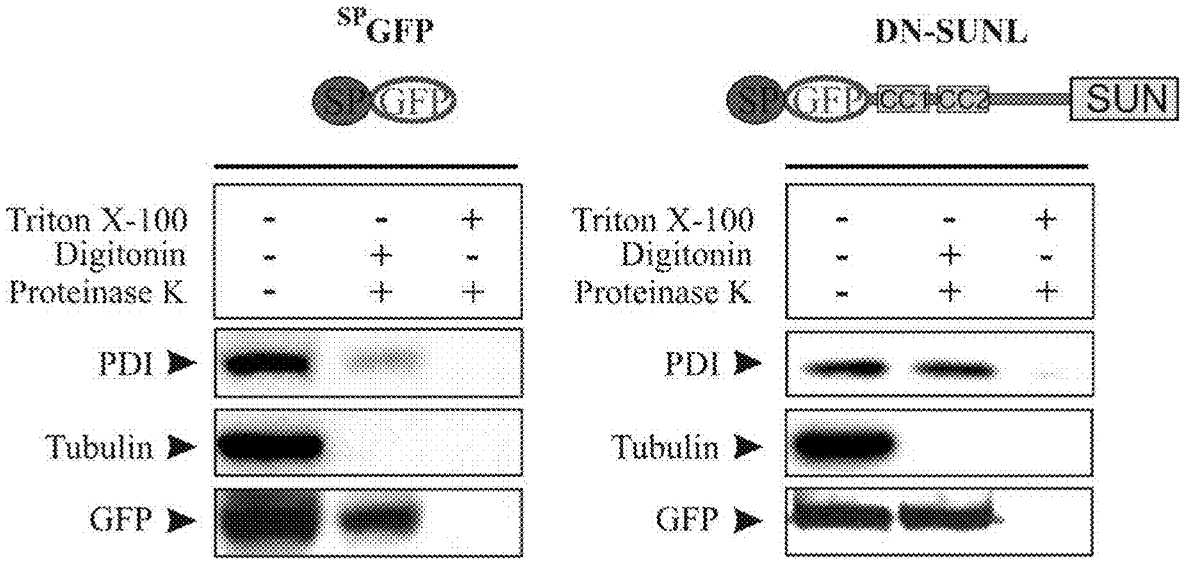
FIG. 12 is a Western blot analysis of HaCaT cells that have been transiently transfected with either SPGFP or DN-SUNL encoding plasmids. Three different experimental conditions were examined. Prior to Western blotting the cell homogenates were either left untreated (positive control) or treated with two different detergents: digitonin or Triton X-100 in the presence of the proteinase K enzyme. Digitonin permeabilises selectively the plasma membrane but leaves the ER and NE membranes intact. In contrast, Triton X-100 permeabilises all cellular membranes including the ER and the NE. Note that the GFP fusions and ER-lumen resident PDI (protein disulphate isomerase; control) proteins are detectable in the digitonin-treated samples but are completely absent in the Triton X-100-treated samples. Tubulin acts as a control for the cytoplasmic compartment, which is digested irrespectively of the detergents used.
Figure 13:
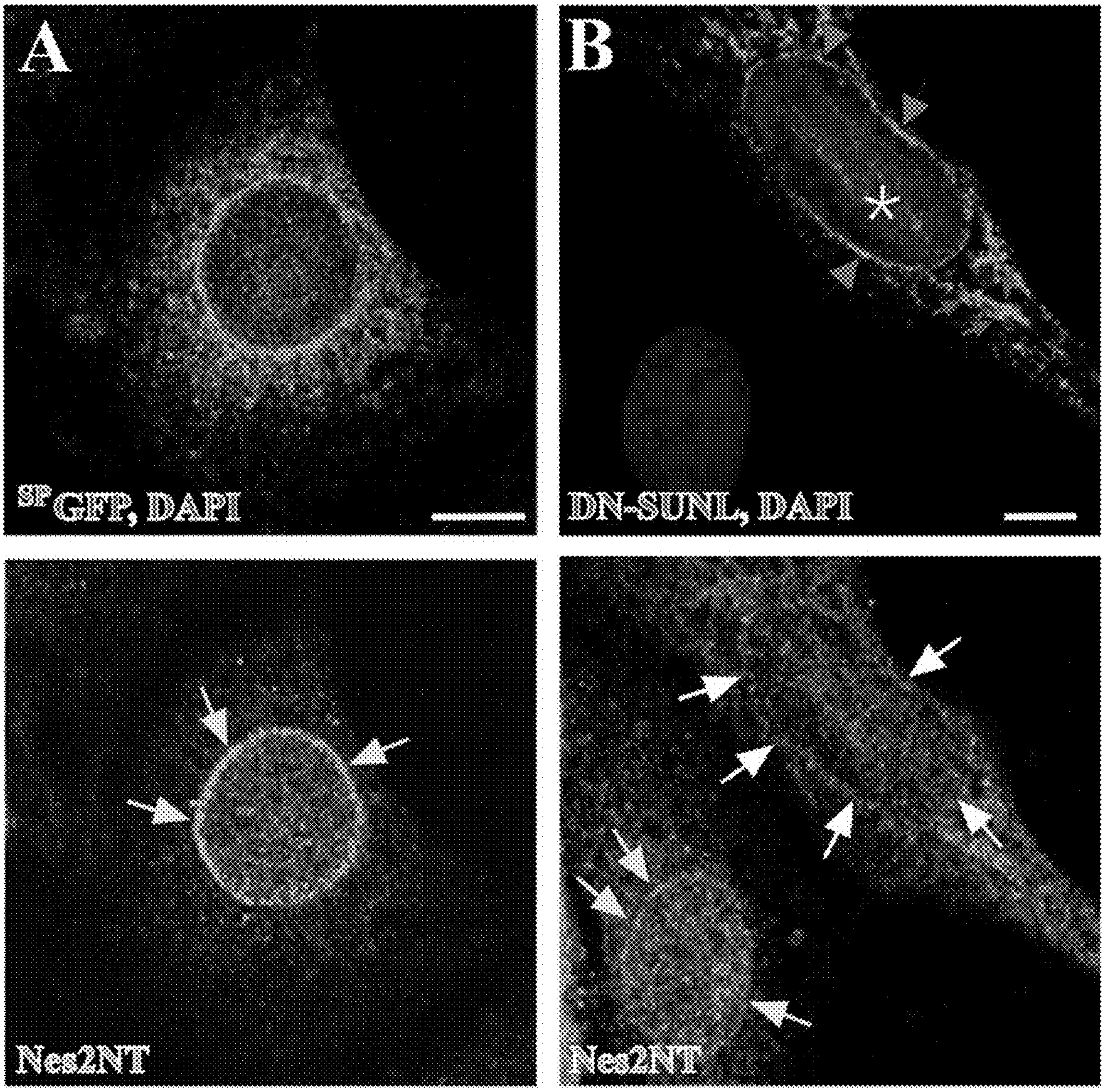
FIGS. 13A-13B are an indirect immunofluorescence analysis of SP-GFP (FIG. 13A) or DN-DUNL (FIG. 13B) transiently transfected NIH-3T3 fibroblasts using anti-Nesprin-2 giant (Nes2NT) antibodies, which shows the dominant negative effects of the DN-SUNL construct on the KASH-domain containing Nesprin-2 giant isoform.

The inventors elucidated the involvement of luminal KASH/SUN protein interactions with Nesprin-1 and Nesprin-2, the cytoplasmic binding partners of SUN1. Transiently transfected control DN-SUNL HaCaT and fibroblasts were immunostained for Nesprins-1 and Nesprin-2, respectively. Their decision to use these particular cellular models was based on the prevalence of Nesprin-1 and Nesprin-2 C-terminal KASH-domain isoforms (i.e. nuclear envelope associated isoforms) in fibroblasts and keratinocytes. In sharp contrast to untransfected cells (see FIGS. 5A and 5B asterisks), the DN-SUNL expression (see green panels in FIGS. 5A and 5B, arrows) dislodged Nesprin-1 and Nesprin-2 from the NE (see red panels in FIGS. 5A and 5B, arrows). Importantly, the localisation of other key nuclear proteins including SUN1 (FIG. 5C) and the Nesprin-2, vinculin, tubulin, and actin expression levels remained unaffected by DN-SUNL expression (FIG. 7B). Furthermore, in contrast to DN-SUNL, SP-GFP (control) does not affect the localisation of endogenous Nesprin-2. This highlights, that the SUN1 C-terminal sequences exert the dominant negative effects on KASH-domain proteins and not the SP and GFP segments of DN-SUNL (FIGS. 13A-13B), considering that both (SP-GFP and DN-SUNL) are expressed in the same membrane-bound compartments (i.e. ER and NE; FIG. 12).

Figure 6A:
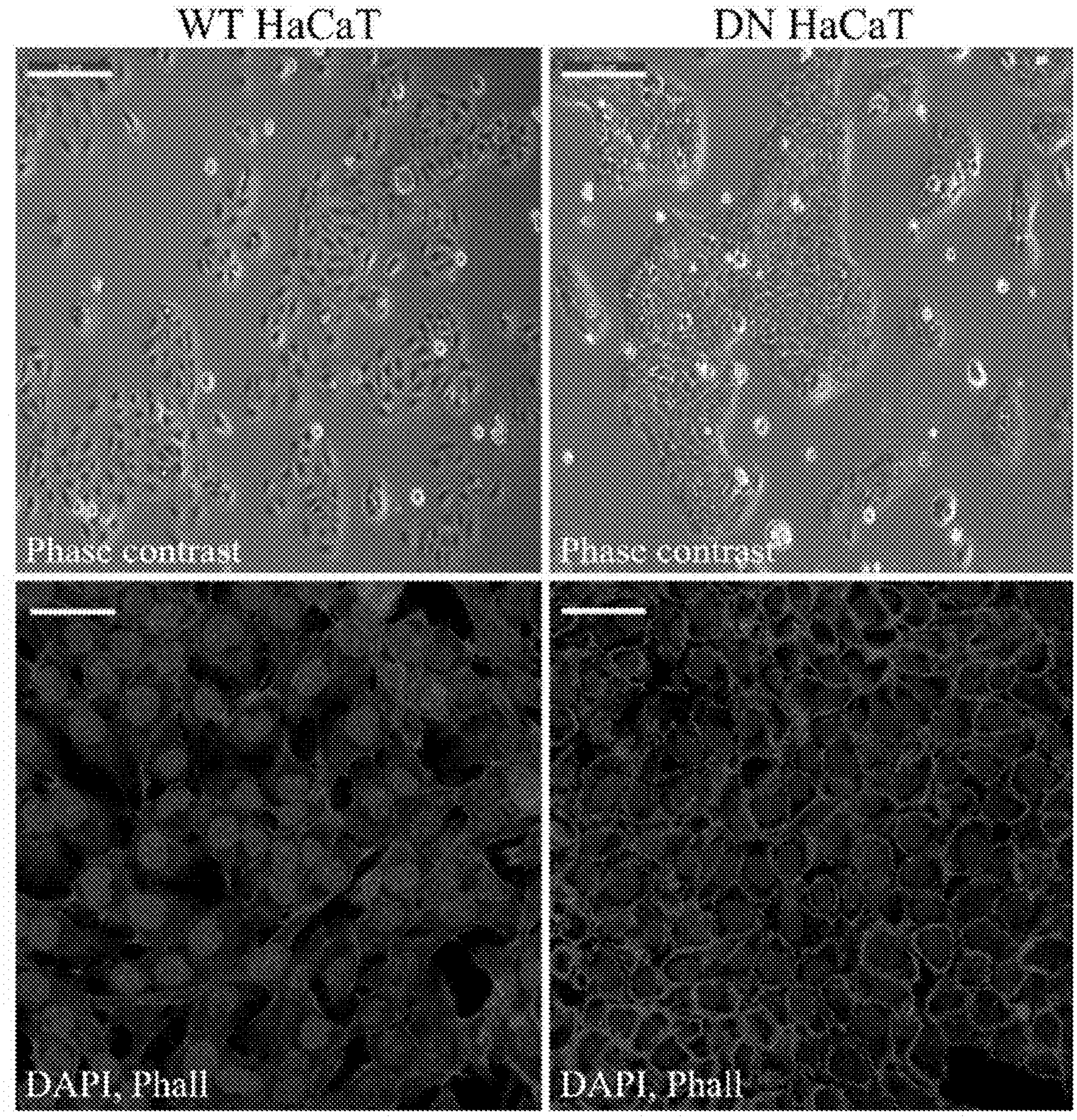
FIGS. 6A-6C are a microscopic image analysis of WT (control) and stably transfected DN-SUNL HaCaT cells, which shows that LINC complex disruption affects drastically cell morphology, cell crowding and cell-cell contact protein expression on 2D surfaces.
Figure 6B:
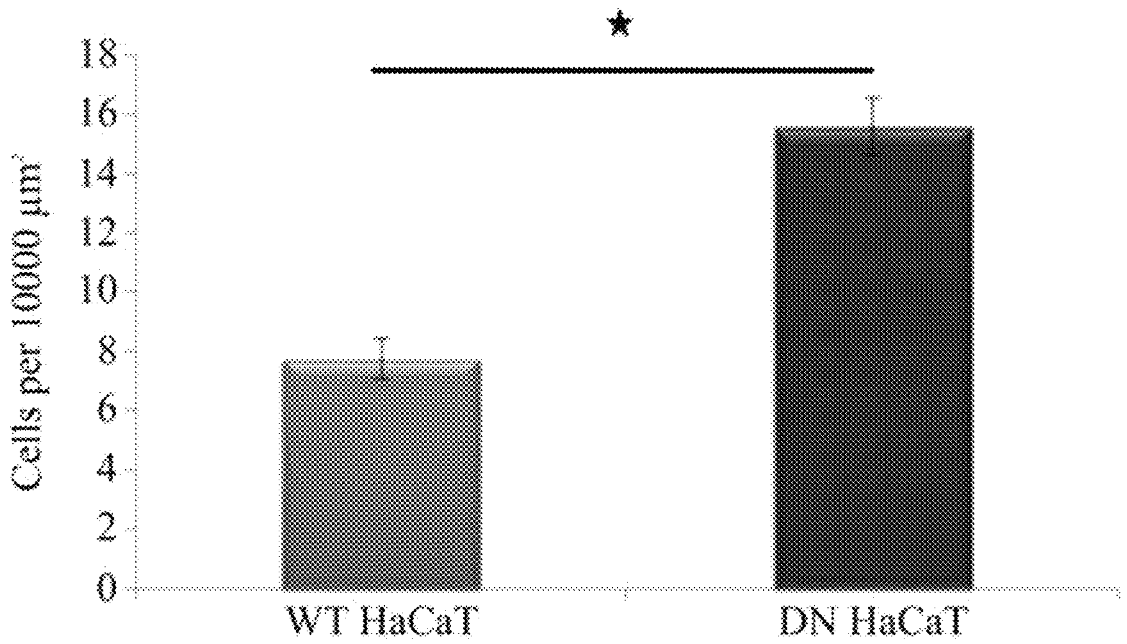
Figure 6C:
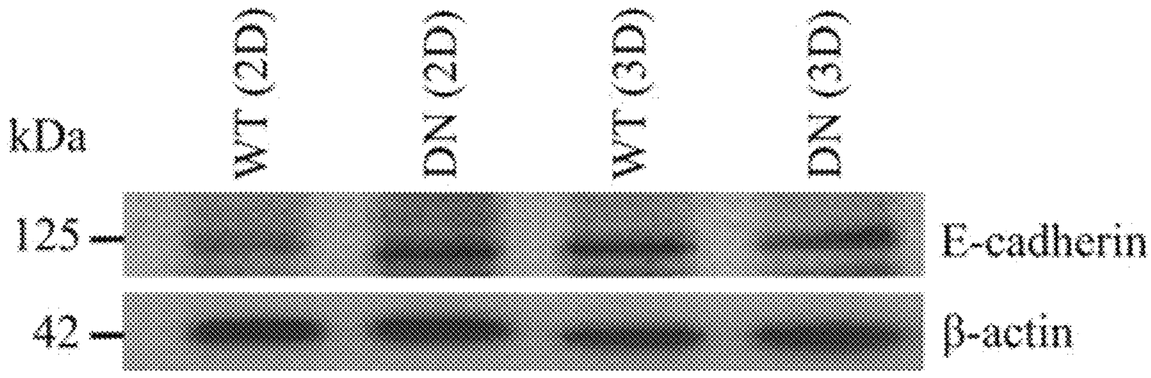

Example 4—LINC Disruption Affects Cell Shape, Cell-cell Junction Protein Expression and Cellular Density A microscopic comparison (i.e. phase contrast images and fluorescence examination of TRITC-coupled phalloidin [phalloidin binds filamentous actin]) of WT and stable DN-SUN HaCaT clones (FIG. 6A) grown at 60% confluency under standard 2D conditions indicates drastic changes in the overall appearance of the mutants. While both WT and DN-SUNL form colonies the latter appear to contain more cells, which exhibit strong cortical F-actin staining and a smaller circumference. Statistical analysis indicates that DN-SUNL HaCaT cells display a significantly smaller cellular area of 262 $\mu m^2$ compared to a calculated cell area of 473 $\mu m^2$ for WT cells. This drastic difference in the DN-SUNL cell area is reflected also in the number of cells that occupy a 100×100 μm area. On average 7.4 WT cells are found within a 10000 $\mu m^2$ colony area, while for DN-SUNL 15.8 cells were observed (FIG. 6B). The pronounced cellular crowding effect of DN-SUNL may be the outcome of higher E-cadherin expression, which hinds the presence of enhanced cell-cell contacts when the cells are grown on 2D surfaces (FIG. 6C). Interestingly, the DN-SUNL effects on the expression of E-cadherin appear to be attenuated upon 3D cell culture (FIG. 6C).

Example 5—LINC Complex Disruption Alters Cell-Substratum Adhesion

Considering that DN-SUNL expressing cells display a drastically smaller cellular area, the inventors elucidated whether the adhesion of the cells to the surface has been altered. Examination of vinculin indeed indicates alterations in the localisation of the protein within the cytoplasm in DN-SUNL mutant cells. In WT cells the majority of vinculin is localised at focal contacts, which can be seen as distinct large clusters at the periphery of the cells (denoted by arrows, FIG. 7A). Moreover, WT cells appear very flat, which is evident not only by the presence of focal contacts but also from the large area that is occupied by the cytoplasm. In sharp contrast, DN-SUNL cells exhibit vinculin staining, which is confined in the cytoplasm and lack distinct focal contacts at the periphery (FIG. 7B). Western blot analysis of equal amounts of WT, and DN-SUNL cell lysates (two clones were examined) indicates that the levels of vinculin are not affected in the mutants. In summary, the data show that the subcellular distribution of vinculin is affected but not its expression levels upon LINC complex disruption in HaCaT keratinocytes. Moreover, the data suggest that a reduced cell-substratum attachment and an enhanced cell-cell adhesion may account for the cell density and morphological phenotype of the mutants.

Example 6—LINC Complex Disruption Enhances the Stratification Properties of HaCaT Keratinocytes in 3D Cell Culture Conditions Upon exposure to the air-liquid interphase keratinocytes start to differentiate and form a multi-layered structure.

Figure 8A:
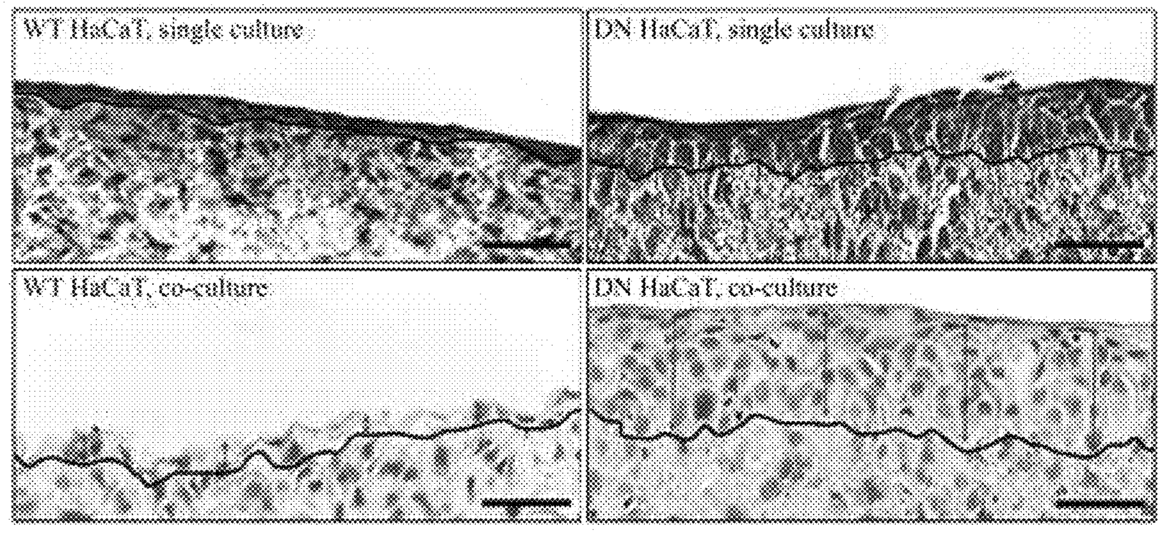
FIGS. 8A-8C are an analysis, which shows that DN-SUNL HaCaT cells (DN) display enhanced stratification properties when grown in 3D scaffolds for 8 days at the air-to-liquid interface.
Figure 8B:
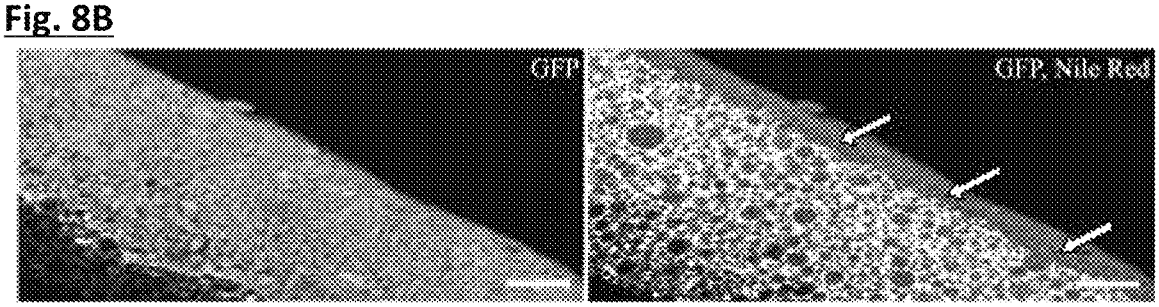
Figure 8C:
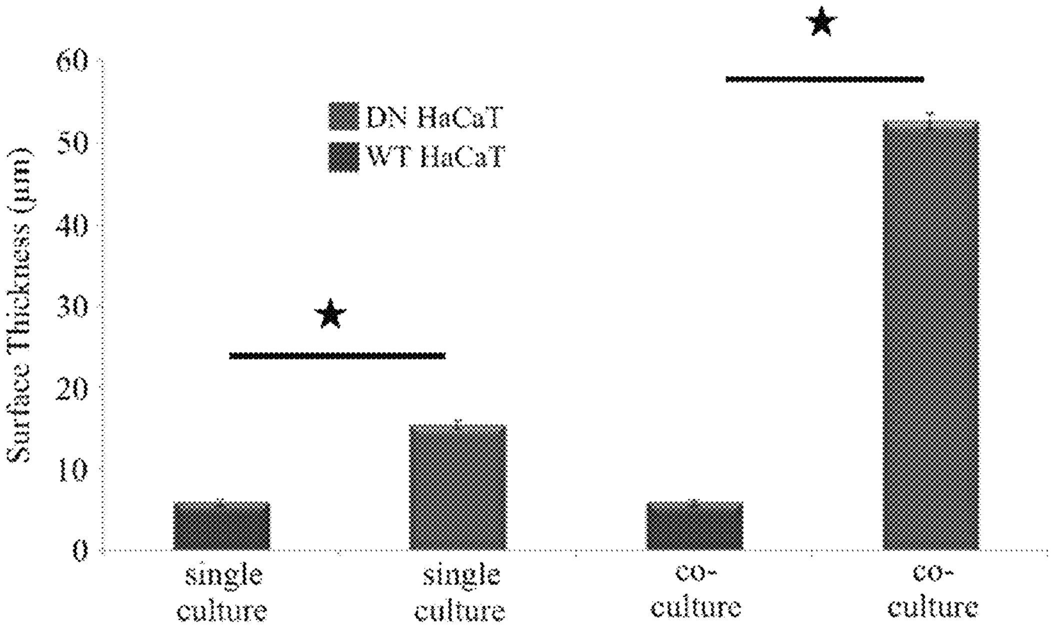

Cellular division is restricted to the cells that are in immediate contact with the cell culture media, while differentiated cells significantly flatten and occupy the areas that are further away from the media surface. Irrespectively, of whether DN-SUN HaCaT cells are grown alone (single culture) or in the presence of fibroblasts (co-culture) in 3D their ability of forming multi-layered cell assemblies is profoundly enhanced when compared to WT cells. FIG. 8A indicates that DN-SUNL cells form more layers when compared to WT. In addition, FIG. 8A shows that the DN cell layers occupy the area above the scaffold and that the differentiation programme is executed properly considering the drastic cell shape changes that occur in the upper layers (note the significant cell flattening that occurs in the co-culture permutation). The ability of the DN cells to form pronounced structures above the scaffold is shown in FIG. 8B. As can be seen DN-cells (GFP-positive due to DN-SUNL expression) grow both into (GFP-panel) and above the scaffold (Nile red co-stained sample). Note the presence of GFP-positive structures above the Nile red stained 3D scaffold, which shows that cell stacking occurs above the scaffold (FIG. 8B) and is enhanced upon LINC disruption (FIG. 8C).

Figure 9A:
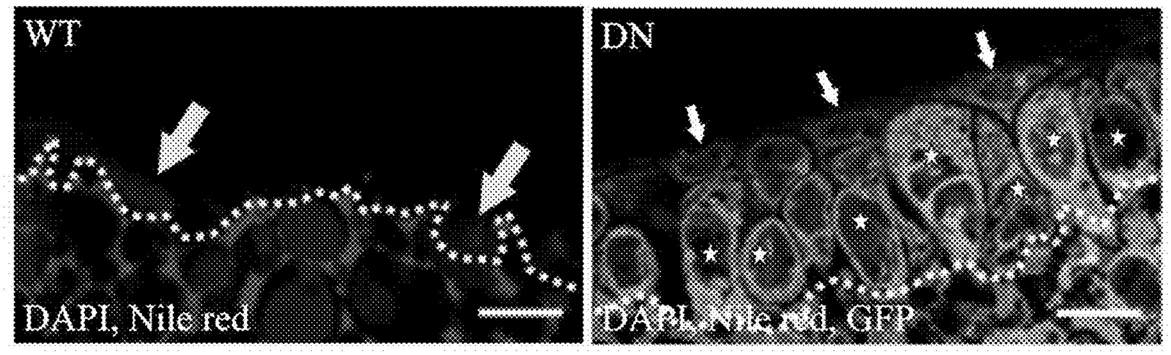
FIGS. 9A-9B are an analysis, which shows that DN HaCaT cells display proper epidermal tissue architecture in vitro.
Figure 9B:
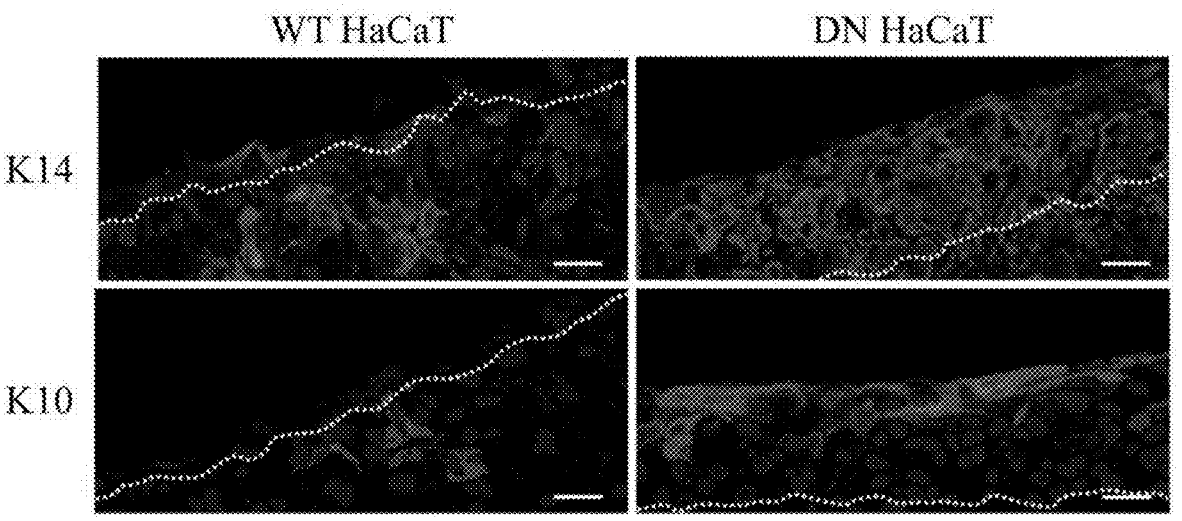

Example 7—LINC Complex Disruption Enhances Cell Stratification and Differentiation To elucidate whether the morphological alterations (pronounced cell/nuclear flattening) exhibited by DN-SUNL cells (FIG. 9A, small arrows) correspond to differentiated cells the epidermal models were counterstained with Keratin to. As can be seen in FIG. 9B, the anti-Keratin 10 immunofluorescence indicates that keratin 10 is present in the outermost cell layers of the DN-SUNL epidermal equivalent. In summary, FIGS. 9A-9B shows that DN-SUNL cells (relative to WT cells) have enhanced stratification properties, a proper spatial expression of the K10 differentiation marker when grown at the air-liquid interface in 3D and a cell morphology that mimics the shapes of keratinocytes of skin (e.g. columnar shape for cells in the direct vicinity of the scaffold [FIG. 9A, asterisks], and a squamous appearance for differentiated cells [FIG. 9A, small arrows]).

Example 8—DN-SUNL Expression Disrupts the Linkage of the INM to the ONM

Figure 10A:
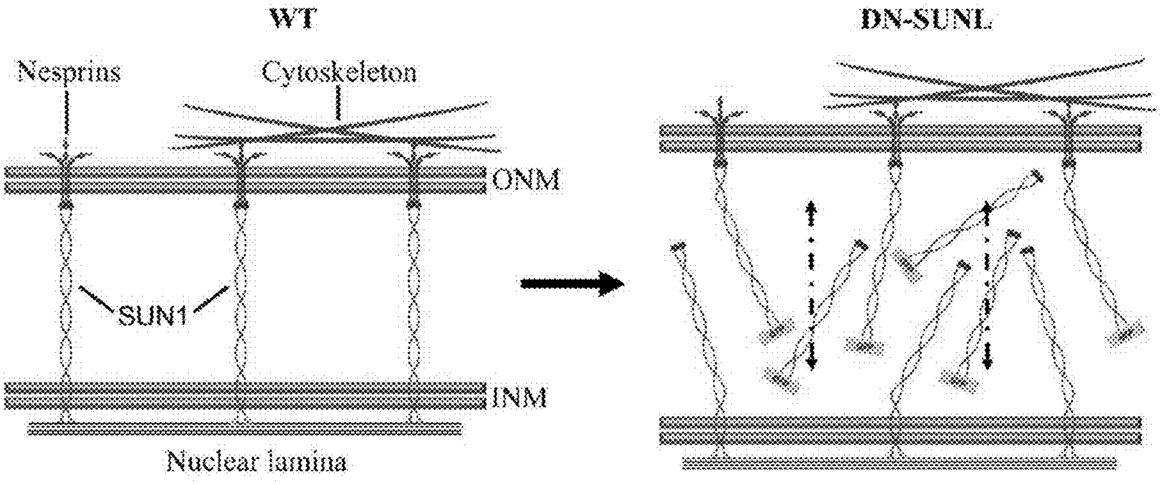
FIG. 10A is a schematic diagram showing that DN-SUNL expression saturates KASH-domain binding sites at the outer nuclear membrane (ONM) and prevents binding to full-length SUN-domain proteins. DN-SUNL expression consequently disrupts the linkage of the ONM to the inner nuclear membrane (INM) and dilates the perinuclear lumen (discontinuous double arrowed lines).
Figure 10B:
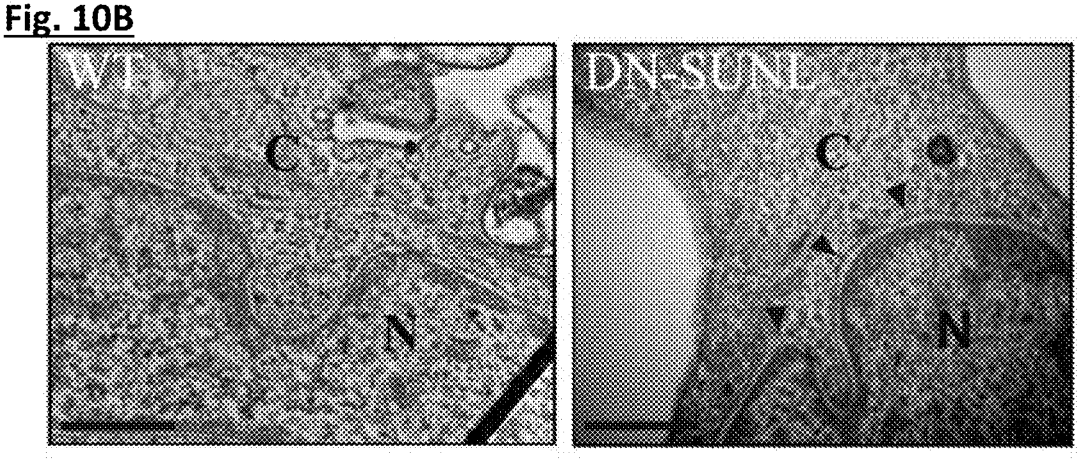
FIG. 10B shows TEM micrographs of the nuclear membrane in WT (control) and DN-SUNL HaCaT cells. Arrowheads denote dilation of the nuclear envelope in DN-SUNL cells. C=cytoplasm, N=nucleus. Scale bar 500 nm.
Figure 10C:
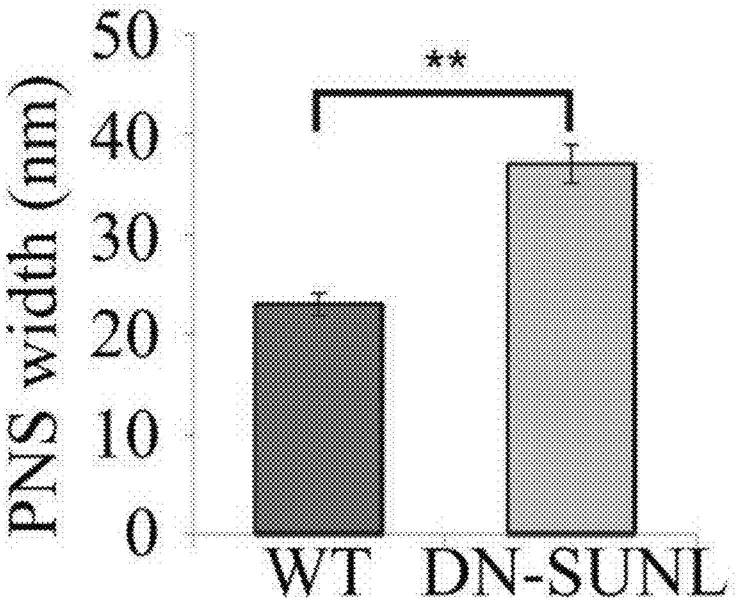
FIG. 10C Histogram shows the width of the perinuclear lumen in WT and DN-SUNL expressing cells. Statistical analysis (Student's t test; P value<0.005 is indicated by **) demonstrates a significant dilation of the nuclear envelope in DN-SUNL mutants. Results are mean±standard deviation.

To demonstrate that DN-SUNL disrupts the physical linkage of the inner nuclear membrane to the outer nuclear membrane (FIG. 10A) we performed an EM analysis of the DN-SUNL cells relative to WT. EM images indicate that the lumen of the nuclear envelope (NE) is even and narrow in WT, while DN-SUNL cells exhibit dilations (FIG. 10B). Measurements of the NE lumen indicate a significant dilation in DN-SUN expressing cells (FIG. 10C).

Example 9—LINC Disruption Yields Compact, Taller and Softer Cell Colonies

Figure 11A:
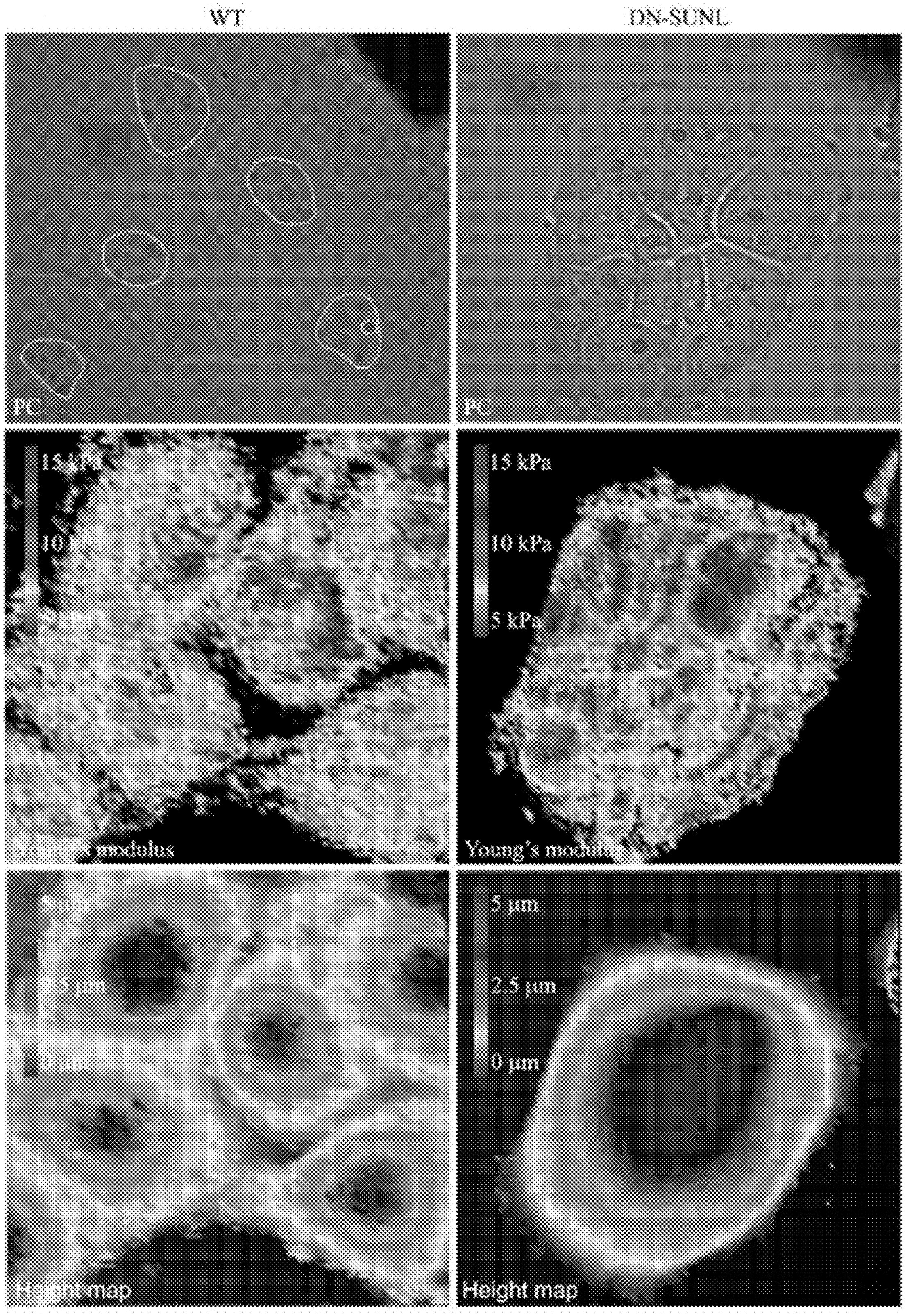
FIGS. 11A-11D are an analysis of the cytoplasmic and nuclear organelle biomechanical properties of interphase WT and DN-SUNL HaCaT cells examined under biological conditions, showing that LINC complex disruption (DN-SUNL cells) yields significantly softer cells.
Figure 11B:
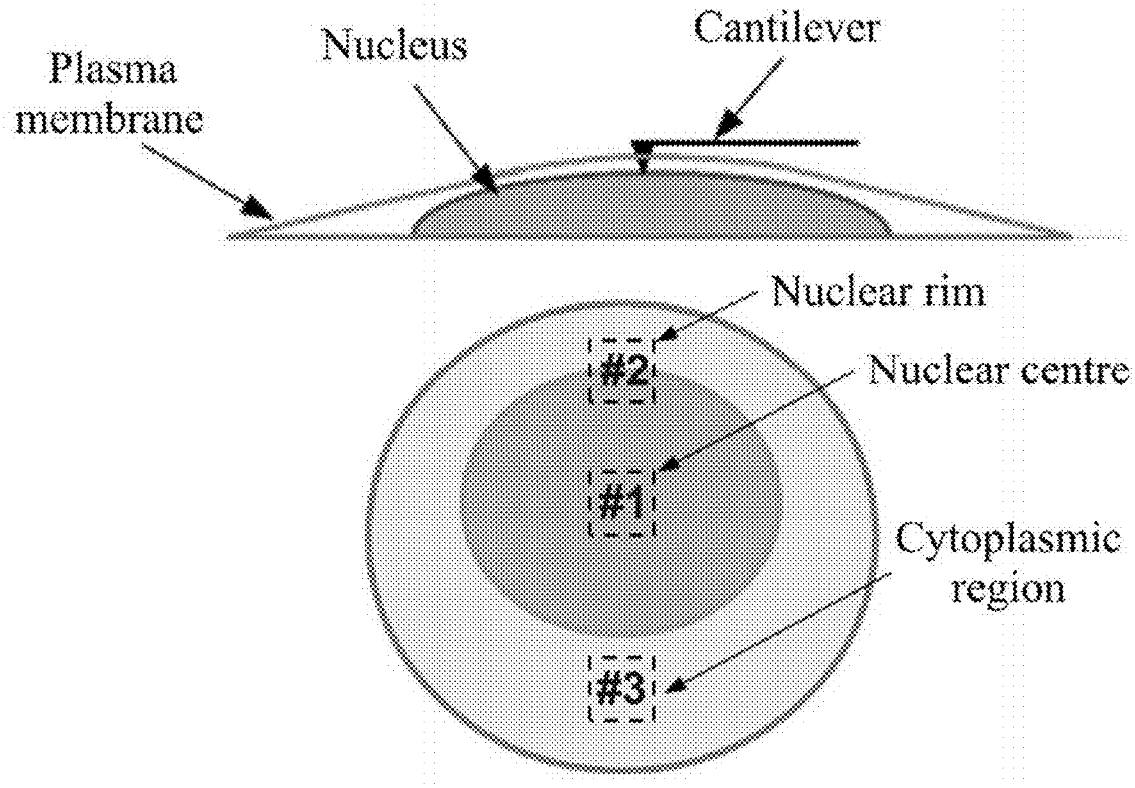
Figure 11C:
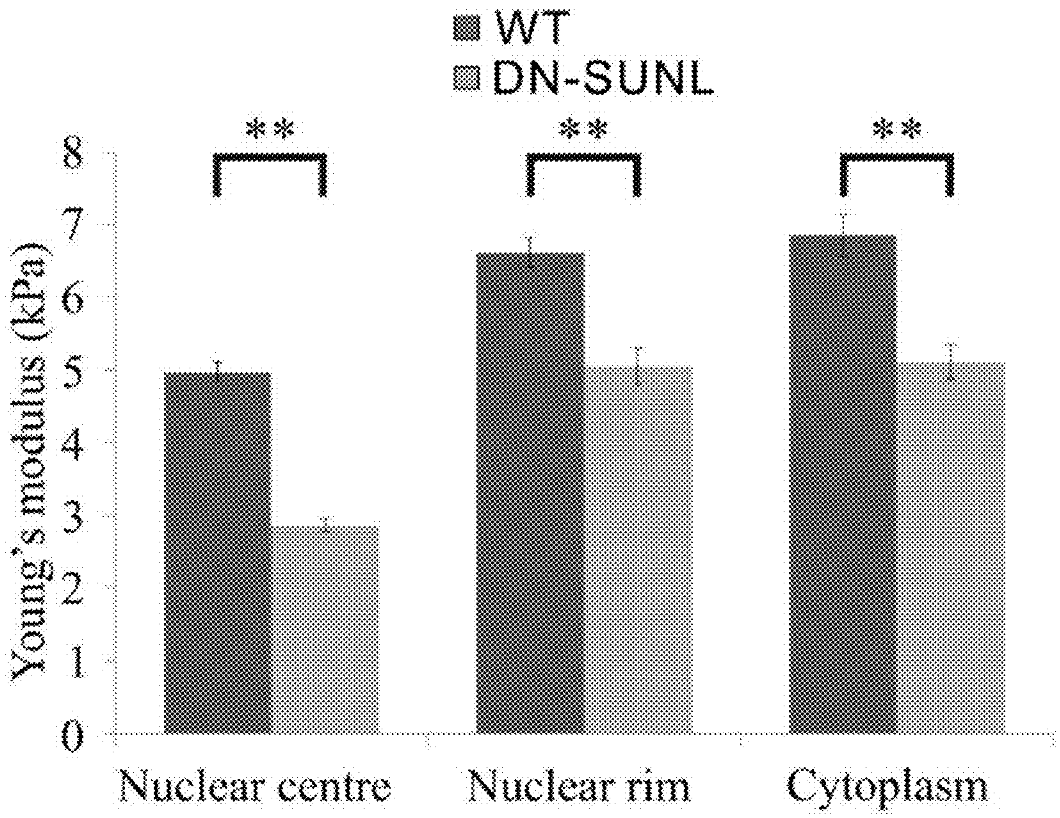
Figure 11D:
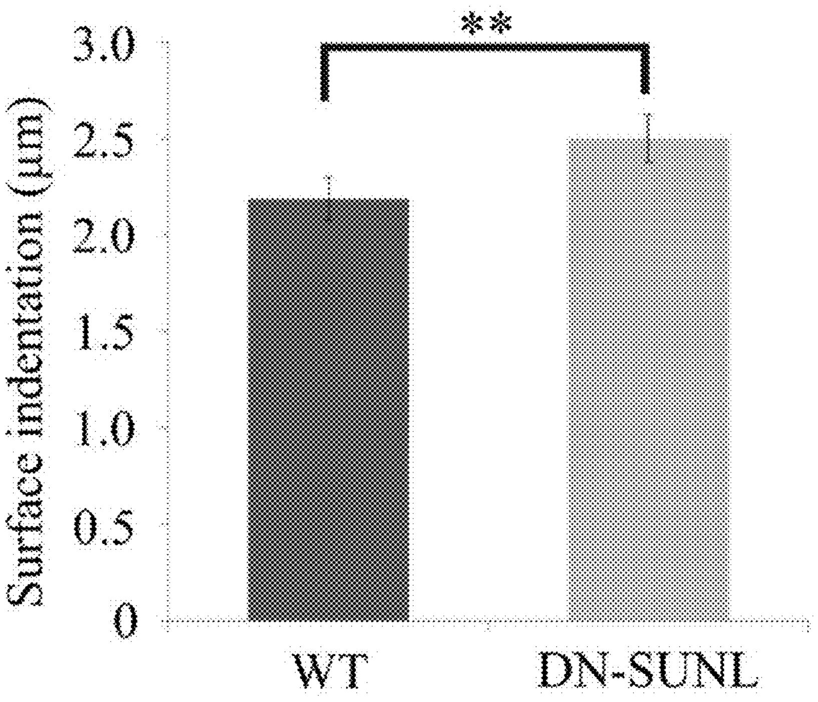

To examine the physical properties of WT and DN-SUNL cells the inventors performed an AFM analysis on living cells. The data in FIG. 11A verify that DN-SUNL colonies compared to WT are more compact and contain more cells (phase contrast). Moreover, Young's modulus measurements (FIG. 11A, middle panel) indicate that mutants are significantly softer irrespectively of the cellular regions that were assessed (Nuclear centre, nuclear rim and cytoplasm FIGS. 11B and 11C). Collectively, these data suggest that DN-SUNL cells exhibit softer nuclei and softer cytoplasms, suggesting that DN-SUNL expression yields softer cells, which is further substantiated by the pronounced cantilever indentation in the mutants (FIG. 11D). Finally, the height map in FIG. 11A (lower panel) shows that DN-SUNL cells are taller when compared to WT, which again underlines that LINC complex manipulation controls cell/colony architecture.

SEQUENCE LISTING

```
Sequence total quantity: 31
SEQ ID NO: 1            moltype = DNA  length = 241
FEATURE                 Location/Qualifiers
source                  1..241
                        mol_type = genomic DNA
                        organism = Homo sapiens
SEQUENCE: 1
gtccacaaaa ggtggctccg attcctccct ttctgagcca gggccaggtc ggtccggccg  60
cggcttcctg ttcagagtcc tccgagcagc tcttcccctt cagcttctcc tgctcctcct  120
catcgggctt gcctgccttg taccaatgtc agaggaagac tacagctgtg ccctctccaa  180
caactttgcc cggtcattcc accccatgct cagatacacg aatggccctc ctccactctg  240
a                                                                  241

SEQ ID NO: 2            moltype = AA  length = 51
FEATURE                 Location/Qualifiers
source                  1..51
                        mol_type = protein
                        organism = Homo sapiens
SEQUENCE: 2
AALPLQLLLL LLIGLACLVP MSEEDYSCAL SNNFARSFHP MLRYTNGPPP L           51

SEQ ID NO: 3            moltype = DNA  length = 208
FEATURE                 Location/Qualifiers
source                  1..208
                        mol_type = genomic DNA
                        organism = Homo sapiens
SEQUENCE: 3
ggtccccggc agcacacggc cacagcgctc cttcctctca agggtggtcc gggcagccct  60
acccctgcag ctgctcctcc tgctgctgct gctcctggcc tgcctgctgc cctcctccga  120
agaagactac agctgcactc aggccaacaa ctttgcccgg tcctttttacc ccatgctgag  180
```

```
gtacaccaat gggccacccc ccacatag                                      208

SEQ ID NO: 4           moltype = AA  length = 51
FEATURE                Location/Qualifiers
source                 1..51
                       mol_type = protein
                       organism = Homo sapiens
SEQUENCE: 4
AALPLQLLLL LLLLLACLLP SSEEDYSCTQ ANNFARSFYP MLRYTNGPPP T           51

SEQ ID NO: 5           moltype = DNA  length = 201
FEATURE                Location/Qualifiers
source                 1..201
                       mol_type = genomic DNA
                       organism = Homo sapiens
SEQUENCE: 5
actcggcggt ggcgaggact gggctccctc ttccggaggg cgtgctgtgt ggcgctccca  60
ctgcagctgc ttctgctgct gttcctcctc ctgctgttcc tgctcccaat cagggaagag  120
gaccgcagct gcaccctggc caacaacttc gcccgctcct tcacgctcat gctgcgctac  180
aatggcccac cacccaccta a                                             201

SEQ ID NO: 6           moltype = AA  length = 50
FEATURE                Location/Qualifiers
source                 1..50
                       mol_type = protein
                       organism = Homo sapiens
SEQUENCE: 6
VALPLQLLLL LFLLLLFLLP IREEDRSCTL ANNFARSFTL MLRYNGPPPT             50

SEQ ID NO: 7           moltype = DNA  length = 184
FEATURE                Location/Qualifiers
source                 1..184
                       mol_type = genomic DNA
                       organism = Homo sapiens
SEQUENCE: 7
ggcccccgat cctgcatcca ggcagcctct gaccttcctc cttatcctct tcctcctctt  60
cctcctcctg gtgggtgcca tgtttctcct gcccgcgtca ggaggcccct gctgctctca  120
tgcccgaata cccaggacac cctacctggt gctcagctat gtcaatggtc ttcccccagt  180
ctga                                                                184

SEQ ID NO: 8           moltype = AA  length = 49
FEATURE                Location/Qualifiers
source                 1..49
                       mol_type = protein
                       organism = Homo sapiens
SEQUENCE: 8
FLLILFLLFL LLVGAMFLLP ASGGPCCSHA RIPRTPYLVL SYVNGLPPV              49

SEQ ID NO: 9           moltype = DNA  length = 494
FEATURE                Location/Qualifiers
source                 1..494
                       mol_type = genomic DNA
                       organism = Homo sapiens
SEQUENCE: 9
gtggcagcat cttgagtact cgctgttctg aaacttacga aaccaaaacg gcgctgatga  60
gtctgtttgg gatcccgctg tggtacttct cgcagtcccc gcgcgtggtc atccagcctg  120
acatttaccc cggtaactgc tgggcattta aaggctccca ggggtacctg gtggtgaggc  180
tctccatgat gatccaccca gccgccttca ctctggagca catccctaag acgctgtcgc  240
caacaggcaa catcagcagc gcccccaagg acttcgccgt ctatggatta gaaaatgagt  300
atcaggaaga agggcagctt ctgggacagt tcacgtatga tcaggatggg gagtcgctcc  360
agatgttcca ggccctgaaa agacccgacg acacagcttt ccaaatagtg gaacttcgga  420
ttttttctaa ctggggccat cctgagtata cctgtctgta tcggttcaga gttcatggcg  480
aacctgtcaa gtga                                                     494

SEQ ID NO: 10          moltype = AA  length = 163
FEATURE                Location/Qualifiers
source                 1..163
                       mol_type = protein
                       organism = Homo sapiens
SEQUENCE: 10
GSILSTRCSE TYETKTALMS LFGIPLWYFS QSPRVVIQPD IYPGNCWAFK GSQGYLVVRL  60
SMMIHPAAFT LEHIPKTLSP TGNISSAPKD FAVYGLENEY QEEGQLLGQF TYDQDGESLQ  120
MFQALKRPDD TAFQIVELRI FSNWGHPEYT CLYRFRVHGE PVK                     163

SEQ ID NO: 11          moltype = DNA  length = 491
FEATURE                Location/Qualifiers
source                 1..491
                       mol_type = genomic DNA
                       organism = Homo sapiens
```

```
SEQUENCE: 11
gggccagcgt catcagcacc cgatgttctg agacctacga gaccaagacg gccctcctca  60
gcctcttcgg catccccctg tggtaccact cccagtcacc ccgagtcatc ctccagccag  120
atgtgcaccc aggcaactgc tgggccttcc aggggccaca aggcttcgcc gtggtccgcc  180
tctctgcccg catccgcccc acagccgtta ccttagagca tgtgcccaag gccttgtcac  240
ccaacagcac tatctccagt gcccccaagg acttcgccat ctttgggttt gacgaagacc  300
tgcagcagga ggggacactc cttggcaagt tcacttacga tcaggacggc gagcctattc  360
agacgtttca ctttcaggcc cctacgatgg ccacgtacca ggtggtggag ctgcggatcc  420
tgactaactg gggccacccc gagtacacct gcatctaccg cttcagagtg catggggagc  480
ccgcccacta g                                                      491

SEQ ID NO: 12          moltype = AA  length = 162
FEATURE                Location/Qualifiers
source                 1..162
                       mol_type = protein
                       organism = Homo sapiens
SEQUENCE: 12
ASVISTRCSE TYETKTALLS LFGIPLWYHS QSPRVILQPD VHPGNCWAFQ GPQGFAVVRL  60
SARIRPTAVT LEHVPKALSP NSTISSAPKD FAIFGFDEDL QQEGTLLGKF TYDQDGEPIQ  120
TFHFQAPTMA TYQVVELRIL TNWGHPEYTC IYRFRVHGEP AH                    162

SEQ ID NO: 13          moltype = DNA  length = 497
FEATURE                Location/Qualifiers
source                 1..497
                       mol_type = genomic DNA
                       organism = Homo sapiens
SEQUENCE: 13
gagcctccat cattgaagct gggacctcag aaagttataa aaataataaa gcaaaattgt  60
actggcatgg gataggtttc ctaaatcatg aaatgcctcc agatattatt cttcagccgg  120
atgtctaccc tggaaagtgc tgggcttttc caggttccca gggtcatacc ctaatcaagc  180
ttgctacaaa gatcatacca actgctgtta ccatggagca catctcagag aaggtgtctc  240
cgtcaggaaa catctccagt gcacccaagg aatttctgt  ctatggcatc acaaaaaaat  300
gtgaaggaga agaaattttc ctaggtcagt ttatatataa caaaacagga accaccgttc  360
aaacatttga actccagcat gcagtttctg aatatttatt atgtgtgaaa cttaatatct  420
ttagcaactg gggacacccg aagtatactt gtttatatcg attcagggtc catggcacac  480
caggcaagca catctag                                                497

SEQ ID NO: 14          moltype = AA  length = 164
FEATURE                Location/Qualifiers
source                 1..164
                       mol_type = protein
                       organism = Homo sapiens
SEQUENCE: 14
ASIIEAGTSE SYKNNKAKLY WHGIGFLNHE MPPDIILQPD VYPGKCWAFP GSQGHTLIKL  60
ATKIIPTAVT MEHISEKVSP SGNISSAPKE FSVYGITKKC EGEEIFLGQF IYNKTGTTVQ  120
TFELQHAVSE YLLCVKLNIF SNWGHPKYTC LYRFRVHGTP GKHI                  164

SEQ ID NO: 15          moltype = DNA  length = 521
FEATURE                Location/Qualifiers
source                 1..521
                       mol_type = genomic DNA
                       organism = Homo sapiens
SEQUENCE: 15
gagcctccat cgacctgcag aagacatccc acgattacgc agacaggaac actgcctact  60
tctggaatcg cttcagcttc tggaactacg cacggccgcc cacggttatc ctggagcccc  120
acgtgttccc tgggaattgc tgggcttttg aaggcgacca aggccaggtg gtgatccaac  180
tgccgggccg agtgcagctg agcgacatca ctctgcagca tccaccgccc agcgtggagc  240
acaccggagg agccaacagc gccccccgcg atttcgcggt ctttggcctc caggtttatg  300
atgaaactga agtttccttg gggaaattca ccttcgatgt tgagaaatcg gagattcaga  360
ctttccacct gcagaatgac cccccagctg cctttcccaa ggtgaagatc cagattctaa  420
gcaactgggg ccaccccctgt ttcacgtgct tgtatcgagt ccgtgcccac ggtgtgcgaa  480
cctcagaggg ggcagagggc agtgcacagg ggccccatta a                     521

SEQ ID NO: 16          moltype = AA  length = 172
FEATURE                Location/Qualifiers
source                 1..172
                       mol_type = protein
                       organism = Homo sapiens
SEQUENCE: 16
ASIDLQKTSH DYADRNTAYF WNRFSFWNYA RPPTVILEPH VFPGNCWAFE GDQGQVVIQL  60
PGRVQLSDIT LQHPPPSVEH TGGANSAPRD FAVFGLQVYD ETEVSLGKFT FDVEKSEIQT  120
FHLQNDPPAA FPKVKIQILS NWGHPRFTCL YRVRAHGVRT SEGAEGSAQG PH         172

SEQ ID NO: 17          moltype = DNA  length = 527
FEATURE                Location/Qualifiers
source                 1..527
                       mol_type = genomic DNA
                       organism = Homo sapiens
SEQUENCE: 17
```

-continued

```
gggccagcat tgactttgag cacacgtcag tcacctataa ccatgagaag gcccactcct  60
actggaactg gatccagctg tggaactacg cacagccccc agacgtgatc cttgagccca  120
acgtgacacc tggcaattgc tgggcctttg agggtgaccg cggccaggtg accatccaat  180
tggctcagaa ggtttacctg tccaacctca cgctgcagca catccccaag accatctcat  240
tgtcaggcag cctggacacc gcccccaagg acttcgtcat ctatggcatg gagggctccc  300
ccaaggagga ggtgttcctg gggcatttc agtttcagcc agaaaacatc atccagatgt  360
tcccactcca gaaccagccg gcccgggctt tcagtgcggt caaggtgaag atctcaagca  420
actgggggaa cccaggcttc acttgcctgt accgcgtgcg agtgcatggc tctgtggccc  480
cgcccagaga gcagcctcac cagaacccct accctaagag agattaa               527

SEQ ID NO: 18          moltype = AA  length = 174
FEATURE                Location/Qualifiers
source                 1..174
                       mol_type = protein
                       organism = Homo sapiens
SEQUENCE: 18
ASIDFEHTSV TYNHEKAHSY WNWIQLWNYA QPPDVILEPN VTPGNCWAFE GDRGQVTIQL  60
AQKVYLSNLT LQHIPKTISL SGSLDTAPKD FVIYGMEGSP KEEVFLGAFQ FQPENIIQMF  120
PLQNQPARAF SAVKVKISSN WGNPGFTCLY RVRVHGSVAP PREQPHQNPY PKRD        174

SEQ ID NO: 19          moltype = DNA  length = 1995
FEATURE                Location/Qualifiers
source                 1..1995
                       mol_type = genomic DNA
                       organism = Homo sapiens
SEQUENCE: 19
atggagaccc cgtcccagcg gcgcgccacc cgcagcgggg cgcaggccag ctccactccg  60
ctgtcgccca cccgcatcac ccggctgcag gagaaggagg acctgcagga gctcaatgat  120
cgcttggcgg tctacatcga ccgtgtgcgc tcgctggaaa cggagaacgc agggctgcgc  180
cttcgcatca ccgagtctga agaggtggtc agccgcgagg tgtccggcat caaggccgcc  240
tacgaggccg agctcgggga tgcccgcaag acccttgact cagtagccaa ggagcgcgcc  300
cgcctgcagc tggagctgag caaagtgcgt gaggagttta aggagctgaa agcgcgcaat  360
accaagaagg agggtgacct gatagctgct caggctcggc tgaaggacct ggaggctctg  420
ctgaactcca aggaggccgc actgagcact gctctcagtg agaagcgcac gctggagggc  480
gagctgcatg atctgcgggg ccaggtggcc aagcttgagg cagccctagg tgaggccaag  540
aagcaacttc aggatgagat gctgcggcgg gtggatgctg agaacaggct gcagaccatg  600
aaggaggaac tggacttcca gaagaacatc tacagtgagg agctgcgtga gaccaagcgc  660
cgtcatgaga cccgactggt ggagattgac aatgggaagc agcgtgagtt tgagagccgg  720
ctggcggatg cgctgcagga actgcgggcc cagcatgagg accaggtgga gcagtataag  780
aaggagctgg agaagactta ttctgccaag ctggacaatg ccaggcagtc tgctgagagg  840
aacagcaacc tggtgggggc tgcccacgag gagctgcagc agtcgcgcat ccgcatcgac  900
agcctctctg cccagctcag ccagctccag aagcagctgg cagccaagga ggcgaagctt  960
cgagacctgg aggactcact ggcccgtgag cgggacacca gccggcggct gctggcggaa  1020
aaggagcggg agatggccga gatgcgggca aggatgcagc agcagctgga cgagtaccag  1080
gagcttctgg acatcaagct ggccctggac atggagatcc acgcctaccg caagctcttg  1140
gagggcgagg aggagaggct acgcctgtcc cccagcccta cctcgcagcg cagccgtggc  1200
cgtgcttcct ctcactcatc ccagacacag ggtgggggca gcgtcaccaa aaagcgcaaa  1260
ctggagtcca ctgagagccg cagcagcttc tcacagcacg cacgcactag cgggcgcgtg  1320
gccgtggagg aggtggatga ggagggcaag tttgtccggc tgcgcaacaa gtccaatgag  1380
gaccagtcca tgggcaattg gcagatcaag cgccagaatg gagatgatcc cttgctgact  1440
taccggttcc caccaaagtt caccctgaag gctgggcagg tggtgacgat ctgggctgca  1500
ggagctgggg ccacccacag ccccccctacc gacctggtgt ggaaggcaca gaacacctgg  1560
ggctgcggga acagcctgcg tacggctctc atcaactcca ctggggaaga agtggccatg  1620
cgcaagctgg tgcgctcagt gactgtggtt gaggacgacg aggatgagga tggagatgac  1680
ctgctccatc accaccacgg ctcccactgc agcagctcgg gggaccccgc tgagtacaac  1740
ctgcgctcgc gcaccgtgct gtgcgggacc tgcgggcagc ctgccgacaa ggcatctgcc  1800
agcggctcag gagcccaggt gggcggaccc atctcctctg gctcttctgc ctccagtgtc  1860
acggtcactc gcagctaccg cagtgtgggg ggcagtgggg gtggcagctt cggggacaat  1920
ctggtcaccc gctcctacct cctgggcaac tccagccccc gaacccagag cccccagaac  1980
tgcagcatca tgtaa                                                   1995

SEQ ID NO: 20          moltype = AA  length = 664
FEATURE                Location/Qualifiers
source                 1..664
                       mol_type = protein
                       organism = Homo sapiens
SEQUENCE: 20
METPSQRRAT RSGAQASSTP LSPTRITRLQ EKEDLQELND RLAVYIDRVR SLETENAGLR  60
LRITESEEVV SREVSGIKAA YEAELGDARK TLDSVAKERA RLQLELSKVR EEFKELKARN  120
TKKEGDLIAA QARLKDLEAL LNSKEAALST ALSEKRTLEG ELHDLRGQVA KLEAALGEAK  180
KQLQDEMLRR VDAENRLQTM KEELDFQKNI YSEELRETKR RHETRLVEID NGKQREFESR  240
LADALQELRA QHEDQVEQYK KELEKTYSAK LDNARQSAER NSNLVGAAHE ELQQSRIRID  300
SLSAQLSQLQ KQLAAKEAKL RDLEDSLARE RDTSRRLLAE KEREMAEMRA RMQQQLDEYQ  360
ELLDIKLALD MEIHAYRKLL EGEEERLRLS PSPTSQRSRG RASSHSSQTQ GGGSVTKKRK  420
LESTESRSSF SQHARTSGRV AVEEVDEEGK FVRLRNKSNE DQSMGNWQIK RQNGDDPLLT  480
YRFPPKFTLK AGQVVTIWAA GAGATHSPPT DLVWKAQNTW GCGNSLRTAL INSTGEEVAM  540
RKLVRSVTVV EDDEDEDGDD LLHHHHGSHC SSSGDPAEYN LRSRTVLCGT CGQPADKASA  600
SGSGAQVGGP ISSGSSASSV TVTRSYRSVG GSGGGSFGDN LVTRSYLLGN SSPRTQSPQN  660
CSIM                                                               664
```

```
SEQ ID NO: 21          moltype = DNA  length = 1719
FEATURE                Location/Qualifiers
source                 1..1719
                       mol_type = genomic DNA
                       organism = Homo sapiens
SEQUENCE: 21
atggagaccc cgtcccagcg gcgcgccacc cgcagcgggg cgcaggccag ctccactccg  60
ctgtcgccca cccgcatcac ccggctgcag gagaaggagg acctgcagga gctcaatgat  120
cgcttggcgg tctacatcga ccgtgtgcgc tcgctggaaa cggagaacgc agggctgcgc  180
cttcgcatca ccgagtctga agaggtggtc agccgcgagg tgtccggcat caaggccgcc  240
tacgaggccg agctcgggga tgcccgcaag acccttgact cagtagccaa ggagcgcgcc  300
cgcctgcagc tggagctgag caaagtgcgt gaggagttta aggagctgaa agcgcgcaat  360
accaagaagg agggtgacct gatagctgct caggctcggc tgaaggacct ggaggctctg  420
ctgaactcca aggaggccgc actgagcact gctctcagtg agaagcgcac gctggagggc  480
gagctgcatg atctgcgggg ccaggtggcc aagcttgagg cagccctagg tgaggccaag  540
aagcaacttc aggatgagat gctgcggcgg gtggatgctg agaacaggct gcagaccatg  600
aaggaggaac tggacttcca gaagaacatc tacagtgagg agctgcgtga gaccaagcgc  660
cgtcatgaga cccgactggt ggagattgac aatgggaagc agcgtgagtt tgagagccgg  720
ctggcggatg cgctgcagga actgcgggcc cagcatgagg accaggtgga gcagtataag  780
aaggagctgg agaagactta ttctgccaag ctggacaatg ccaggcagtc tgctgagagg  840
aacagcaacc tggtgggggc tgcccacgag gagctgcagc agtcgcgcat ccgcatcgac  900
agcctctctg cccagctcag ccagctccag aagcagctgg cagccaagga ggcgaagctt  960
cgagacctgg aggactcact ggcccgtgag cgggacacca gccggcggct gctggcggaa  1020
aaggagcggg agatggccga gatgcgggca aggatgcagc agcagctgga cgagtaccag  1080
gagcttctgg acatcaagct ggccctggac atggagatcc acgcctaccg caagctcttg  1140
gagggcgagg aggagaggct acgcctgtcc cccagcccta cctcgcagcg cagccgtggc  1200
cgtgcttcct ctcactcatc ccagacacag ggtgggggca gcgtcaccaa aaagcgcaaa  1260
ctggagtcca ctgagagccg cagcagcttc tcacagcacg cacgcactag cgggcgcgtg  1320
gccgtggagg aggtggatga ggagggcaag tttgtccggc tgcgcaacaa gtccaatgag  1380
gaccagtcca tgggcaattg gcagatcaag cgccagaatg gagatgatcc cttgctgact  1440
taccggttcc caccaaagtt caccctgaag gctgggcagg tggtgacgat ctgggctgca  1500
ggagctgggg ccacccacag ccccccctacc gacctggtgt ggaaggcaca gaacacctgg  1560
ggctgcggga acagcctgcg tacggctctc atcaactcca ctggggaaga agtggccatg  1620
cgcaagctgg tgcgctcagt gactgtggtt gaggacgacg aggatgagga tggagatgac  1680
ctgctccatc accaccacgt gagtggtagc cgccgctga                      1719

SEQ ID NO: 22          moltype = AA  length = 572
FEATURE                Location/Qualifiers
source                 1..572
                       mol_type = protein
                       organism = Homo sapiens
SEQUENCE: 22
METPSQRRAT RSGAQASSTP LSPTRITRLQ EKEDLQELND RLAVYIDRVR SLETENAGLR  60
LRITESEEVV SREVSGIKAA YEAELGDARK TLDSVAKERA RLQLELSKVR EEFKELKARN  120
TKKEGDLIAA QARLKDLEAL LNSKEAALST ALSEKRTLEG ELHDLRGQVA KLEAALGEAK  180
KQLQDEMLRR VDAENRLQTM KEELDFQKNI YSEELRETKR RHETRLVEID NGKQREFESR  240
LADALQELRA QHEDQVEQYK KELEKTYSAK LDNARQSAER NSNLVGAAHE ELQQSRIRID  300
SLSAQLSQLQ KQLAAKEAKL RDLEDSLARE RDTSRRLLAE KEREMAEMRA RMQQQLDEYQ  360
ELLDIKLALD MEIHAYRKLL EGEEERLRLS PSPTSQRSRG RASSHSSQTQ GGGSVTKKRK  420
LESTESRSSF SQHARTSGRV AVEEVDEEGK FVRLRNKSNE DQSMGNWQIK RQNGDDPLLT  480
YRFPPKFTLK AGQVVTIWAA GAGATHSPPT DLVWKAQNTW GCGNSLRTAL INSTGEEVAM  540
RKLVRSVTVV EDDEDEDGDD LLHHHHVSGS RR                               572

SEQ ID NO: 23          moltype = DNA  length = 1761
FEATURE                Location/Qualifiers
source                 1..1761
                       mol_type = genomic DNA
                       organism = Homo sapiens
SEQUENCE: 23
atggcgactg cgaccccccgt gccgccgcgg atgggcagcc gcgctggcgg ccccaccacg  60
ccgctgagcc ccacgcgcct gtcgcggctc caggagaagg aggagctgcg cgagctcaat  120
gaccggctgg cggtgtacat cgacaaggtg cgcagcctgg agacggagaa cagcgcgctg  180
cagctgcagg tgacggagcg cgaggaggtg cgcggccgtg agctcaccgg cctcaaggcg  240
ctctacgaga ccgagctggc cgacgcgcga cgcgcgctcg acgacacggc ccgcgagcgc  300
gccaagctgc agatcgagct gggcaagtgc aaggcggaac acgaccagct gctcctcaac  360
tatgctaaga aggaatctga tcttaatggc gcccagatca agcttcgaga atatgaagca  420
gcactgaatt cgaaagatgc agctcttgct actgcacttg gtgacaaaaa aagtttagag  480
ggagatttgg aggatctgaa ggatcagatt gcccagttgg aagcctcctt agctgcagcc  540
aaaaaacagt tagcagatga aactttactt aaagtagatt tggagaatcg ttgtcagagc  600
cttactgagg acttggagtt tcgcaaaagc atgtatgaag aggagattaa cgagaccaga  660
aggaagcatg aaacgcgctt ggtagaggtg gattctgggc gtcaaattga gtatgagtac  720
aagctggcgc aagcccttca tgagatgaga gagcaacatg atgcccaagt gaggctgtat  780
aaggaggagc tggagcagac ttaccatgcc aaacttgaga atgccagact gtcatcagag  840
atgaatactt ctactgtcaa cagtgccagg gaagaactga tggaaagccg catgagaatt  900
gagagccttt catcccagct ttctaatcta cagaaagagt ctagagcatg tttggaaagg  960
attcaagaat tagaggactt gcttgctaaa gaaaaagaca actctcgtcg catgctgaca  1020
gacaaagaga gagagatggc ggaaataagg gatcaaatgc agcaacagct gaatgactat  1080
gaacagcttc ttgatgtaaa gttagccctg gacatggaaa tcagtgctta caggaaactc  1140
```

```
ttagaaggcg aagaagagag gttgaagctg tctccaagcc cttcttcccg tgtgacagta  1200
tcccgagcat cctcaagtcg tagtgtacgt acaactagag gaaagcggaa gagggttgat  1260
gtggaagaat cagaggcgag tagtagtgtt agcatctctc attccgcctc agccactgga  1320
aatgtttgca tcgaagaaat tgatgttgat gggaaattta tccgcttgaa gaacacttct  1380
gaacaggatc aaccaatggg aggctgggag atgatcagaa aaattggaga cacatcagtc  1440
agttataaat atacctcaag atatgtgctg aaggcaggcc agactgttac aatttgggct  1500
gcaaacgctg gtgtcacagc cagcccccca actgacctca tctggaagaa ccagaactcg  1560
tggggcactg gcgaagatgt gaaggttata ttgaaaaatt ctcagggaga ggaggttgct  1620
caaagaagta cagtctttaa aacaaccata cctgaagaag aggaggagga ggaagaagca  1680
gctggagtgg ttgttgagga agaacttttc caccagcagg gaaccccaag agcatccaat  1740
agaagctgtg caattatgta a                                            1761

SEQ ID NO: 24          moltype = AA  length = 586
FEATURE                Location/Qualifiers
source                 1..586
                       mol_type = protein
                       organism = Homo sapiens
SEQUENCE: 24
MATATPVPPR MGSRAGGPTT PLSPTRLSRL QEKEELRELN DRLAVYIDKV RSLETENSAL  60
QLQVTEREEV RGRELTGLKA LYETELADAR RALDDTARER AKLQIELGKC KAEHDQLLLN  120
YAKKESDLNG AQIKLREYEA ALNSKDAALA TALGDKKSLE GDLEDLKDQI AQLEASLAAA  180
KKQLADETLL KVDLENRCQS LTEDLEFRKS MYEEEINETR RKHETRLVEV DSGRQIEYEY  240
KLAQALHEMR EQHDAQVRLY KEELEQTYHA KLENARLSSE MNTSTVNSAR EELMESRMRI  300
ESLSSQLSNL QKESRACLER IQELEDLLAK EKDNSRRMLT DKEREMAEIR DQMQQQLNDY  360
EQLLDVKLAL DMEISAYRKL LEGEEERLKL SPSPSSRVTV SRASSSRSVR TTRGKRKRVD  420
VEESEASSSV SISHSASATG NVCIEEIDVD GKFIRLKNTS EQDQPMGGWE MIRKIGDTSV  480
SYKYTSRYVL KAGQTVTIWA ANAGVTASPP TDLIWKNQNS WGTGEDVKVI LKNSQGEEVA  540
QRSTVFKTTI PEEEEEEEEA AGVVVEEELF HQQGTPRASN RSCAIM                 586

SEQ ID NO: 25          moltype = DNA  length = 1863
FEATURE                Location/Qualifiers
source                 1..1863
                       mol_type = genomic DNA
                       organism = Homo sapiens
SEQUENCE: 25
atgagcccgc cgagcccggg ccgccgtcgg gagcagcgca ggccgcgagc cgccgccacc  60
atggccacgc cgctgcccgg ccgcgcgggc gggcccgcca cgccgctgtc gcccacgcgc  120
ctgtcgcggc tgcaggagaa ggaggagctg cgcgagctca acgaccgcct ggcgcactac  180
atcgaccgcg tccgcgcgct ggagctggag aacgaccggc tcctgctcaa gatctcagag  240
aaggaggagg tgaccacgcg cgaggtgagt ggcatcaagg cgctgtacga gtcggagctg  300
gccgatgccc ggagagtcct ggatgagacg gctcgagagc gtgcccggct gcagatagag  360
attgggaagc tgagggcaga gttggacgag gtcaacaaga gcgccaagaa gagggagggc  420
gagcttacgg tggcccaggg ccgtgtgaag gacctggagt ccctgttcca ccggagcgag  480
gtggagctgg cagctgccct cagcgacaag cgcggcctgg agagtgacgt ggctgagctg  540
cgggcccagc tggccaaggc cgaggacggt catgcagtgg ccaaaaagca gctggagaag  600
gagacgctga tgcgtgtgga cctggagaac cgctgccaga gcctgcagga ggagctggac  660
ttccggaaga gtgtgttcga ggaggaggtg cgggagacgc ggcggcggca cgagcggcgc  720
ctggtggagg tggacagcag ccggcagcag gagtacgact tcaagatggc acaggcgctg  780
gaggagctgc ggagccagca cgacgagcaa gtgcggctct acaagctgga gctggagcag  840
acctaccagg ccaagctgga cagcgccaag ctgagctctg accagaacga caaggcggcc  900
agtgcggctc gcgaggagct gaaggaggcc cgcatgcgcc tggagtccct cagctaccag  960
ctctccggcc tccagaagca ggccagtgcc gctgaagatc gcattcggga gctggaggag  1020
gccatggccg gggagcggga caagttccgg aagatgctgg acgccaagga gcaggagatg  1080
acggagatgc gggacgtgat gcagcagcag ctggccgagt accaggagct gctggacgtg  1140
aagctggccc tggacatgga gatcaacgcc taccggaagc tcctggaggg cgaggaggag  1200
aggctgaagc tgtcccccag cccatcctcg cgcgtcaccg tctcacgagc cacctcgagc  1260
agcagcggca gcttgtccgc caccgggcgc ctgggccgca gtaagcggaa gcggctggag  1320
gtggaggagc ccttgggcag cggcccaagc gtcctgggca cgggcacggg tggcagcggt  1380
ggcttccacc tggcccagca ggcctcggcc tcgggtagcg tcagcatcga ggagatcgac  1440
ctggagggca agtttgtgca gctcaagaac aactcggaca aggatcagtc tctggggaac  1500
tggagaatca agaggcaggt cttggagggg gaggagatcg cctacaagtt cacgcccaag  1560
tacatcctgc gcgccggcca gatggtcacg gtgtgggcag ctggtgcggg ggtggcccac  1620
agccccccct cgacgctggt gtggaagggc cagagcagct ggggcacggg cgagagcttc  1680
cgcaccgtcc tggttaacgc ggatggcgag gaagtggcca tgaggactgt gaagaagtcc  1740
tcggtgatgc gtgagaatga gaatggggag gaagaggagg aggaagccga gtttggcgag  1800
gaggatcttt tccaccaaca gggggacccg aggaccacct caagaggctg ctacgtgatg  1860
tga                                                                1863

SEQ ID NO: 26          moltype = AA  length = 620
FEATURE                Location/Qualifiers
source                 1..620
                       mol_type = protein
                       organism = Homo sapiens
SEQUENCE: 26
MSPPSPGRRR EQRRPRAAAT MATPLPGRAG GPATPLSPTR LSRLQEKEEL RELNDRLAHY  60
IDRVRALELE NDRLLLKISE KEEVTTREVS GIKALYESEL ADARRVLDET ARERARLQIE  120
IGKLRAELDE VNKSAKKREG ELTVAQGRVK DLESLFHRSE VELAAALSDK RGLESDVAEL  180
RAQLAKAEDG HAVAKKQLEK ETLMRVDLEN RCQSLQEELD FRKSVFEEEV RETRRRHERR  240
LVEVDSSRQQ EYDFKMAQAL EELRSQHDEQ VRLYKLELEQ TYQAKLDSAK LSSDQNDKAA  300
```

```
SAAREELKEA RMRLESLSYQ LSGLQKQASA AEDRIRELEE AMAGERDKFR KMLDAKEQEM  360
TEMRDVMQQQ LAEYQELLDV KLALDMEINA YRKLLEGEEE RLKLSPSPSS RVTVSRATSS  420
SSGSLSATGR LGRSKRKRLE VEEPLGSGPS VLGTGTGGSG GFHLAQQASA SGSVSIEEID  480
LEGKFVQLKN NSDKDQSLGN WRIKRQVLEG EEIAYKFTPK YILRAGQMVT VWAAGAGVAH  540
SPPSTLVWKG QSSWGTGESF RTVLVNADGE EVAMRTVKKS SVMRENENGE EEEEEAEFGE  600
EDLFHQQGDP RTTSRGCYVM                                              620

SEQ ID NO: 27          moltype = AA  length = 483
FEATURE                Location/Qualifiers
source                 1..483
                       mol_type = protein
                       organism = Homo sapiens
SEQUENCE: 27
VSLWGQGNFF SLLPVLNWTA MQPTQRVDDS KGMHRPGPLP PSPPPKVDHK ASQWPQESDM  60
GQKVASLSAQ CHNHDERLAE LTVLLQKLQI RVDQVDDGRE GLSLWVKNVV GQHLQEMGTI  120
EPPDAKTDFM TFHHDHEVRL SNLEDVLRKL TEKSEAIQKE LEETKLKAGS RDEEQPLLDR  180
VQHLELELNL LKSQLSDWQH LKTSCEQAGA RIQETVQLMF SEDQQGGSLE WLLEKLSSRF  240
VSKDELQVLL HDLELKLLQN ITHHITVTGQ APTSEAIVSA VNQAGISGIT EAQAHIIVNN  300
ALKLYSQDKT GMVDFALESG GGSILSTRCS ETYETKTALL SLFGVPLWYF SQSPRVVIQP  360
DIYPGNCWAF KGSQGYLVVR LSMKIYPTTF TMEHIPKTLS PTGNISSAPK DFAVYGLETE  420
YQEEGQPLGR FTYDQEGDSL QMFHTLERPD QAFQIVELRV LSNWGHPEYT CLYRFRVHGE  480
PIQ                                                                483

SEQ ID NO: 28          moltype = AA  length = 746
FEATURE                Location/Qualifiers
source                 1..746
                       mol_type = protein
                       organism = synthetic construct
SEQUENCE: 28
MKLGRAVLGL LLLAPSVVQA VASVSKGEEL FTGVVPILVE LDGDVNGHKF SVSGEGEGDA  60
TYGKLTLKFI CTTGKLPVPW PTLVTTLTYG VQCFSRYPDH MKQHDFFKSA MPEGYVQERT  120
IFFKDDGNYK TRAEVKFEGD TLVNRIELKG IDFKEDGNIL GHKLEYNYNS HNVYIMADKQ  180
KNGIKVNFKI RHNIEDGSVQ LADHYQQNTP IGDGPVLLPD NHYLSTQSAL SKDPNEKRDH  240
MVLLEFVTAA GITLGMDELY KEFVSLWGQG NFFSLLPVLN WTAMQPTQRV DDSKGMHRPG  300
PLPPSPPPKV DHKASQWPQE SDMGQKVASL SAQCHNHDER LAELTVLLQK LQIRVDQVDD  360
GREGLSLWVK NVVGQHLQEM GTIEPPDAKT DFMTFHHDHE VRLSNLEDVL RKLTEKSEAI  420
QKELEETKLK AGSRDEEQPL LDRVQHLELE LNLLKSQLSD WQHLKTSCEQ AGARIQETVQ  480
LMFSEDQQGG SLEWLLEKLS SRFVSKDELQ VLLHDLELKL LQNITHHITV TGQAPTSEAI  540
VSAVNQAGIS GITEAQAHII VNNALKLYSQ DKTGMVDFAL ESGGGSILST RCSETYETKT  600
ALLSLFGVPL WYFSQSPRVV IQPDIYPGNC WAFKGSQGYL VVRLSMKIYP TTFTMEHIPK  660
TLSPTGNISS APKDFAVYGL ETEYQEEGQP LGRFTYDQEG DSLQMFHTLE RPDQAFQIVE  720
LRVLSNWGHP EYTCLYRFRV HGEPIQ                                       746

SEQ ID NO: 29          moltype = AA  length = 21
FEATURE                Location/Qualifiers
source                 1..21
                       mol_type = protein
                       organism = synthetic construct
SEQUENCE: 29
MKLGRAVLGL LLLAPSVVQA V                                            21

SEQ ID NO: 30          moltype = AA  length = 237
FEATURE                Location/Qualifiers
source                 1..237
                       mol_type = protein
                       organism = synthetic construct
SEQUENCE: 30
SKGEELFTGV VPILVELDGD VNGHKFSVSG EGEGDATYGK LTLKFICTTG KLPVPWPTLV  60
TTLTYGVQCF SRYPDHMKQH DFFKSAMPEG YVQERTIFFK DDGNYKTRAE VKFEGDTLVN  120
RIELKGIDFK EDGNILGHKL EYNYNSHNVY IMADKQKNGI KVNFKIRHNI EDGSVQLADH  180
YQQNTPIGDG PVLLPDNHYL STQSALSKDP NEKRDHMVLL EFVTAAGITL GMDELYK     237

SEQ ID NO: 31          moltype = AA  length = 483
FEATURE                Location/Qualifiers
source                 1..483
                       mol_type = protein
                       organism = synthetic construct
SEQUENCE: 31
VSLWGQGNFF SLLPVLNWTA MQPTQRVDDS KGMHRPGPLP PSPPPKVDHK ASQWPQESDM  60
GQKVASLSAQ CHNHDERLAE LTVLLQKLQI RVDQVDDGRE GLSLWVKNVV GQHLQEMGTI  120
EPPDAKTDFM TFHHDHEVRL SNLEDVLRKL TEKSEAIQKE LEETKLKAGS RDEEQPLLDR  180
VQHLELELNL LKSQLSDWQH LKTSCEQAGA RIQETVQLMF SEDQQGGSLE WLLEKLSSRF  240
VSKDELQVLL HDLELKLLQN ITHHITVTGQ APTSEAIVSA VNQAGISGIT EAQAHIIVNN  300
ALKLYSQDKT GMVDFALESG GGSILSTRCS ETYETKTALL SLFGVPLWYF SQSPRVVIQP  360
DIYPGNCWAF KGSQGYLVVR LSMKIYPTTF TMEHIPKTLS PTGNISSAPK DFAVYGLETE  420
YQEEGQPLGR FTYDQEGDSL QMFHTLERPD QAFQIVELRV LSNWGHPEYT CLYRFRVHGE  480
PIQ                                                                483
```

The invention claimed is:

1. A method of identifying a skin-softening compound, the method comprising:

1. Contacting, in the presence of a test compound, a Sad1 and UNC-84 homology (SUN) fusion protein that consists of a SUN domain with a Klarsicht, ANC-1, Syne Homology (KASH) domain; and
2. Detecting a signal, using a binding assay, wherein:
    - the signal results from binding between the SUN domain and the KASH domain, and
    - an alteration in binding as compared to a control is an indicator that the test compound is a candidate skin-softening compound that disrupts a linker of the nucleoskeleton and cytoskeleton (LINC) complex comprising a SUN domain and a KASH domain.

2. The method of claim 1, wherein the alteration is increased binding between the SUN domain and the KASH domain.

3. The method of claim 1, wherein the alteration is reduced binding between the SUN domain and the KASH domain.

4. The method of claim 1, wherein the KASH domain is encoded by a nucleotide sequence substantially as set out in SEQ ID No. 1, 3, 5 and/or 7, or a variant or fragment thereof.

5. The method of claim 1, wherein the KASH domain comprises an amino acid sequence substantially as set out in SEQ ID No. 2, 4, 6 and/or 8, or a variant or fragment thereof.

6. The method of claim 1, wherein the SUN domain is encoded by a nucleotide sequence substantially as set out in SEQ ID No. 9, 11, 13, 15 and/or 17, or a variant or fragment thereof.

7. The method of claim 1, wherein the SUN domain comprises an amino acid nucleotide sequence substantially as set out in SEQ ID No. 10, 12, 14, 16 and/or 18, or a variant or fragment thereof.

8. The method of claim 1, wherein the LINC complex comprises a Nesprin and a SUN protein.

9. The method of claim 8, wherein the Nesprin protein comprises the KASH domain and the SUN protein comprises the SUN domain.

10. The method of claim 8, wherein the Nesprin and SUN proteins are bound to each other with a 3:3 stoichiometry to form a hexameric complex.

11. The method of claim 1, wherein the test compound that disrupts the LINC complex is an agent that inhibits or is configured to inhibit binding of a Nesprin protein to a SUN protein.

12. The method of claim 11, wherein the Nesprin protein is a Nesprin-2 protein.

13. The method of claim 11, wherein the Sun protein is a SUN1 or SUN2 protein.

14. The method of claim 1, wherein the test compound that disrupts the LINC complex inhibits binding of a KASH domain to a SUN domain.

15. The method of claim 12, wherein the binding assay comprises protein complex immunoprecipitation, Bimolecular Fluorescence complementation, Affinity electrophoresis, Immunoelectrophoresis, chemical cross linking, Proximity ligation assay, FRET, or any combination thereof.

16. The method of claim 1, wherein the test compound is a modified Nesprin protein that does not comprise a KASH domain, or a variant or a fragment thereof.

17. The method of claim 1, wherein the test compound is a modified Nesprin that consists of a KASH domain.

18. The method of claim 1, wherein the test compound is a modified SUN protein that consists of a SUN domain.

19. The method of claim 1, wherein the test compound that disrupts the LINC complex is an agent that promotes or is configured to promote degradation of the LINC complex or one or more of the LINC complex proteins.

20. The method of claim 1, wherein the test compound that disrupts the LINC complex is an agent that reduces or is configured to reduce the concentration of a LINC complex protein compared to the concentration of the LINC complex protein in the absence of the agent.

* * * * *